US011180772B2

(12) United States Patent
Schultheiss et al.

(10) Patent No.: US 11,180,772 B2
(45) Date of Patent: *Nov. 23, 2021

(54) FUNGAL RESISTANT PLANTS EXPRESSING RLK2

(71) Applicant: BASF PLANT SCIENCE COMPANY GMBH, Ludwigshafen (DE)

(72) Inventors: Holger Schultheiss, Boehl-Iggelheim (DE); Tobias Mentzel, Roemerberg (DE); Ralf Flachmann, Limburgerhof (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/049,245

(22) Filed: Jul. 30, 2018

(65) Prior Publication Data

US 2018/0334682 A1 Nov. 22, 2018

Related U.S. Application Data

(63) Continuation of application No. 14/419,330, filed as application No. PCT/IB2013/056315 on Aug. 1, 2013, now Pat. No. 10,066,239.

(60) Provisional application No. 61/681,165, filed on Aug. 9, 2012.

(30) Foreign Application Priority Data

Aug. 9, 2012 (EP) .................................... 12179878

(51) Int. Cl.
*C12N 15/82* (2006.01)
*C12N 9/12* (2006.01)

(52) U.S. Cl.
CPC ....... *C12N 15/8282* (2013.01); *C12N 9/1205* (2013.01)

(58) Field of Classification Search
None
See application file for complete search history.

(56) References Cited

U.S. PATENT DOCUMENTS

| | | | | |
|---|---|---|---|---|
| 10,066,239 | B2 * | 9/2018 | Schultheiss | C12N 9/1205 |
| 2007/0214517 | A1 * | 9/2007 | Alexandrov | C07K 14/415 800/278 |
| 2008/0057093 | A1 | 3/2008 | Wan et al. | |
| 2011/0247101 | A1 | 10/2011 | Alexandrov et al. | |
| 2015/0211018 | A1 | 7/2015 | Schultheiss et al. | |

FOREIGN PATENT DOCUMENTS

| | | | |
|---|---|---|---|
| CN | 1974772 | A | 6/2007 |
| CN | 102533812 | A | 7/2012 |
| CN | 102586291 | A | 7/2012 |
| WO | WO-2009/134339 | A2 | 11/2009 |
| WO | WO-2010/037714 | A1 | 4/2010 |
| WO | WO-2010/039750 | A2 | 4/2010 |
| WO | WO-2012/023099 | A1 | 2/2012 |
| WO | WO-2012/023111 | A1 | 2/2012 |
| WO | WO-2012/172498 | A1 | 12/2012 |
| WO | WO-2013/001435 | A1 | 1/2013 |
| WO | WO-2013/092275 | A2 | 6/2013 |
| WO | WO-2013/093738 | A1 | 6/2013 |
| WO | WO-2013/149801 | A1 | 10/2013 |
| WO | WO-2013/149804 | A1 | 10/2013 |
| WO | WO-2013/152917 | A1 | 10/2013 |
| WO | WO-2014/024079 | A2 | 2/2014 |
| WO | WO-2014/024090 | A2 | 2/2014 |
| WO | WO-2014/024102 | A1 | 2/2014 |
| WO | WO-2014/041444 | A1 | 3/2014 |
| WO | WO-2014/076614 | A1 | 5/2014 |
| WO | WO-2014/117988 | A1 | 8/2014 |
| WO | WO-2014/117990 | A1 | 8/2014 |
| WO | WO-2014/118018 | A1 | 8/2014 |

OTHER PUBLICATIONS

Gou et al (2010, BMC Genomics 11:19).*
He et al (2006, Cell 125, 563-575).*
GenBank C0LGG6 (2009, https://www.ncbi.nlm.nih.gov/protein/C0LGG6.1).*
At1g51890 (https://www.uniprot.org/uniprot/C0LGG6, accessed Aug. 12, 2019).*
Ahmed et al., "Plant Receptor-Like Serine Threonine Kinases: Roles in Signaling and Plant Defense", *MPMI*, 21(5):507-517 (2008).
European Search Report, corresponding to European application No. EP 12 17 9878, Nov. 29, 2012.
Frederick et al., "Polymerase chain reaction assays for the detection and discrimination of the soybean rust pathogens *Phakopsora pachyrhizi* and *P. meibomiae*", *Phytopathology*, 92(2):217-227 (2002).
Gao et al., "Global Analysis of Expression Profiles of Rice Receptor-Like Kinase Genes", *Molecular Plant*, 5(1):143-153 (2012).
GenBank Accession No. NM104069, "*Arabidopsis thaliana* putative leucine-rich repeat protein kinase (AT1G51890) mRNA, complete cds" dated May 28, 2011.

(Continued)

*Primary Examiner* — Anne Kubelik
(74) *Attorney, Agent, or Firm* — Marshall, Gerstein & Borun LLP

(57) ABSTRACT

The present invention relates to a method of increasing resistance against fungal pathogens of the order Pucciniales, preferably the family Phacopsoraceae, in plants and/or plant cells. This is achieved by increasing the expression of an RLK2 protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the order Pucciniales, preferably the family Phacopsoraceae, and to recombinant expression vectors comprising a sequence that is identical or homologous to a sequence encoding an RLK2 protein.

5 Claims, 11 Drawing Sheets

Specification includes a Sequence Listing.

(56) References Cited

OTHER PUBLICATIONS

GenBank Accession No. NP175601, "Putative leucine-rich repeat protein kinase [*Arabidopsis thaliana*]" dated May 28, 2011.
Guo et al., Protein tolerance to random amino acid change, Proc. Natl. Acad. Sci. USA, 101(25):9205-10 (2004).
Heath, "Cellular interactions between biotrophic fungal pathogens and host or nonhost plants", *Can. J. Plant Pathol.*, 24:259-264 (2002).
International Search Report and Written Opinion, corresponding International Application No. PCT/IB2013/056315, dated Jan. 2, 2014.
Morillo et al., "Functional analysis of receptor-like kinases in monocots and dicots", *Current Opinion in Plant Biology*, 9:460-469 (2006).
Neu et al., "Cytological and molecular analysis of the *Hordeum vulgare-Puccinia triticina* nonhost interaction", *MPMI*, 16(7):626-633 (2003).
Nürnberger et al., "Receptor protein kinases—pattern recognition receptors in plant immunity", *Trends in Plant Science*, 11(11):519-522 (2006).
Rytter et al., "Additional alternative hosts of *Phakopsora pachyrhizi*, causal agent of soybean rust", *Plant Dis.*, 87:818-819 (1984).
Sinclair et al., (eds.) Proceedings of the Soybean Rust Workshop, Aug. 9-11, 1995. Urbana, IL: National Soybean Research Laboratory, (1995).
Zhou et al., "Molecular analysis of three new receptor-like kinase genes from hexapioid wheat and evidence for their participation in the wheat hypersensitive response to stripe rust fungus infection", *The Plant Journal*, 52:420-434 (2007).

* cited by examiner

Figure 3:

```
   1 ATGAGGTTTT TGTCTTTCTT GATCTTCGTT TTCGCAGTTC TTGGATTGGT
  51 TCAAGCTCAA GACCAATCAG GATTCATAAG CTTAGATTGT GGTTTGGTGC
 101 CTACGGAAAT TACTTATGTG GAAAAGTCGA CGAATATAAC ATACAGATCA
 151 GACGCAACTT ACATCGACAG TGGAGTTCCC GGGAAGATCA ATGAAGTGTA
 201 CAGAACACAG TTTCAGCAAC AAATTTGGGC CTTGAGAAGC TTCCCTGAGG
 251 GTCAAAGAAA TTGTTACAAC TTCAGTCTCA CCGCAAAACG TAAGTATCTA
 301 ATCAGAGGAA CCTTTATCTA TGGGAATTAT GACGGTTTGA ATCAACTCCC
 351 GAGCTTTGAT CTTTACATCG GTCCAAACAA ATGGACCTCT GTTTCGATCC
 401 CCGGAGTGAG AAATGGTTCA GTCTCCGAGA TGATCCATGT CTTAAGACAA
 451 GACCATCTTC AAATTTGTCT TGTGAAAACA GGAGAAACTA CACCGTTTAT
 501 TTCTTCATTG GAACTTCGTC CTTTGAACAA TAATACATAC GTCACAAAAA
 551 GTGGATCGCT TATTGTGGTC GCAAGACTTT ACTTTTCACC CACTCCACCA
 601 TTTCTCAGGT ATGATGAGGA CGTCCATGAC CGAATTTGGA TTCCATTCTT
 651 AGATAACAAA AATTCCTTGT TAAGCACGGA ACTCTCTGTT GATACAAGTA
 701 ACTTCTACAA TGTGCCTCAA ACTGTAGCGA AAACTGCTGC TGTCCCTTTA
 751 AATGCTACTC AGCCTCTGAA AATAAATTGG AGTCTCGACG ACATCACTTC
 801 ACAGTCATAT ATATACATGC ATTTCGCTGA AATCGAGAAT CTTGAAGCTA
 851 ATGAGACCAG AGAATTCAAT ATTACTTACA ATGGTGGCGA AAATTGGTTC
 901 TCCTATTTTA GACCTCCAAA GTTTCGTATA ACAACTGTAT ACAATCCAGC
 951 AGCTGTGAGT TCTCTAGATG GGAATTTCAA CTTCACTTTC TCGATGACCG
1001 GTAACTCTAC TCATCCTCCT CTTATCAACG GCCTTGAGAT TTATCAAGTT
1051 CTAGAGCTTC CACAGCTTGA TACATACCAA GATGAAGTTT CCGCTATGAT
1101 GAATATCAAG ACAATATATG GATTGAGCAA AAGGTCTAGC TGGCAAGGAG
1151 ATCCATGTGC TCCTGAGTTA TATAGATGGG AAGGTTTAAA CTGTAGTTAT
1201 CCAAACTTTG CGCCACCGCA GATCATATCC TTGAACTTGA GTGGAAGCAA
1251 TTTGAGTGGT ACCATAACAT CTGATATATC CAAGCTAACA CATTTGAGAG
1301 AACTAGATTT ATCAAACAAT GACTTATCAG GAGATATTCC ATTTGTTTTT
1351 TCTGATATGA AGAATTTGAC ACTCATAAAC TTGAGTGGAA ACAAGAATCT
1401 AAATCGCTCA GTTCCAGAGA CTCTTCAGAA GAGGATAGAT AACAAATCTT
1451 TAACACTAAT TAGAGATGAA ACCGGAAAAA ATAGTACAAA TGTAGTTGCT
1501 ATCGCAGCAT CAGTGGCTAG CGTGTTTGCT GTGCTAGTTA TCTTGGCTAT
1551 CGTTTTTGTC GTCATAAGGA AAAAACAGAG AACTAATGAA GCTTCAGGAC
1601 CCCGATCATT CACTACTGGC ACGGTTAAGA GTGATGCAAG ATCATCGAGT
1651 TCATCAATCA TAACAAAGGA ACGCAAGTTC ACTTATTCGG AGGTACTAAA
1701 GATGACTAAA AACTTTGAGA GAGTTCTTGG TAAAGGAGGG TTTGGAACAG
1751 TGTATCATGG TAACTTGGAT GATACTCAAG TAGCTGTGAA AATGCTTTCT
1801 CATTCATCAG CTCAAGGTTA TAAAGAGTTC AAAGCAGAGG TTGAACTTCT
1851 TTTAAGAGTT CATCACAGAC ATTTGGTGGG ACTTGTTGGT TACTGTGATG
1901 ATGGAGACAA CTTAGCTCTG ATCTATGAAT ATATGGAAAA AGGAGACCTG
1951 AGGGAAAATA TGTCAGGAAA ACACAGTGTC AATGTCCTAA GCTGGGAAAC
2001 AAGAATGCAA ATAGCTGTAG AGGCAGCACA AGGATTGGAG TATTTGCATA
2051 ACGGATGTAG GCCTCCTATG GTACATAGAG ATGTGAAACC AACCAACATT
2101 TTATTAAATG AGCGGTCTCA AGCAAAACTA GCCGACTTTG GGCTATCGAG
2151 ATCTTTTCCT GTTGATGGTG AATCTCATGT CATGACAGTC GTTGCAGGAA
2201 CACCTGGTTA CTTAGATCCT GAGTATTACA GAACAAACTG GCTAAGCGAG
2251 AAGAGTGATG TGTACAGCTT TGGTGTAGTG CTTTTAGAGA TAGTCACAAA
2301 CCAGCCTGTG ATGAATAAAA ACCGAGAGAG ACCTCATATC AATGAATGGG
2351 TTATGTTCAT GCTTACCAAT GGGGATATCA AGAGTATTGT CGACCCGAAA
2401 CTGAATGAAG ACTATGACAC AAACGGTGTG TGGAAGGTTG TAGAGTTGGC
2451 TTTAGCTTGT GTAAACCCGT CTTCAAGCCG TAGACCGACA ATGCCACACG
2501 TGGTGATGGA GCTAAACGAA TGTCTTGCTT TGGAAATAGA AAGGAAACAA
2551 GGTAGTCAAG CGACGTACAT AAAGGAATCT GTTGAGTTTA GTCCATCTTC
2601 TGCTTCTGAT TTTTCCCCTT TAGCTAGGTA A
```

Figure 4:

```
MRFLSFLIFVFAVLGLVQAQDQSGFISLDCGLVPTEITYVEKSTNITYRS  50
DATYIDSGVPGKINEVYRTQFQQQIWALRSFPEGQRNCYNFSLTAKRKYL 100
IRGTFIYGNYDGLNQLPSFDLYIGPNKWTSVSIPGVRNGSVSEMIHVLRQ 150
DHLQICLVKTGETTPFISSLELRPLNNNTYVTKSGSLIVVARLYFSPTPP 200
FLRYDEDVHDRIWIPFLDNKNSLLSTELSVDTSNFYNVPQTVAKTAAVPL 250
NATQPLKINWSLDDITSQSYIYMHFAEIENLEANETREFNITYNGGENWF 300
SYFRPPKFRITTVYNPAAVSSLDGNFNFTFSMTGNSTHPPLINGLEIYQV 350
LELPQLDTYQDEVSAMMNIKTIYGLSKRSSWQGDPCAPELYRWEGLNCSY 400
PNFAPPQIISLNLSGSNLSGTITSDISKLTHLRELDLSNNDLSGDIPFVF 450
SDMKNLTLINLSGNKNLNRSVPETLQKRIDNKSLTLIRDETGKNSTNVVA 500
IAASVASVFAVLVILAIVFVVIRKKQRTNEASGPRSFTTGTVKSDARSSS 550
SSIITKERKFTYSEVLKMTKNFERVLGKGGFGTVYHGNLDDTQVAVKMLS 600
HSSAQGYKEFKAEVELLLRVHHRHLVGLVGYCDDGDNLALIYEYMEKGDL 650
RENMSGKHSVNVLSWETRMQIAVEAAQGLEYLHNGCRPPMVHRDVKPTNI 700
LLNERSQAKLADFGLSRSFPVDGESHVMTVVAGTPGYLDPEYYRTNWLSE 750
KSDVYSFGVVLLEIVTNQPVMNKNRERPHINEWVMFMLTNGDIKSIVDPK 800
LNEDYDTNGVWKVVELALACVNPSSSRRPTMPHVVMELNECLALEIERKQ 850
GSQATYIKESVEFSPSSASDFSPLAR*
```

Figure 5:

```
   1 ATGAGGTTTT TGTCTTTCTT GATCTTCGTT TTCGCAGTTC TTGGATTGGT
  51 TCAAGCTCAA GACCAATCAG GTTATTTACT CTGTTTTCAT GAAATCTTGA
 101 TGTTTTGTTT CCTTTTCAGA TCAACAAAAC CTCTTAAAAG TTTGTTTTTT
 151 TCGATCATAA ACAGGATTCA TAAGCTTAGA TTGTGGTTTG GTGCCTACGG
 201 AAATTACTTA TGTGGAAAAG TCGACGAATA TAACATACAG ATCAGACGCA
 251 ACTTACATCG ACAGTGGAGT TCCCGGGAAG ATCAATGAAG TGTACAGAAC
 301 ACAGTTTCAG CAACAAATTT GGGCCTTGAG AAGCTTCCCT GAGGGTCAAA
 351 GAAATTGTTA CAACTTCAGT CTCACCGCAA AACGTAAGTA TCTAATCAGA
 401 GGAACCTTTA TCTATGGGAA TTATGACGGT TTGAATCAAC TCCCGAGCTT
 451 TGATCTTTAC ATCGGTCCAA ACAAATGGAC CTCTGTTTCG ATCCCCGGAG
 501 TGAGAAATGG TTCAGTCTCC GAGATGATCC ATGTCTTAAG ACAAGACCAT
 551 CTTCAAATTT GTCTTGTGAA AACAGGAGAA ACTACACCGT TTATTTCTTC
 601 ATTGGAACTT CGTCCTTTGA ACAATAATAC ATACGTCACA AAAAGTGGAT
 651 CGCTTATTGT GGTCGCAAGA CTTTACTTTT CACCCACTCC ACCATTTCTC
 701 AGGTACAGAA ATGAGCCAAA AAGGTTTTAT TTTCATACTA GTTGTTTTGT
 751 TGTTTGTGTT AAATTATCAA AATGAGCCTT TCTCTCTAGG TATGATGAGG
 801 ACGTCCATGA CCGAATTTGG ATTCCATTCT TAGATAACAA AAATTCCTTG
 851 TTAAGCACGG AACTCTCTGT TGATACAAGT AACTTCTACA ATGTGCCTCA
 901 AACTGTAGCG AAAACTGCTG CTGTCCCTTT AAATGCTACT CAGCCTCTGA
 951 AAATAAATTG GAGTCTCGAC GACATCACTT CACAGTCATA TATATACATG
1001 CATTTCGCTG AAATCGAGAA TCTTGAAGCT AATGAGACCA GAGAATTCAA
1051 TATTACTTAC AATGGTGGCG AAAATTGGTT CTCCTATTTT AGACCTCCAA
1101 AGTTTCGTAT AACAACTGTA TACAATCCAG CAGCTGTGAG TTCTCTAGAT
1151 GGGAATTTCA ACTTCACTTT CTCGATGACC GGTAACTCTA CTCATCCTCC
1201 TCTTATCAAC GGCCTTGAGA TTTATCAAGT TCTAGAGCTT CCACAGCTTG
1251 ATACATACCA AGATGAAGGT AAGTTAAGCA TGTTCTTAAA CCAATTCTTT
1301 TACCAAGAGT TCATGTCTTT GAAGTTTTTG AAATGTAATG ATTGATCAGT
1351 TTCCGCTATG ATGAATATCA AGACAATATA TGGATTGAGC AAAAGGTCTA
1401 GCTGGCAAGG AGATCCATGT GCTCCTGAGT TATATAGATG GGAAGGTTTA
1451 AACTGTAGTT ATCCAAACTT TGCGCCACCG CAGATCATAT CCTTGTATGT
1501 TTTGCTTGTT AATCTCACAA TTCTTTAGTT TCGAGTTTTT TTTCTCAAGT
1551 TCTAACTTTT GGACTCTCTA TTAGGAACTT GAGTGGAAGC AATTTGAGTG
1601 GTACCATAAC ATCTGATATA TCCAAGCTAA CACATTTGAG AGAACTGTAA
1651 GAATCCGAAA CTGTCACACA CTAATAAACT TAAAGTATAT GATATGGTGT
1701 ATTGTGTATA ACAAATTTAT TTTTTTCCTT TAATGCGCAG AGATTTATCA
1751 AACAATGACT TATCAGGAGA TATTCCATTT GTTTTTTCTG ATATGAAGAA
1801 TTTGACACTC ATGTGAGCTA CTAAATGACT AATATATTTA TCTTGGTTCT
1851 TGGTCGCTCT GCTCTTTGTG TGCTGTTCTC AAAGATTCAT TTTTGTCATT
1901 TGCAGAAACT TGAGTGGAAA CAAGAATCTA AATCGCTCAG TTCCAGAGAC
1951 TCTTCAGAAG AGGATAGATA ACAAATCTTT AACACTAATG TAAGATTTTC
2001 AGTGGATTCA GTCTCAAGCT TTTCAAGTCA CGGAAAGTAT TTCAGAATCC
2051 TATGAAACAG TGTCTAACCT TCTATTCGAT TCCACATCAC CTTTAATGAT
2101 TGCAGTAGAG ATGAAACCGG AAAAAATAGT ACAAATGTAG TTGCTATCGC
2151 AGCATCAGTG GCTAGCGTGT TTGCTGTGCT AGTTATCTTG GCTATCGTTT
2201 TTGTCGTCAT AAGGAAAAAA CAGAGAACTA ATGAAGGTAT GATCACTAGA
2251 ATAGGTCTTG AAAATAATGA AAATGAAAGT TGTCAGATTT ATACTCACTT
2301 CCTTTAGGTT TTACAGCTTC AGGACCCCGA TCATTCACTA CTGGCACGGT
2351 TAAGAGTGAT GCAAGATCAT CGAGTTCATC AATCATAACA AAGGAACGCA
2401 AGTTCACTTA TTCGGAGGTA CTAAAGATGA CTAAAAACTT TGAGAGAGTT
2451 CTTGGTAAAG GAGGGTTTGG AACAGTGTAT CATGGTAACT TGGATGATAC
2501 TCAAGTAGCT GTGAAAATGC TTTCTCATTC ATCAGCTCAA GGTTATAAAG
2551 AGTTCAAAGC AGAGGTACTT TAACAAGAAA TGGATATGTT TTTTTTTTTT
2601 TTAATAAGAA ATGGATATGT TAGTCTTAAT TGTTTTTAAA GTGCATTAGG
2651 TTCCTCAATC ATGAATGGTG ATTTTGTTCT TTCTTAGGTT GAACTTCTTT
2701 TAAGAGTTCA TCACAGACAT TTGGTGGGAC TTGTTGGTTA CTGTGATGAT
2751 GGAGACAACT TAGCTCTGAT CTATGAATAT ATGGAAAAAG GAGACCTGAG
```

Figure 5 – continued:

```
2801 GGAAAATATG TCAGGTAAGC ACTTTAATTT AGTTGAATCC ATCTCCTTAG
2851 ACAGTTTGAA ACATTCAAAG CCTGGTACAG GAAAACACAG TGTCAATGTC
2901 CTAAGCTGGG AAACAAGAAT GCAAATAGCT GTAGAGGCAG CACAAGGTGA
2951 ACTAAATTAT GACTTATATA CTTTTCATTC ACAACAATTT GTGTGGTAGT
3001 CTGAAAGCAA GATTGACATA AACAATAACT ATTTGTAACA GGATTGGAGT
3051 ATTTGCATAA CGGATGTAGG CCTCCTATGG TACATAGAGA TGTGAAACCA
3101 ACCAACATTT TATTAAATGA GCGGTCTCAA GCAAAACTAG CCGACTTTGG
3151 GCTATCGAGA TCTTTTCCTG TTGATGGTGA ATCTCATGTC ATGACAGTCG
3201 TTGCAGGAAC ACCTGGTTAC TTAGATCCTG AGTGAGTGAA TCAATCTGTT
3251 TCTTGTACTG AAATAAGTTA TGAAGAATTG GGAACTGTAA CCTCTCTTTA
3301 TGATACTCTT CTTTTCAGGT ATTACAGAAC AAACTGGCTA AGCGAGAAGA
3351 GTGATGTGTA CAGCTTTGGT GTAGTGCTTT TAGAGATAGT CACAAACCAG
3401 CCTGTGATGA ATAAAAACCG AGAGAGACCT CATATCAATG AATGGGTTAT
3451 GTTCATGCTT ACCAATGGGG ATATCAAGAG TATTGTCGAC CCGAAACTGA
3501 ATGAAGACTA TGACACAAAC GGTGTGTGGA AGGTTGTAGA GTTGGCTTTA
3551 GCTTGTGTAA ACCCGTCTTC AAGCCGTAGA CCGACAATGC CACACGTGGT
3601 GATGGAGCTA AACGAATGTC TTGCTTTGGA AATAGAAAGG AAACAAGGTA
3651 GTCAAGCGAC GTACATAAAG GAATCTGTTG AGTTTAGTCC ATCTTCTGCT
3701 TCTGATTTTT CCCCTTTAGC TAGGTAAAAG TCTTTGTGTT ATCAAGCTTT
3751 GTTGTTTATT ATAATCGATT GTTCATATTG AAATGTTTAA GATAGTTCTG
3801 TGAATTTTCT TCAAAATGTA TTAGCCTTTA TTATGTGTAA CATTCTTGGA
3851 TTCCAAGAAA TTTATATCTT T
```

Figure 6:

```
                          1                                                          60
RLK2-genomic      (1)   ATGAGGTTTTTGTCTTTCTTGATCTTCGTTTTCGCAGTTCTTGGATTGGTTCAAGCTCAA
   RLK2-cDNA      (1)   ATGAGGTTTTTGTCTTTCTTGATCTTCGTTTTCGCAGTTCTTGGATTGGTTCAAGCTCAA
                          61                                                        120
RLK2-genomic     (61)   GACCAATCAGGTTATTTACTCTGTTTCATGAAATCTTGATGTTTTGTTTCCTTTTCAGA
   RLK2-cDNA     (61)   GACCAATCAGG-------------------------------------------------
                          121                                                       180
RLK2-genomic    (121)   TCAACAAAACCTCTTAAAAGTTTGTTTTTTTCGATCATAAACAGGATTCATAAGCTTAGA
   RLK2-cDNA     (72)   ---------------------------------------------ATTCATAAGCTTAGA
                          181                                                       240
RLK2-genomic    (181)   TTGTGGTTTGGTGCCTACGGAAATTACTTATGTGGAAAAGTCGACGAATATAACATACAG
   RLK2-cDNA     (87)   TTGTGGTTTGGTGCCTACGGAAATTACTTATGTGGAAAAGTCGACGAATATAACATACAG
                          241                                                       300
RLK2-genomic    (241)   ATCAGACGCAACTTACATCGACAGTGGAGTTCCCGGGAAGATCAATGAAGTGTACAGAAC
   RLK2-cDNA    (147)   ATCAGACGCAACTTACATCGACAGTGGAGTTCCCGGGAAGATCAATGAAGTGTACAGAAC
                          301                                                       360
RLK2-genomic    (301)   ACAGTTTCAGCAACAAATTTGGGCCTTGAGAAGCTTCCCTGAGGGTCAAAGAAATTGTTA
   RLK2-cDNA    (207)   ACAGTTTCAGCAACAAATTTGGGCCTTGAGAAGCTTCCCTGAGGGTCAAAGAAATTGTTA
                          361                                                       420
RLK2-genomic    (361)   CAACTTCAGTCTCACCGCAAAACGTAAGTATCTAATCAGAGGAACCTTTATCTATGGGAA
   RLK2-cDNA    (267)   CAACTTCAGTCTCACCGCAAAACGTAAGTATCTAATCAGAGGAACCTTTATCTATGGGAA
                          421                                                       480
RLK2-genomic    (421)   TTATGACGGTTTGAATCAACTCCCGAGCTTTGATCTTTACATCGGTCCAAACAAATGGAC
   RLK2-cDNA    (327)   TTATGACGGTTTGAATCAACTCCCGAGCTTTGATCTTTACATCGGTCCAAACAAATGGAC
                          481                                                       540
RLK2-genomic    (481)   CTCTGTTTCGATCCCCGGAGTGAGAAATGGTTCAGTCTCCGAGATGATCCATGTCTTAAG
   RLK2-cDNA    (387)   CTCTGTTTCGATCCCCGGAGTGAGAAATGGTTCAGTCTCCGAGATGATCCATGTCTTAAG
                          541                                                       600
RLK2-genomic    (541)   ACAAGACCATCTTCAAATTTGTCTTGTGAAAACAGGAGAAACTACACCGTTTATTTCTTC
   RLK2-cDNA    (447)   ACAAGACCATCTTCAAATTTGTCTTGTGAAAACAGGAGAAACTACACCGTTTATTTCTTC
                          601                                                       660
RLK2-genomic    (601)   ATTGGAACTTCGTCCTTTGAACAATAATACATACGTCACAAAAAGTGGATCGCTTATTGT
   RLK2-cDNA    (507)   ATTGGAACTTCGTCCTTTGAACAATAATACATACGTCACAAAAAGTGGATCGCTTATTGT
                          661                                                       720
RLK2-genomic    (661)   GGTCGCAAGACTTTACTTTTCACCCACTCCACCATTTCTCAGGTACAGAAATGAGCCAAA
   RLK2-cDNA    (567)   GGTCGCAAGACTTTACTTTTCACCCACTCCACCATTTCTCAGGTA---------------
                          721                                                       780
RLK2-genomic    (721)   AAGGTTTTATTTTCATACTAGTTGTTTTGTTGTTTGTGTTAAATTATCAAAATGAGCCTT
   RLK2-cDNA    (612)   ------------------------------------------------------------
                          781                                                       840
RLK2-genomic    (781)   TCTCTCTAGGTATGATGAGGACGTCCATGACCGAATTTGGATTCCATTCTTAGATAACAA
   RLK2-cDNA    (612)   ------------TGATGAGGACGTCCATGACCGAATTTGGATTCCATTCTTAGATAACAA
                          841                                                       900
RLK2-genomic    (841)   AAATTCCTTGTTAAGCACGGAACTCTCTGTTGATACAAGTAACTTCTACAATGTGCCTCA
   RLK2-cDNA    (660)   AAATTCCTTGTTAAGCACGGAACTCTCTGTTGATACAAGTAACTTCTACAATGTGCCTCA
                          901                                                       960
RLK2-genomic    (901)   AACTGTAGCGAAAACTGCTGCTGTCCCTTTAAATGCTACTCAGCCTCTGAAAATAAATTG
   RLK2-cDNA    (720)   AACTGTAGCGAAAACTGCTGCTGTCCCTTTAAATGCTACTCAGCCTCTGAAAATAAATTG
                          961                                                      1020
RLK2-genomic    (961)   GAGTCTCGACGACATCACTTCACAGTCATATATATACATGCATTTCGCTGAAATCGAGAA
   RLK2-cDNA    (780)   GAGTCTCGACGACATCACTTCACAGTCATATATATACATGCATTTCGCTGAAATCGAGAA
                          1021                                                     1080
RLK2-genomic   (1021)   TCTTGAAGCTAATGAGACCAGAGAATTCAATATTACTTACAATGGTGGCGAAAATTGGTT
   RLK2-cDNA    (840)   TCTTGAAGCTAATGAGACCAGAGAATTCAATATTACTTACAATGGTGGCGAAAATTGGTT
                          1081                                                     1140
RLK2-genomic   (1081)   CTCCTATTTTAGACCTCCAAAGTTTCGTATAACAACTGTATACAATCCAGCAGCTGTGAG
   RLK2-cDNA    (900)   CTCCTATTTTAGACCTCCAAAGTTTCGTATAACAACTGTATACAATCCAGCAGCTGTGAG
                          1141                                                     1200
RLK2-genomic   (1141)   TTCTCTAGATGGGAATTTCAACTTCACTTTCTCGATGACCGGTAACTCTACTCATCCTCC
   RLK2-cDNA    (960)   TTCTCTAGATGGGAATTTCAACTTCACTTTCTCGATGACCGGTAACTCTACTCATCCTCC
                          1201                                                     1260
RLK2-genomic   (1201)   TCTTATCAACGGCCTTGAGATTTATCAAGTTCTAGAGCTTCCACAGCTTGATACATACCA
   RLK2-cDNA   (1020)   TCTTATCAACGGCCTTGAGATTTATCAAGTTCTAGAGCTTCCACAGCTTGATACATACCA
                          1261                                                     1320
RLK2-genomic   (1261)   AGATGAAGGTAAGTTAAGCATGTTCTTAAACCAATTCTTTTACCAAGAGTTCATGTCTTT
   RLK2-cDNA   (1080)   AGATGAAG----------------------------------------------------
                          1321                                                     1380
```

Figure 6 – continued:

```
RLK2-genomic  (1321) GAAGTTTTTGAAATGTAATGATTGATCAGTTTCCGCTATGATGAATATCAAGACAATATA
   RLK2-cDNA  (1088) -----------------------------TTTCCGCTATGATGAATATCAAGACAATATA
                     1381                                                    1440
RLK2-genomic  (1381) TGGATTGAGCAAAAGGTCTAGCTGGCAAGGAGATCCATGTGCTCCTGAGTTATATAGATG
   RLK2-cDNA  (1119) TGGATTGAGCAAAAGGTCTAGCTGGCAAGGAGATCCATGTGCTCCTGAGTTATATAGATG
                     1441                                                    1500
RLK2-genomic  (1441) GGAAGGTTTAAACTGTAGTTATCCAAACTTTGCGCCACCGCAGATCATATCCTTGTATGT
   RLK2-cDNA  (1179) GGAAGGTTTAAACTGTAGTTATCCAAACTTTGCGCCACCGCAGATCATATCCTTG-----
                     1501                                                    1560
RLK2-genomic  (1501) TTTGCTTGTTAATCTCACAATTCTTTAGTTTCGAGTTTTTTTTCTCAAGTTCTAACTTTT
   RLK2-cDNA  (1234) ------------------------------------------------------------
                     1561                                                    1620
RLK2-genomic  (1561) GGACTCTCTATTAGGAACTTGAGTGGAAGCAATTTGAGTGGTACCATAACATCTGATATA
   RLK2-cDNA  (1234) ---------------AACTTGAGTGGAAGCAATTTGAGTGGTACCATAACATCTGATATA
                     1621                                                    1680
RLK2-genomic  (1621) TCCAAGCTAACACATTTGAGAGAACTGTAAGAATCCGAAACTGTCACACACTAATAAACT
   RLK2-cDNA  (1279) TCCAAGCTAACACATTTGAGAGAACT----------------------------------
                     1681                                                    1740
RLK2-genomic  (1681) TAAAGTATATGATATGGTGTATTGTGTATAACAAATTTATTTTTTTCCTTTAATGCGCAG
   RLK2-cDNA  (1305) ------------------------------------------------------------
                     1741                                                    1800
RLK2-genomic  (1741) AGATTTATCAAACAATGACTTATCAGGAGATATTCCATTTGTTTTTTCTGATATGAAGAA
   RLK2-cDNA  (1305) AGATTTATCAAACAATGACTTATCAGGAGATATTCCATTTGTTTTTTCTGATATGAAGAA
                     1801                                                    1860
RLK2-genomic  (1801) TTTGACACTCATGTGAGCTACTAAATGACTAATATATTTATCTTGGTTCTTGGTCGCTCT
   RLK2-cDNA  (1365) TTTGACACTCAT------------------------------------------------
                     1861                                                    1920
RLK2-genomic  (1861) GCTCTTTGTGTGCTGTTCTCAAAGATTCATTTTTGTCATTTGCAGAAACTTGAGTGGAAA
   RLK2-cDNA  (1377) ---------------------------------------------AAACTTGAGTGGAAA
                     1921                                                    1980
RLK2-genomic  (1921) CAAGAATCTAAATCGCTCAGTTCCAGAGACTCTTCAGAAGAGGATAGATAACAAATCTTT
   RLK2-cDNA  (1392) CAAGAATCTAAATCGCTCAGTTCCAGAGACTCTTCAGAAGAGGATAGATAACAAATCTTT
                     1981                                                    2040
RLK2-genomic  (1981) AACACTAATGTAAGATTTTCAGTGGATTCAGTCTCAAGCTTTTCAAGTCACGGAAAGTAT
   RLK2-cDNA  (1452) AACACTAAT---------------------------------------------------
                     2041                                                    2100
RLK2-genomic  (2041) TTCAGAATCCTATGAAACAGTGTCTAACCTTCTATTCGATTCCACATCACCTTTAATGAT
   RLK2-cDNA  (1461) ------------------------------------------------------------
                     2101                                                    2160
RLK2-genomic  (2101) TGCAGTAGAGATGAAACCGGAAAAAATAGTACAAATGTAGTTGCTATCGCAGCATCAGTG
   RLK2-cDNA  (1461) -----TAGAGATGAAACCGGAAAAAATAGTACAAATGTAGTTGCTATCGCAGCATCAGTG
                     2161                                                    2220
RLK2-genomic  (2161) GCTAGCGTGTTTGCTGTGCTAGTTATCTTGGCTATCGTTTTTGTCGTCATAAGGAAAAAA
   RLK2-cDNA  (1516) GCTAGCGTGTTTGCTGTGCTAGTTATCTTGGCTATCGTTTTTGTCGTCATAAGGAAAAAA
                     2221                                                    2280
RLK2-genomic  (2221) CAGAGAACTAATGAAGGTATGATCACTAGAATAGGTCTTGAAAATAATGAAAATGAAAGT
   RLK2-cDNA  (1576) CAGAGAACTAATGAAG--------------------------------------------
                     2281                                                    2340
RLK2-genomic  (2281) TGTCAGATTTATACTCACTTCCTTTAGGTTTTACAGCTTCAGGACCCCGATCATTCACTA
   RLK2-cDNA  (1592) ------------------------------------CTTCAGGACCCCGATCATTCACTA
                     2341                                                    2400
RLK2-genomic  (2341) CTGGCACGGTTAAGAGTGATGCAAGATCATCGAGTTCATCAATCATAACAAAGGAACGCA
   RLK2-cDNA  (1616) CTGGCACGGTTAAGAGTGATGCAAGATCATCGAGTTCATCAATCATAACAAAGGAACGCA
                     2401                                                    2460
RLK2-genomic  (2401) AGTTCACTTATTCGGAGGTACTAAAGATGACTAAAAACTTTGAGAGAGTTCTTGGTAAAG
   RLK2-cDNA  (1676) AGTTCACTTATTCGGAGGTACTAAAGATGACTAAAAACTTTGAGAGAGTTCTTGGTAAAG
                     2461                                                    2520
RLK2-genomic  (2461) GAGGGTTTGGAACAGTGTATCATGGTAACTTGGATGATACTCAAGTAGCTGTGAAAATGC
   RLK2-cDNA  (1736) GAGGGTTTGGAACAGTGTATCATGGTAACTTGGATGATACTCAAGTAGCTGTGAAAATGC
                     2521                                                    2580
RLK2-genomic  (2521) TTTCTCATTCATCAGCTCAAGGTTATAAAGAGTTCAAAGCAGAGGTACTTTAACAAGAAA
   RLK2-cDNA  (1796) TTTCTCATTCATCAGCTCAAGGTTATAAAGAGTTCAAAGCAGAGGT--------------
                     2581                                                    2640
RLK2-genomic  (2581) TGGATATGTTTTTTTTTTTTTTAATAAGAAATGGATATGTTAGTCTTAATTGTTTTTAAA
   RLK2-cDNA  (1842) ------------------------------------------------------------
                     2641                                                    2700
```

Figure 6 - continued:

```
RLK2-genomic (2641) GTGCATTAGGTTCCTCAATCATGAATGGTGATTTTGTTCTTTCTTAGGTTGAACTTCTTT
   RLK2-cDNA (1842) -------------------------------------------------TGAACTTCTTT
                    2701                                                    2760
RLK2-genomic (2701) TAAGAGTTCATCACAGACATTTGGTGGGACTTGTTGGTTACTGTGATGATGGAGACAACT
   RLK2-cDNA (1853) TAAGAGTTCATCACAGACATTTGGTGGGACTTGTTGGTTACTGTGATGATGGAGACAACT
                    2761                                                    2820
RLK2-genomic (2761) TAGCTCTGATCTATGAATATATGGAAAAAGGAGACCTGAGGGAAAATATGTCAGGTAAGC
   RLK2-cDNA (1913) TAGCTCTGATCTATGAATATATGGAAAAAGGAGACCTGAGGGAAAATATGTCAG------
                    2821                                                    2880
RLK2-genomic (2821) ACTTTAATTTAGTTGAATCCATCTCCTTAGACAGTTTGAAACATTCAAAGCCTGGTACAG
   RLK2-cDNA (1967) ------------------------------------------------------------
                    2881                                                    2940
RLK2-genomic (2881) GAAAACACAGTGTCAATGTCCTAAGCTGGGAAACAAGAATGCAAATAGCTGTAGAGGCAG
   RLK2-cDNA (1967) GAAAACACAGTGTCAATGTCCTAAGCTGGGAAACAAGAATGCAAATAGCTGTAGAGGCAG
                    2941                                                    3000
RLK2-genomic (2941) CACAAGGTGAACTAAATTATGACTTATATACTTTTCATTCACAACAATTTGTGTGGTAGT
   RLK2-cDNA (2027) CACAAGG-----------------------------------------------------
                    3001                                                    3060
RLK2-genomic (3001) CTGAAAGCAAGATTGACATAAACAATAACTATTTGTAACAGGATTGGAGTATTTGCATAA
   RLK2-cDNA (2034) ------------------------------------------ATTGGAGTATTTGCATAA
                    3061                                                    3120
RLK2-genomic (3061) CGGATGTAGGCCTCCTATGGTACATAGAGATGTGAAACCAACCAACATTTTATTAAATGA
   RLK2-cDNA (2052) CGGATGTAGGCCTCCTATGGTACATAGAGATGTGAAACCAACCAACATTTTATTAAATGA
                    3121                                                    3180
RLK2-genomic (3121) GCGGTCTCAAGCAAAACTAGCCGACTTTGGGCTATCGAGATCTTTTCCTGTTGATGGTGA
   RLK2-cDNA (2112) GCGGTCTCAAGCAAAACTAGCCGACTTTGGGCTATCGAGATCTTTTCCTGTTGATGGTGA
                    3181                                                    3240
RLK2-genomic (3181) ATCTCATGTCATGACAGTCGTTGCAGGAACACCTGGTTACTTAGATCCTGAGTGAGTGAA
   RLK2-cDNA (2172) ATCTCATGTCATGACAGTCGTTGCAGGAACACCTGGTTACTTAGATCCTGAGT-------
                    3241                                                    3300
RLK2-genomic (3241) TCAATCTGTTTCTTGTACTGAAATAAGTTATGAAGAATTGGGAACTGTAACCTCTCTTTA
   RLK2-cDNA (2225) ------------------------------------------------------------
                    3301                                                    3360
RLK2-genomic (3301) TGATACTCTTCTTTTCAGGTATTACAGAACAAACTGGCTAAGCGAGAAGAGTGATGTGTA
   RLK2-cDNA (2225) --------------------ATTACAGAACAAACTGGCTAAGCGAGAAGAGTGATGTGTA
                    3361                                                    3420
RLK2-genomic (3361) CAGCTTTGGTGTAGTGCTTTTAGAGATAGTCACAAACCAGCCTGTGATGAATAAAAACCG
   RLK2-cDNA (2265) CAGCTTTGGTGTAGTGCTTTTAGAGATAGTCACAAACCAGCCTGTGATGAATAAAAACCG
                    3421                                                    3480
RLK2-genomic (3421) AGAGAGACCTCATATCAATGAATGGGTTATGTTCATGCTTACCAATGGGGATATCAAGAG
   RLK2-cDNA (2325) AGAGAGACCTCATATCAATGAATGGGTTATGTTCATGCTTACCAATGGGGATATCAAGAG
                    3481                                                    3540
RLK2-genomic (3481) TATTGTCGACCCGAAACTGAATGAAGACTATGACACAAACGGTGTGTGGAAGGTTGTAGA
   RLK2-cDNA (2385) TATTGTCGACCCGAAACTGAATGAAGACTATGACACAAACGGTGTGTGGAAGGTTGTAGA
                    3541                                                    3600
RLK2-genomic (3541) GTTGGCTTTAGCTTGTGTAAACCCGTCTTCAAGCCGTAGACCGACAATGCCACACGTGGT
   RLK2-cDNA (2445) GTTGGCTTTAGCTTGTGTAAACCCGTCTTCAAGCCGTAGACCGACAATGCCACACGTGGT
                    3601                                                    3660
RLK2-genomic (3601) GATGGAGCTAAACGAATGTCTTGCTTTGGAAATAGAAAGGAAACAAGGTAGTCAAGCGAC
   RLK2-cDNA (2505) GATGGAGCTAAACGAATGTCTTGCTTTGGAAATAGAAAGGAAACAAGGTAGTCAAGCGAC
                    3661                                                    3720
RLK2-genomic (3661) GTACATAAAGGAATCTGTTGAGTTTAGTCCATCTTCTGCTTCTGATTTTTCCCCTTTAGC
   RLK2-cDNA (2565) GTACATAAAGGAATCTGTTGAGTTTAGTCCATCTTCTGCTTCTGATTTTTCCCCTTTAGC
                    3721                                                    3780
RLK2-genomic (3721) TAGGTAAAAGTCTTTGTGTTATCAAGCTTTGTTGTTTATTATAATCGATTGTTCATATTG
   RLK2-cDNA (2625) TAGGTAA-----------------------------------------------------
                    3781                                                    3840
RLK2-genomic (3781) AAATGTTTAAGATAGTTCTGTGAATTTTCTTCAAAATGTATTAGCCTTTATTATGTGTAA
   RLK2-cDNA (2632) ------------------------------------------------------------
                    3841                           3871
RLK2-genomic (3841) CATTCTTGGATTCCAAGAAATTTATATCTTT
   RLK2-cDNA (2632) -------------------------------
```

Figure 7:

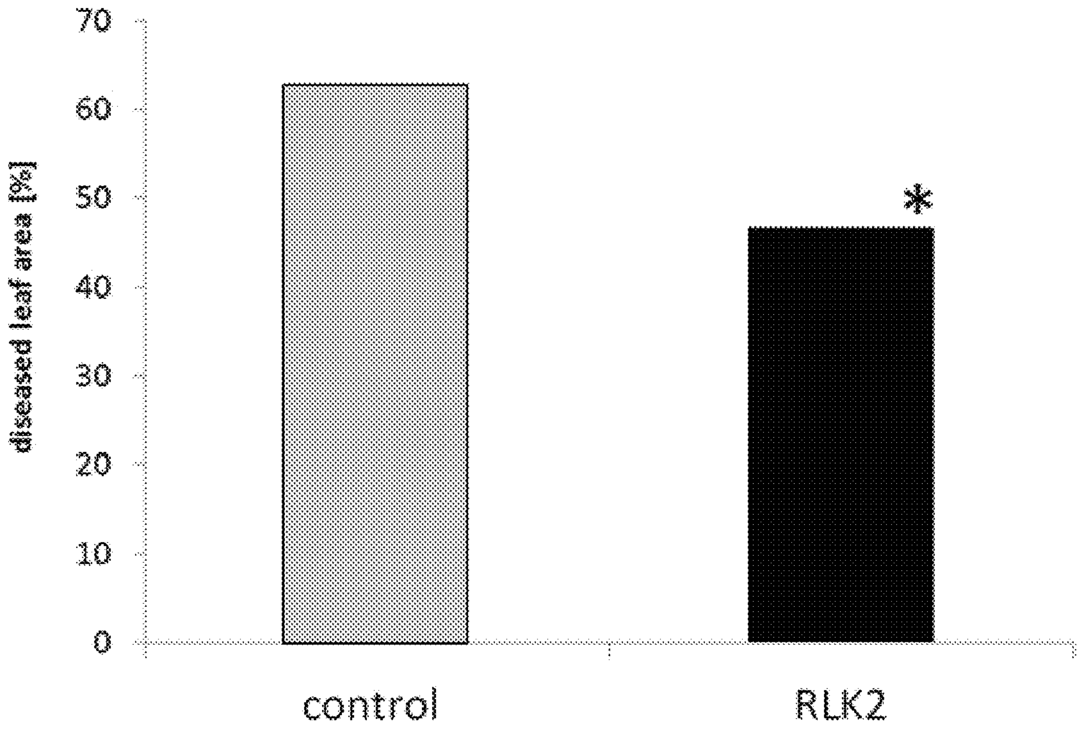

Figure 8:

| SEQ ID NO: | Description of the sequence listing |
|---|---|
| SEQ ID NO:1 | Nucleotide sequence RLK2 cDNA; Arabidopsis thaliana |
| SEQ ID NO:2 | Amino acid sequence RLK2; Arabidopsis thaliana |
| SEQ ID NO:3 | Nucleotide sequence RLK2 genomic sequence; Arabidopsis thaliana |
| SEQ ID NO:4 | Nucleotide sequence RLK2; based on SEQ ID NO: 1; codon optimized for Glycine max |
| SEQ ID NO:5 | Nucleotide sequence RLK2, variant 1 |
| SEQ ID NO:6 | Nucleotide sequence RLK2, variant 2 |
| SEQ ID NO:7 | Nucleotide sequence RLK2, variant 3 |
| SEQ ID NO:8 | Nucleotide sequence RLK2, variant 4 |
| SEQ ID NO:9 | Nucleotide sequence RLK2, variant 5 |
| SEQ ID NO:10 | Nucleotide sequence RLK2, variant 6 |
| SEQ ID NO:11 | Nucleotide sequence RLK2, variant 7 |
| SEQ ID NO:12 | Nucleotide sequence RLK2, variant 8 |
| SEQ ID NO:13 | Nucleotide sequence RLK2, variant 9 |
| SEQ ID NO:14 | Nucleotide sequence RLK2, variant 10 |

Figure 8 – continued:

| SEQ ID NO: | Description of the sequence listing |
|---|---|
| SEQ ID NO:15 | Nucleotide sequence RLK2, variant 11 |
| SEQ ID NO:16 | Nucleotide sequence RLK2, variant 12 |
| SEQ ID NO:17 | Nucleotide sequence RLK2, variant 13 |
| SEQ ID NO:18 | Nucleotide sequence RLK2, variant 14 |
| SEQ ID NO:19 | Nucleotide sequence RLK2, variant 15 |
| SEQ ID NO:20 | Nucleotide sequence RLK2, variant 16 |
| SEQ ID NO:21 | Nucleotide sequence RLK2, variant 17 |
| SEQ ID NO:22 | Amino acid sequence RLK2, variant 17 |
| SEQ ID NO:23 | Nucleotide sequence RLK2, variant 18 |
| SEQ ID NO:24 | Amino acid sequence RLK2, variant 18 |
| SEQ ID NO:25 | Nucleotide sequence RLK2, variant 19 |
| SEQ ID NO:26 | Amino acid sequence RLK2, variant 19 |
| SEQ ID NO:27 | Nucleotide sequence RLK2, variant 20 |
| SEQ ID NO:28 | Amino acid sequence RLK2, variant 20 |
| SEQ ID NO:29 | Nucleotide sequence RLK2, variant 21 |
| SEQ ID NO:30 | Amino acid sequence RLK2, variant 21 |
| SEQ ID NO:31 | Nucleotide sequence RLK2, variant 22 |
| SEQ ID NO:32 | Amino acid sequence RLK2, variant 22 |
| SEQ ID NO:33 | Nucleotide sequence RLK2, variant 23 |
| SEQ ID NO:34 | Amino acid sequence RLK2, variant 23 |
| SEQ ID NO:35 | Nucleotide sequence RLK2, variant 24 |
| SEQ ID NO:36 | Amino acid sequence RLK2, variant 24 |

SEQUENCE LISTING

```
<160> NUMBER OF SEQ ID NOS: 36

<210> SEQ ID NO 1
<211> LENGTH: 2631
<212> TYPE: DNA
<213> ORGANISM: Arabidopsis thaliana
<220> FEATURE:
<221> NAME/KEY: source
<222> LOCATION: (1)..(2631)
<223> OTHER INFORMATION: /organism="Arabidopsis thaliana"
      /mol_type="unassigned DNA"

<400> SEQUENCE: 1

atgaggtttt tgtctttctt gatcttcgtt ttcgcagttc ttggattggt tcaagctcaa     60

gaccaatcag gattcataag cttagattgt ggtttggtgc ctacggaaat tacttatgtg    120

gaaaagtcga cgaatataac atacagatca gacgcaactt acatcgacag tggagttccc    180

gggaagatca atgaagtgta cagaacacag tttcagcaac aaatttgggc cttgagaagc    240

ttccctgagg gtcaaagaaa ttgttacaac ttcagtctca ccgcaaaacg taagtatcta    300

atcagaggaa cctttatcta tgggaattat gacggtttga atcaactccc gagctttgat    360

ctttacatcg gtccaaacaa atggacctct gtttcgatcc ccggagtgag aaatggttca    420

gtctccgaga tgatccatgt cttaagacaa gaccatcttc aaatttgtct tgtgaaaaca    480

ggagaaacta caccgtttat ttcttcattg gaacttcgtc ctttgaacaa taatacatac    540

gtcacaaaaa gtggatcgct tattgtggtc gcaagacttt acttttcacc cactccacca    600

tttctcaggt atgatgagga cgtccatgac cgaatttgga ttccattctt agataacaaa    660

aattccttgt taagcacgga actctctgtt gatacaagta acttctacaa tgtgcctcaa    720

actgtagcga aaactgctgc tgtcccttta aatgctactc agcctctgaa aataaattgg    780

agtctcgacg acatcacttc acagtcatat atatacatgc atttcgctga aatcgagaat    840

cttgaagcta atgagaccag agaattcaat attacttaca atggtggcga aaattggttc    900
```

```
tcctatttta gacctccaaa gtttcgtata acaactgtat acaatccagc agctgtgagt    960
tctctagatg ggaatttcaa cttcactttc tcgatgaccg gtaactctac tcatcctcct   1020
cttatcaacg gccttgagat ttatcaagtt ctagagcttc cacagcttga tacataccaa   1080
gatgaagttt ccgctatgat gaatatcaag acaatatatg gattgagcaa aaggtctagc   1140
tggcaaggag atccatgtgc tcctgagtta tatagatggg aaggtttaaa ctgtagttat   1200
ccaaactttg cgccaccgca gatcatatcc ttgaacttga gtggaagcaa tttgagtggt   1260
accataacat ctgatatatc caagctaaca catttgagag aactagattt atcaaacaat   1320
gacttatcag gagatattcc atttgttttt tctgatatga agaatttgac actcataaac   1380
ttgagtggaa acaagaatct aaatcgctca gttccagaga ctcttcagaa gaggatagat   1440
aacaaatctt taacactaat tagagatgaa accggaaaaa atagtacaaa tgtagttgct   1500
atcgcagcat cagtggctag cgtgtttgct gtgctagtta tcttggctat cgtttttgtc   1560
gtcataagga aaaaacagag aactaatgaa gcttcaggac cccgatcatt cactactggc   1620
acggttaaga gtgatgcaag atcatcgagt tcatcaatca taacaaagga acgcaagttc   1680
acttattcgg aggtactaaa gatgactaaa aactttgaga gagttcttgg taaaggaggg   1740
tttggaacag tgtatcatgg taacttggat gatactcaag tagctgtgaa aatgctttct   1800
cattcatcag ctcaaggtta taaagagttc aaagcagagg ttgaacttct tttaagagtt   1860
catcacagac atttggtggg acttgttggt tactgtgatg atggagacaa cttagctctg   1920
atctatgaat atatggaaaa aggagacctg agggaaaata tgtcaggaaa acacagtgtc   1980
aatgtcctaa gctgggaaac aagaatgcaa atagctgtag aggcagcaca aggattggag   2040
tatttgcata acggatgtag gcctcctatg gtacatagag atgtgaaacc aaccaacatt   2100
ttattaaatg agcggtctca agcaaaacta gccgactttg ggctatcgag atcttttcct   2160
gttgatggtg aatctcatgt catgacagtc gttgcaggaa cacctggtta cttagatcct   2220
gagtattaca gaacaaactg gctaagcgag aagagtgatg tgtacagctt tggtgtagtg   2280
cttttagaga tagtcacaaa ccagcctgtg atgaataaaa accgagagag acctcatatc   2340
aatgaatggg ttatgttcat gcttaccaat ggggatatca agagtattgt cgacccgaaa   2400
ctgaatgaag actatgacac aaacggtgtg tggaaggttg tagagttggc tttagcttgt   2460
gtaaacccgt cttcaagccg tagaccgaca atgccacacg tggtgatgga gctaaacgaa   2520
tgtcttgctt tggaaataga aaggaaacaa ggtagtcaag cgacgtacat aaaggaatct   2580
gttgagttta gtccatcttc tgcttctgat tttccccctt tagctaggta a            2631
```

<210> SEQ ID NO 2
<211> LENGTH: 876
<212> TYPE: PRT
<213> ORGANISM: Arabidopsis thaliana

<400> SEQUENCE: 2

```
Met Arg Phe Leu Ser Phe Leu Ile Phe Val Phe Ala Val Leu Gly Leu
1               5                   10                  15

Val Gln Ala Gln Asp Gln Ser Gly Phe Ile Ser Leu Asp Cys Gly Leu
            20                  25                  30

Val Pro Thr Glu Ile Thr Tyr Val Glu Lys Ser Thr Asn Ile Thr Tyr
        35                  40                  45

Arg Ser Asp Ala Thr Tyr Ile Asp Ser Gly Val Pro Gly Lys Ile Asn
    50                  55                  60
```

-continued

```
Glu Val Tyr Arg Thr Gln Phe Gln Gln Gln Ile Trp Ala Leu Arg Ser
65                  70                  75                  80

Phe Pro Glu Gly Gln Arg Asn Cys Tyr Asn Phe Ser Leu Thr Ala Lys
                85                  90                  95

Arg Lys Tyr Leu Ile Arg Gly Thr Phe Ile Tyr Gly Asn Tyr Asp Gly
            100                 105                 110

Leu Asn Gln Leu Pro Ser Phe Asp Leu Tyr Ile Gly Pro Asn Lys Trp
        115                 120                 125

Thr Ser Val Ser Ile Pro Gly Val Arg Asn Gly Ser Val Ser Glu Met
    130                 135                 140

Ile His Val Leu Arg Gln Asp His Leu Gln Ile Cys Leu Val Lys Thr
145                 150                 155                 160

Gly Glu Thr Thr Pro Phe Ile Ser Ser Leu Glu Leu Arg Pro Leu Asn
                165                 170                 175

Asn Asn Thr Tyr Val Thr Lys Ser Gly Ser Leu Ile Val Val Ala Arg
            180                 185                 190

Leu Tyr Phe Ser Pro Thr Pro Pro Phe Leu Arg Tyr Asp Glu Asp Val
        195                 200                 205

His Asp Arg Ile Trp Ile Pro Phe Leu Asp Asn Lys Asn Ser Leu Leu
    210                 215                 220

Ser Thr Glu Leu Ser Val Asp Thr Ser Asn Phe Tyr Asn Val Pro Gln
225                 230                 235                 240

Thr Val Ala Lys Thr Ala Ala Val Pro Leu Asn Ala Thr Gln Pro Leu
                245                 250                 255

Lys Ile Asn Trp Ser Leu Asp Asp Ile Thr Ser Gln Ser Tyr Ile Tyr
            260                 265                 270

Met His Phe Ala Glu Ile Glu Asn Leu Glu Ala Asn Glu Thr Arg Glu
        275                 280                 285

Phe Asn Ile Thr Tyr Asn Gly Gly Glu Asn Trp Phe Ser Tyr Phe Arg
    290                 295                 300

Pro Pro Lys Phe Arg Ile Thr Thr Val Tyr Asn Pro Ala Ala Val Ser
305                 310                 315                 320

Ser Leu Asp Gly Asn Phe Asn Phe Thr Phe Ser Met Thr Gly Asn Ser
                325                 330                 335

Thr His Pro Pro Leu Ile Asn Gly Leu Glu Ile Tyr Gln Val Leu Glu
            340                 345                 350

Leu Pro Gln Leu Asp Thr Tyr Gln Asp Glu Val Ser Ala Met Met Asn
        355                 360                 365

Ile Lys Thr Ile Tyr Gly Leu Ser Lys Arg Ser Ser Trp Gln Gly Asp
    370                 375                 380

Pro Cys Ala Pro Glu Leu Tyr Arg Trp Glu Gly Leu Asn Cys Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
```

```
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560

Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
            580                 585                 590

Gln Val Ala Val Lys Met Leu Ser His Ser Ser Ala Gln Gly Tyr Lys
        595                 600                 605

Glu Phe Lys Ala Glu Val Glu Leu Leu Leu Arg Val His His Arg His
    610                 615                 620

Leu Val Gly Leu Val Gly Tyr Cys Asp Asp Gly Asp Asn Leu Ala Leu
625                 630                 635                 640

Ile Tyr Glu Tyr Met Glu Lys Gly Asp Leu Arg Glu Asn Met Ser Gly
                645                 650                 655

Lys His Ser Val Asn Val Leu Ser Trp Glu Thr Arg Met Gln Ile Ala
            660                 665                 670

Val Glu Ala Ala Gln Gly Leu Glu Tyr Leu His Asn Gly Cys Arg Pro
        675                 680                 685

Pro Met Val His Arg Asp Val Lys Pro Thr Asn Ile Leu Leu Asn Glu
    690                 695                 700

Arg Ser Gln Ala Lys Leu Ala Asp Phe Gly Leu Ser Arg Ser Phe Pro
705                 710                 715                 720

Val Asp Gly Glu Ser His Val Met Thr Val Val Ala Gly Thr Pro Gly
                725                 730                 735

Tyr Leu Asp Pro Glu Tyr Tyr Arg Thr Asn Trp Leu Ser Glu Lys Ser
            740                 745                 750

Asp Val Tyr Ser Phe Gly Val Val Leu Leu Glu Ile Val Thr Asn Gln
        755                 760                 765

Pro Val Met Asn Lys Asn Arg Glu Arg Pro His Ile Asn Glu Trp Val
    770                 775                 780

Met Phe Met Leu Thr Asn Gly Asp Ile Lys Ser Ile Val Asp Pro Lys
785                 790                 795                 800

Leu Asn Glu Asp Tyr Asp Thr Asn Gly Val Trp Lys Val Val Glu Leu
                805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Ser Pro Leu Ala Arg
865                 870                 875


<210> SEQ ID NO 3
<211> LENGTH: 3871
<212> TYPE: DNA
<213> ORGANISM: Arabidopsis thaliana
```

<220> FEATURE:
<221> NAME/KEY: source
<222> LOCATION: (1)..(3871)
<223> OTHER INFORMATION: /organism="Arabidopsis thaliana"
/mol_type="unassigned DNA"

<400> SEQUENCE: 3

```
atgaggtttt tgtctttctt gatcttcgtt ttcgcagttc ttggattggt tcaagctcaa      60

gaccaatcag gttatttact ctgttttcat gaaatcttga tgttttgttt ccttttcaga     120

tcaacaaaac ctcttaaaag tttgtttttt tcgatcataa acaggattca taagcttaga     180

ttgtggtttg gtgcctacgg aaattactta tgtggaaaag tcgacgaata taacatacag     240

atcagacgca acttacatcg acagtggagt tcccgggaag atcaatgaag tgtacagaac     300

acagtttcag caacaaattt gggccttgag aagcttccct gagggtcaaa gaaattgtta     360

caacttcagt ctcaccgcaa aacgtaagta tctaatcaga ggaaccttta tctatgggaa     420

ttatgacggt ttgaatcaac tcccgagctt tgatctttac atcggtccaa acaaatggac     480

ctctgtttcg atccccggag tgagaaatgg ttcagtctcc gagatgatcc atgtcttaag     540

acaagaccat cttcaaattt gtcttgtgaa aacaggagaa actacaccgt ttatttcttc     600

attggaactt cgtcctttga acaataatac atacgtcaca aaaagtggat cgcttattgt     660

ggtcgcaaga ctttactttt cacccactcc accatttctc aggtacagaa atgagccaaa     720

aaggttttat tttcatacta gttgttttgt tgtttgtgtt aaattatcaa aatgagcctt     780

tctctctagg tatgatgagg acgtccatga ccgaatttgg attccattct tagataacaa     840

aaattccttg ttaagcacgg aactctctgt tgatacaagt aacttctaca atgtgcctca     900

aactgtagcg aaaactgctg ctgtcccttt aaatgctact cagcctctga aaataaattg     960

gagtctcgac gacatcactt cacagtcata tatatacatg catttcgctg aaatcgagaa    1020

tcttgaagct aatgagacca gagaattcaa tattacttac aatggtggcg aaaattggtt    1080

ctcctatttt agacctccaa agtttcgtat aacaactgta tacaatccag cagctgtgag    1140

ttctctagat gggaatttca acttcacttt ctcgatgacc ggtaactcta ctcatcctcc    1200

tcttatcaac ggccttgaga tttatcaagt tctagagctt ccacagcttg atacatacca    1260

agatgaaggt aagttaagca tgttcttaaa ccaattcttt taccaagagt tcatgtcttt    1320

gaagtttttg aaatgtaatg attgatcagt ttccgctatg atgaatatca agacaatata    1380

tggattgagc aaaaggtcta gctggcaagg agatccatgt gctcctgagt tatatagatg    1440

ggaaggttta aactgtagtt atccaaactt tgcgccaccg cagatcatat ccttgtatgt    1500

tttgcttgtt aatctcacaa ttctttagtt tcgagttttt tttctcaagt tctaactttt    1560

ggactctcta ttaggaactt gagtggaagc aatttgagtg gtaccataac atctgatata    1620

tccaagctaa cacatttgag agaactgtaa gaatccgaaa ctgtcacaca ctaataaact    1680

taaagtatat gatatggtgt attgtgtata acaaatttat ttttttcctt taatgcgcag    1740

agatttatca aacaatgact tatcaggaga tattccattt gttttttctg atatgaagaa    1800

tttgacactc atgtgagcta ctaaatgact aatatattta tcttggttct tggtcgctct    1860

gctctttgtg tgctgttctc aaagattcat ttttgtcatt tgcagaaact tgagtggaaa    1920

caagaatcta aatcgctcag ttccagagac tcttcagaag aggatagata acaaatcttt    1980

aacactaatg taagattttc agtggattca gtctcaagct tttcaagtca cggaaagtat    2040

ttcagaatcc tatgaaacag tgtctaacct tctattcgat tccacatcac ctttaatgat    2100

tgcagtagag atgaaaccgg aaaaaatagt acaaatgtag ttgctatcgc agcatcagtg    2160
```

-continued

```
gctagcgtgt ttgctgtgct agttatcttg gctatcgttt ttgtcgtcat aaggaaaaaa   2220

cagagaacta atgaaggtat gatcactaga ataggtcttg aaaataatga aaatgaaagt   2280

tgtcagattt atactcactt cctttaggtt ttacagcttc aggaccccga tcattcacta   2340

ctggcacggt taagagtgat gcaagatcat cgagttcatc aatcataaca aaggaacgca   2400

agttcactta ttcggaggta ctaaagatga ctaaaaactt tgagagagtt cttggtaaag   2460

gagggtttgg aacagtgtat catggtaact tggatgatac tcaagtagct gtgaaaatgc   2520

tttctcattc atcagctcaa ggttataaag agttcaaagc agaggtactt taacaagaaa   2580

tggatatgtt tttttttttt ttaataagaa atggatatgt tagtcttaat tgtttttaaa   2640

gtgcattagg ttcctcaatc atgaatggtg attttgttct ttcttaggtt gaacttcttt   2700

taagagttca tcacagacat ttggtgggac ttgttggtta ctgtgatgat ggagacaact   2760

tagctctgat ctatgaatat atggaaaaag gagacctgag ggaaaatatg tcaggtaagc   2820

actttaattt agttgaatcc atctccttag acagtttgaa acattcaaag cctggtacag   2880

gaaaacacag tgtcaatgtc ctaagctggg aaacaagaat gcaaatagct gtagaggcag   2940

cacaaggtga actaaattat gacttatata cttttcattc acaacaattt gtgtggtagt   3000

ctgaaagcaa gattgacata aacaataact atttgtaaca ggattggagt atttgcataa   3060

cggatgtagg cctcctatgg tacatagaga tgtgaaacca accaacattt tattaaatga   3120

gcggtctcaa gcaaaactag ccgactttgg gctatcgaga tcttttcctg ttgatggtga   3180

atctcatgtc atgacagtcg ttgcaggaac acctggttac ttagatcctg agtgagtgaa   3240

tcaatctgtt tcttgtactg aaataagtta tgaagaattg ggaactgtaa cctctcttta   3300

tgatactctt cttttcaggt attacagaac aaactggcta agcgagaaga gtgatgtgta   3360

cagctttggt gtagtgcttt tagagatagt cacaaaccag cctgtgatga ataaaaaccg   3420

agagagacct catatcaatg aatgggttat gttcatgctt accaatgggg atatcaagag   3480

tattgtcgac ccgaaactga atgaagacta tgacacaaac ggtgtgtgga aggttgtaga   3540

gttggcttta gcttgtgtaa acccgtcttc aagccgtaga ccgacaatgc cacacgtggt   3600

gatggagcta aacgaatgtc ttgctttgga aatagaaagg aaacaaggta gtcaagcgac   3660

gtacataaag gaatctgttg agtttagtcc atcttctgct tctgattttt cccctttagc   3720

taggtaaaag tctttgtgtt atcaagcttt gttgtttatt ataatcgatt gttcatattg   3780

aaatgtttaa gatagttctg tgaattttct tcaaaatgta ttagccttta ttatgtgtaa   3840

cattcttgga ttccaagaaa tttatatctt t                                  3871
```

<210> SEQ ID NO 4
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence" /note="Codon optimized RLK2 sequence" /mol_type="unassigned DNA"

<400> SEQUENCE: 4

```
atgagattcc ttagtttctt aatcttcgtg ttcgccgtgc taggcctagt tcaagctcaa     60

gatcagtcag gctttattag cctagattgc ggactagtgc ctaccgagat tacctacgtc    120

gagaagtcta ctaatatcac ctataggtca gacgctacct atatcgatag cggcgtgccc    180
```

-continued

```
ggtaagatta acgaagtcta taggactcag tttcagcagc agatctgggc ccttagatct    240
ttcccagagg gtcagaggaa ctgctataac tttagcctaa ccgctaagcg taagtaccta    300
attaggggca cctttatcta cggtaactac gacggcctta atcagctacc tagcttcgac    360
ctctatatcg gccctaacaa gtggactagc gttagtattc caggcgttag gaacggctca    420
gttagcgaga tgattcacgt gctaaggcag gatcaccttc agatctgcct agttaagacc    480
ggtgagacta ccccctttat tagctcacta gagcttaggc cccttaacaa caacacctac    540
gtgactaagt caggctcact aatagtggtg gctaggctct actttagccc taccccacct    600
ttccttaggt acgacgaaga tgttcacgat aggatctgga tacccttcct agataacaag    660
aactcactac ttagcaccga gcttagcgtg gacactagta acttctataa cgtgccacag    720
accgtggcta agactgctgc tgttccactt aacgctactc agccccttaa gattaactgg    780
tcactagacg atatcactag tcagtcctat atctatatgc acttcgccga gatagagaac    840
ctagaggcta acgagactag agagtttaat atcacttata acggcggcga gaactggttt    900
agctacttta ggccacctaa gtttaggatc actaccgtct ataacccagc cgccgttagt    960
tcactagacg gtaactttaa cttcaccttt agtatgaccg gtaactctac tcaccccccc   1020
cttattaacg gcctagagat ctatcaggtg ctagagctac ctcagctaga cacctatcag   1080
gacgaagtta gcgctatgat gaatattaag actatctacg gccttagtaa gcgctctagc   1140
tggcaaggtg atccttgcgc tccagaactc tataggtggg aaggccttaa ctgtagctac   1200
cctaacttcg cccctcctca gattatctca cttaacctta gcggctctaa ccttagtggc   1260
actattacta gcgatattag taagctaact caccttaggg aactagacct tagtaacaac   1320
gaccttagcg gcgatatccc cttcgtgttt agcgatatga agaacctaac cctgattaac   1380
ctaagcggta acaagaacct taatagatca gtgcccgaga ctcttcagaa gaggatagat   1440
aacaagtcac taaccttaat tagggacgag actggtaaga actctactaa cgtggtggct   1500
atagctgcta gtgtcgctag cgttttcgct gtgctagtga tcctagctat agtgttcgtg   1560
gtgattagga agaagcagcg cactaacgaa gctagcggac ctagatcttt cactaccggc   1620
actgttaagt cagacgctag gtctagctct agctctatta tcactaagga acgtaagttc   1680
acctatagcg aagtgcttaa gatgactaag aacttcgagc gcgtgctagg taagggcgga   1740
ttcggaactg tttatcacgg taacctagac gacactcagg tggccgttaa gatgcttagt   1800
cactctagcg ctcagggcta taaggagttt aaggccgagg ttgagctact acttagggtt   1860
caccaccgtc acctagtggg actagttggt tattgcgacg acggtgataa cctagcccta   1920
atctacgagt atatggaaaa gggcgacctt agggagaata tgagcggtaa gcactcagtt   1980
aacgtgctaa gctgggagac taggatgcag atagctgttg aagctgctca gggactagag   2040
taccttcaca acggttgtag gccacctatg gttcacaggg acgttaagcc tactaatatc   2100
ctacttaacg agcgtagtca ggctaagcta gctgacttcg gccttagtag atcattccca   2160
gttgacggtg agtctcacgt tatgaccgtt gttgctggaa ccccaggtta cctagaccca   2220
gagtactata ggactaactg gcttagcgag aagtcagacg tctactcttt cggagtggtg   2280
ctactagaga tagtgactaa tcagcccgtg atgaacaaga atagagagcg ccctcacatt   2340
aacgagtggg tgatgtttat gctaactaac ggcgatatta agtctatagt ggaccctaag   2400
cttaacgagg actacgacac taacggcgtt tggaaggttg tggaactagc tctagcctgc   2460
gttaacccta gctctagtag aaggcctact atgcctcacg tggtgatgga acttaacgag   2520
```

```
tgcctagctc tagagataga gcgtaagcaa ggtagtcaag ctacctatat taaggaatca   2580

gtcgagttta gccctagctc agctagcgac tttagtccac tagctaggtg a            2631


<210> SEQ ID NO 5
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
      /note="Nucleotide sequence RLK2, variant 1" /mol_type="unassigned
      DNA"

<400> SEQUENCE: 5

atgcgtttca tgtcatttat gatttttgtc tttgccgtgc tagggatggt acaggcccag     60

gatcagagcg gttttatctc actcgactgc gggttggtcc caaccgagat aacctacgtc    120

gagaaatcga ccaacatcac gtatcgctcc gatgcgacgt atattgatag cggggtccca    180

ggtaaaataa acgaggtcta tcggacccaa ttccaacaac agatctgggc aatgcggtca    240

tttccggaag gtcaaaggaa ctgctataat ttttcattga cggctaagcg gaaataccta    300

attaggggga ccttcattta cggtaactac gatggaatga accagctgcc ttcattcgac    360

ttatatatag gcccgaataa gtggaccagt gtctctattc ctggcgtacg taatggatcc    420

gtatcagaaa tgatccacgt tttgcgccag gatcacttgc agatctgctt ggttaagact    480

ggggagacaa ctccattcat atcctcgatg gagctcaggc ccatgaataa caacacctat    540

gttacgaagt caggttcact gatcgtcgtt gcccgcctct atttctctcc aacacctccg    600

ttccttcgct acgacgaaga tgttcacgat aggatttgga taccctttct cgataataag    660

aactcgatgc tcagtactga gctttcggtg gacacctcaa atttttataa cgtaccacag    720

acggttgcca agactgcggc cgtgccatta aacgcaaccc aaccgatgaa gattaactgg    780

agtttggatg atattacatc ccaatcctac atttatatgc actttgcgga gattgaaaac    840

ctggaggcga acgaaaccag ggagtttaac atcacgtata atggaggtga gaactggttt    900

agttacttca ggcccccaa attccgaatc accaccgtgt ataacccggc cgcagtttct    960

tcccttgacg gtaactttaa ctttacgttt agcatgactg ggaatagtac gcacccgcct   1020

cttatcaatg gactggaaat ataccaggta ctggaactgc cccagttaga cacttatcag   1080

gacgaggtaa gcgccatgat gaacataaaa accatttatg ggatgtcgaa gcgcagctcg   1140

tggcaggggg acccttgcgc acctgaactg taccgatggg aggggcttaa ctgctcatac   1200

cccaacttcg cccctccaca aataatctcc atgaatatgt cggggtccaa catgagcgga   1260

acgattacct ccgacatttc aaaattaacc cacatgcgcg agctggacct ttccaataac   1320

gacctaagtg gcgacatccc tttcgtattc tcggacatga aaaacatgac cttgatcaat   1380

atgagcggga ataaaaactt gaacaggtcc gtaccggaaa cgctccagaa acggatagac   1440

aataagtcac ttacgttaat acgtgacgag actgggaaga actctacgaa cgtggtagcg   1500

attgcagctt ccgttgcctc tgttttcgca gtcttggtaa ttatggcgat tgtcttcgta   1560

gttattagga agaagcaacg cacaaacgag gcatctggtc cgcgcagttt tacgacaggg   1620

acagttaaaa gcgacgcccg ttcatcctca agtagcatta ttactaaaga gcgtaaattt   1680

acctactcag aagttctcaa aatgaccaag aatttcgaac gcgttctggg aaagggaggt   1740

ttcggtactg tataccacgg caatatggac gacacccagg tcgcagtaaa gatgctaagc   1800
```

cacagtagcg ctcagggcta caaggaattc aaggccgaag tggagttgct actacgagtg 1860
caccatcgtc acatggtcgg tctcgtaggc tattgcgacg acggggataa ccttgccctg 1920
atttatgagt acatggagaa gggcgatatg cgggagaaca tgtccggcaa gcatagcgtg 1980
aacgttctat cttgggaaac gcgcatgcag attgcggtag aagctgcgca gggcatggaa 2040
tacatgcata acgggtgccg tccacccatg gttcaccgtg atgtcaagcc gactaatata 2100
ctactcaacg aaagatcaca ggcgaagttg gctgatttcg gattgagcag gtctttccca 2160
gtcgacgggg agtcccacgt tatgacagtg gttgcaggca caccaggata tctagaccct 2220
gaatactatc gcaccaattg gctcagtgaa aaatctgacg tctattcctt cggggttgtt 2280
ctcctggaaa ttgtaactaa tcaacccgtt atgaacaaaa atcgggaacg tccccacata 2340
aacgagtggg tcatgtttat gctgacgaac ggtgacataa aaagcatagt tgatccaaag 2400
atgaacgagg attacgatac gaatggagtt tggaaagtgg tggaaatggc cctagcatgc 2460
gttaatccta gcagctcgcg acgacccaca atgccccatg tcgttatgga acttaatgag 2520
tgcttagcaa tggagatcga gcgaaagcag gggtctcagg ccacctatat taaagagtcg 2580
gtagaattct caccgtcgag cgctagtgac ttctctccgc tcgcgaggtg a 2631

<210> SEQ ID NO 6
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 2" /mol_type="unassigned
DNA"

<400> SEQUENCE: 6
atgcggttca tgtcttttat gatttttgta tttgctgttc taggcttggt gcaagcgcaa 60
gatcagtctg ggtttatttc actagactgc gggatggtgc caacggaaat tacctacgtc 120
gagaagtcga cgaacatcac ctatcgttcg gatgcaacct acatcgactc aggcgtgcct 180 ggaaaaaataa acgaagtata cagaactcag ttccaacagc agatttgggc aatgcgatca 240
ttcccggaag gacagcggaa ttgctataat ttttccctca ccgctaagag aaagtactta 300
ataaggggaa cgtttatata cggggaactac gatggcatga accaattgcc aagtttcgac 360
ttatatatcg gtcctaataa gtggacgtct gtctcgatac ccggggtaag aaacggaagc 420
gtgtctgaga tgatacacgt cttacgtcag gaccacttac agatctgtct cgtgaagacg 480
ggtgagacta cacctttcat ctcgtccatg gagctccgcc cgatgaacaa caacacctat 540
gttacgaaga gtggcagttt gattgtcgtc gcgcggctct atttttcccc gacgccgccc 600
ttcttgcggt acgacgagga cgttcacgac aggatctgga tacctttttct ggacaataag 660 aactcgatgc tgtccaccga actttcagtc gacacgtcga atttttataa cgtcccacag 720
accgttgcta agaccgccgc ggtgccgctc aacgcgacac aaccaatgaa gataaattgg 780
tcacttgatg atatcacatc tcagtcatat atttacatgc actttgcgga gatcgaaaac 840
ttggaggcga acgaaactcg ggagtttaac ataacctata acggaggaga gaactggttt 900
tcttacttca ggccgcctaa gttccggatt acgactgttt ataacccggc agctgtgagt 960
agtttggacg gtaactttaa tttcacattt tcaatgacag gcaattccac gcaccctccc 1020
ttaataaacg gtttagaaat ctatcaggtc ctcgaattac ctcaacttga cacgtatcag 1080
gatgaggttt ccgcgatgat gaacatcaaa actatatacg gaatgagtaa gcgaagtagt 1140
tggcaggggg acccttgcgc gccagaatta taccggtggg aggggctgaa ctgtagctat 1200
ccgaatttcg ccccaccgca gattatctct atgaacatgt ctggtagtaa tatgtcggga 1260
accataacct cggacatatc gaaattgaca cacatgcgag agctagacct ctcaaacaac 1320
gacctttctg ggatatcccc gttcgtcttc tctgacatga aaaatatgac acttataaat 1380
atgtctggca acaaaaacct aaatcgctca gtccctgaaa cgcttcaaaa acgaattgat 1440
aataagagtc taacacttat ccgtgacgag acgggcaaga acagtacgaa cgtagtggca 1500
attgcggcct cggtggcctc agtattcgca gtgctcgtaa tcatggccat agtctttgtc 1560
gtcattagaa agaaacaacg aaccaacgag gccagtggtc ctcgttcctt cacgacaggc 1620
accgtaaaat cagacgccag gagttcatct agttccatca ttaccaaaga gaggaaattt 1680
acgtattctg aagtacttaa aatgacaaag aattttgaac gggttttggg caagggggt 1740 ttcggtacag tttaccacgg aaatatggac gacacgcagg tcgcggtaaa gatgctaagt 1800
cacagcagtg cacaggggta taaagaattt aaggcagaag tagagttgtt gttacgggtg 1860
caccataggc acatggtagg acttgtcggg tattgcgacg acggcgataa tcttgcaatg 1920
atatatgagt acatggagaa gggagatatg agggagaaca tgtctgggaa gcatagtgtc 1980
aatgtgttgt cttgggagac cagaatgcaa atagcagtgg aggcggctca gggaatggaa 2040
tatatgcaca acgggtgccg acctcccatg gtgcaccgag acgtgaagcc aacaaatatt 2100
ttactgaatg aacgcagtca agcgaagttg gcggatttcg gcctatcgcg aagtttccca 2160
gtggatggag agtcccacgt gatgacggta gtagctggga ccccgggtta cttagatcca 2220
gaatactacc gtaccaactg gttatctgag aaatcggatg tttatagctt tggggttgtc 2280
ttactggaaa tagttacgaa tcaacccgtc atgaataaga atcgtgaaag accccacatt 2340
aacgagtggg ttatgttcat gttgactaac ggtgacatca aatctatcgt tgatccaaaa 2400
ctgaacgagg actacgatac gaatggtgta tggaaagtgg tagagttggc actagcgtgc 2460
gttaatcctt catccagccg taggcccacg atgccacatg tcgtcatgga actaaatgag 2520
tgcctggcca tggaaattga gagaaagcag ggatctcagg caacttatat caaagaatcc 2580
gtcgaattct ccccaagttc ggcttctgat ttctcgcccc tcgctcgcta a 2631

<210> SEQ ID NO 7
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence" /note="Nucleotide sequence RLK2, variant 3" /mol_type="unassigned DNA"

<400> SEQUENCE: 7
atgcgatttt tgagtttctt gatatttgta ttcgccgtgt tgggcatggt tcaagctcag 60
gatcaatcag ggtttataag tctagactgt ggtttggtcc cgacagagat aacttacgtg 120
gagaaatcta cgaacataac atatcgctca gacgctacat acatagacag cggtgttcct 180
ggtaaaatca acgaggtata ccgaactcaa ttccagcaac aaatttgggc aatgaggtct 240
tttcccgagg ggcagagaaa ttgctacaac ttttccctta cagctaagag gaaataccta 300

-continued

```
atccgcggta ctttcattta cggtaactac gatggtatga atcaacttcc tagctttgac    360
ctttatatag gtcccaataa atggacctct gtctcgatac cgggcgtccg caacgggtcg    420
gtatccgaaa tgatccatgt ccttcgacaa gatcatttgc agatttgcct tgtcaagact    480
ggggagacca cacccttcat ttcttccttg gaattacgtc cgttgaataa taacacatat    540
gtcaccaagt ctgggagctt gattgtagtg gcccgtctct acttctcacc gacgccacct    600
tttctccgct atgacgaaga tgtacacgat cgcatttgga ttccgtttct agacaacaaa    660
aacagcatgc tatcgactga gctctctgtt gacacatcca atttttataa cgtgccccag    720
acagtagcaa agactgccgc ggtacccctg aacgccactc aaccgatgaa gatcaactgg    780
tccctggacg atatcacttc acaaagttat atttacatgc atttcgcgga gattgaaaac    840
ctagaagcta acgaaactag agagtttaac atcacgtata atgggggggga gaactggttc    900
tcctattttc gtcccccaa gtttcgtata accactgtct acaaccccgc cgctgtttcc    960
tcgctagacg ggaatttcaa ctttactttt tccatgaccg ggaactctac tcacccgcct   1020
cttataaatg ggttagaaat ttaccaagtt ttggaacttc ctcagctaga cacataccaa   1080
gatgaggtgt cagccatgat gaatattaaa acgatttacg gcatgtcgaa acgctcttcc   1140
tggcagggcg atccttgtgc tccagaacta tacaggtggg agggacttaa ttgttcctat   1200
ccaaacttcg caccaccgca aatcatcagt atgaacttga gtggttctaa catgtctggg   1260
acgataacaa gtgacatttc caaactcacc cacatgcggg aactagattt atccaataac   1320
gacttatcag gtgacatccc gtttgtgttc agtgacatga aaaacttgac actcataaat   1380
atgtcgggaa acaagaactt gaatcgcagt gtgcctgaaa cgctacaaaa gcgtatcgac   1440
aataagtccc tcacgctaat ccgggatgag accggaaaga attcaacaaa tgtggttgcc   1500
atagcagcat ccgtggctag cgtcttcgca gtcctagtta taatggccat cgtctttgtt   1560
gttataagaa aaaaacagcg aaccaacgag gcgtcgggac cacgaagctt cactactggt   1620
acggttaaaa gcgacgctag gtcctcctct tcaagcataa taacaaaaga aagaaaattc   1680
acatattccg aggtccttaa aatgactaag aatttcgaaa gagtacttgg aaagggcgga   1740
tttggtaccg tgtaccatgg taatatggac gacactcagg tcgcagttaa aatgctttcc   1800
catagcagtg cgcaaggcta caaggaattt aaagcagaag tggagctttt attacgagtt   1860
catcacagac acatggttgg gcttgttggg tactgtgatg acggagataa tctggctatg   1920
atctacgagt acatggaaaa gggcgatctg agggaaaaca tgtcgggtaa gcacagtgtc   1980
aatgtattgt cgtgggaaac tcgtatgcaa atcgcggtgg aggcagcgca aggaatggag   2040
tacttgcaca acggatgcag gcctcctatg gtacatcgag acgtgaagcc tacaaatata   2100
ttattaaatg aaaggagcca ggcaaaatta gccgatttcg ggctatcgag atctttcccc   2160
gtagacggcg aatctcacgt gatgacagtt gtagcaggaa ctcctggata tttagaccca   2220
gaatattaca ggacgaattg gctatctgag aagtcagatg tgtattcgtt cggggtagtt   2280
ttattggaga tagttacgaa tcagccagtt atgaataaaa atcgggagag accgcacatt   2340
aacgaatggg taatgtttat gctgacaaat ggggatatca aaagcatcgt agacccgaag   2400
ctgaatgagg attacgatac aaatggcgta tggaaagtgg tagaaatggc tttagcatgc   2460
gtaaatccgt catcatctcg tagaccaacg atgccgcatg tagtaatgga actaaacgaa   2520
tgtctagcta tggagattga acgcaagcag ggtagtcaag ctacttacat taaagaatcc   2580
gtggaattct caccaagctc agccagcgat ttctccccac tagcaaggta a            2631
```

<210> SEQ ID NO 8
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 4" /mol_type="unassigned DNA"

<400> SEQUENCE: 8
atgcgatttt tgagctttat gatattcgtt ttcgcagtac tcggtttggt tcaagctcaa 60
gatcaatcag gatttatcag cttagactgt ggtatggtac caaccgagat tacctatgtc 120
gaaaagtcga ccaacataac ttaccggtcc gacgctacgt acatcgacag tggggtccca 180
gggaaaatca atgaggtcta tagaacgcaa tttcagcaac agatatgggc gttgcgctcg 240
ttccccgagg gacagcgcaa ttgctataac tttagtctaa ctgcaaaacg taagtacttg 300
atcagaggga cctttattta tggcaactat gatggtatga atcagttacc gagcttcgac 360
ctttatattg gtccaaacaa gtggacctct gtatcgatac caggtgtcag aaatgggagt 420
gtttccgaaa tgatccacgt cttacgacaa gatcatttac aaatttgcct tgtgaaaaca 480
ggagaaacaa caccattcat ttcttcattg gagcttcgtc ctatgaacaa caatacatat 540
gtaacaaagt caggatcgct catcgtggtc gcaagacttt acttctctcc aacgccaccc 600
tttctcaggt acgatgaaga cgtgcacgat cgaatctgga ttccattcct agataataaa 660
aattccatgt taagcacgga actctcagtt gatacaagta acttctacaa tgtgcctcag 720
actgtggcga aaactgccgc cgtcccgcta aacgcaacgc aacctatgaa gataaactgg 780
tctctcgatg acatcacttc acagtcttat atttacatgc atttcgctga aatagaaaac 840
cttgaggcta atgaaacccg ggagtttaac atcacttaca atgggggcga aaattggttc 900
tcctattttc gtccaccaaa attccgtata actacagtat ataacccagc cgcagtcagt 960
tctctagacg gcaacttcaa ttttacattc tcgatgaccg gtaattctac acatcctcct 1020
cttatcaatg gactggagat ctaccaggtc ctagagcttc cgcaactcga tacataccag 1080
gatgaagttt ccgcaatgat gaatatcaag acaatttatg gaatgagcaa aaggtcttct 1140
tggcaggggg atccatgtgc tcccgagctt tatcgttggg agggtctaaa ttgttcctat 1200
cccaactttg cgccaccgca gataatatct atgaacatga gtggaagtaa tatgagtggt 1260
accattacat cagatataag caagcttact cacatgagag aacttgacct gtcaaacaac 1320
gatttatcag ggatatcccc gtttgttttc tctgacatga agaatttgac actcataaat 1380
ttgagcggaa acaaaaactt aaaccgcagt gttccagaga ctcttcaaaa gcgtatagac 1440
aataaatctt taacactaat aagagatgag acaggtaaaa actccacaaa tgtggtagcg 1500
attgcagcgt ctgtagcgag cgtatttgcg gtgctagtta ttttggctat cgtgttcgtc 1560
gtaatccgta aaaaacagcg aactaacgag gcttcaggac cacgatcatt tactaccggc 1620
actgttaaga gtgatgctag atccagtagt tcatccatca taactaaaga acgcaagttc 1680
acttactccg aagtgttgaa aatgaccaag aattttgaga gagtgcttgg taaaggaggg 1740
ttcggaacgg tctatcatgg taatttggat gacactcaag tggctgtgaa aatgctttca 1800
catagtagcg ctcagggata caaggagttc aaagcagagg ttgaactgct tctaagagtg 1860
caccatagac acatggttgg gctcgtgggt tattgcgacg acggggataa cctcgcactg 1920

-continued

```
atttacgaat acatggaaaa gggcgatctg agggaaaaca tgtcagggaa acactccgtc   1980

aatgtccttt cgtgggaaac cagaatgcaa atagcggtgg aagccgcgca ggggttggag   2040

tacatgcaca acggttgtcg acctcccatg gtacacaggg atgtgaaacc caccaatatc   2100

ttattaaacg agcgatccca agccaagctg gccgattttg ggctaagccg gtcctttcct   2160

gttgatggtg agtctcacgt catgacagtt gtggcaggaa cacctggtta cttagaccct   2220

gagtattatc gcactaactg gctaagcgaa aaaagtgacg tgtatagctt cggtgtagtc   2280

ctgttggaaa tagttacaaa tcagcccgtc atgaataaaa accgagagag acctcacatc   2340

aacgagtggg tcatgttcat gcttaccaac ggtgatatta aatctattgt tgatccgaaa   2400

atgaacgagg actatgacac aaacggcgtc tggaaagttg tcgagttggc tctcgcatgt   2460

gtaaatcctt cttcgagccg tcgtccgaca atgccacatg tggttatgga actaaacgag   2520

tgcctggcgt tggaaatcga acgaaaacaa gggtctcaag ctacgtatat aaaagagtcg   2580

gttgagttct ccccaagctc tgcgtcagat ttctcccctt tagctaggta a            2631
```

<210> SEQ ID NO 9
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 5" /mol_type="unassigned DNA"

<400> SEQUENCE: 9

```
atgaggtttt tgtctttctt gatatttgta ttcgcagtat tgggtttggt tcaagcgcaa     60

gaccaatcag gattcatctc tctagactgc ggcttggtac caacggaaat tacctacgta    120

gaaaaatcta cgaacataac ttacagatca gacgcaactt acatcgacag tggcgttcct    180

gggaaaatca acgaagtata cagaactcag tttcagcaac aaatatgggc cttgcggtct    240

tttcctgaag gccaaagaaa ctgttataac ttcagtctca ccgcaaaacg taagtattta    300

ataaggggca cctttatcta tgggaattat gatggtttga atcaactccc cagctttgat    360

ctatatatag gtccaaacaa atggaccagc gtttcgatac cgggagtgag aaatggttca    420

gtctccgaga tgatccacgt cttaagacaa gaccatttac aaatttgttt agtgaaaacc    480

ggagagacta caccatttat ttcatcattg gaacttcgcc ctttgaacaa taatacatac    540

gtcacaaaga gtgggtcgct aattgtagtg gcgagacttt acttttctcc cactccccca    600

tttctcaggt atgatgagga tgtccacgac cgaatttgga tcccattctt agataacaag    660

aattccttgc tatctacgga actctctgtt gacacaagta atttttacaa cgttcctcag    720

actgtggcca aaactgctgc tgtgccctta aatgctactc aacctctgaa aataaattgg    780

agtctcgacg atatcacatc acaatcatat atttatatgc attttgcaga aatcgaaaat    840

ttagaagcta atgagacgcg agaatttaat attacttaca atggtggcga aaattggttc    900

tcctattttc gtcccccaaa atttcgtatt acaacggtat ataatccggc agcagtgagt    960

tcgctagatg ggaatttcaa cttcactttc agtatgactg ggaacagtac tcatccgcca   1020

ttaattaacg gccttgaaat ctaccaagtt ctagagctgc cacagcttga tacataccaa   1080

gatgaagtgt ccgctatgat gaacatcaag acaatatatg gattgagcaa aaggtctagc   1140
```

```
tggcaagggg atccatgtgc acctgaactg tatagatggg aaggtttaaa ctgttcatat   1200

cccaacttcg cgcccccgca gatcataagt ttgaacatga gtgggagcaa tttgagtggt   1260

actatcacat ctgatatttc caaactaaca catatgagag agttagacct ctcgaataat   1320

gacttatcag gtgatatacc atttgttttt tctgacatga agaatatgac actcataaac   1380

ttgagtggaa ataaaaacct aaatcggagt gtgcccgaga cgcttcagaa gaggatagat   1440

aacaaatctt taacactaat tagagatgag accggaaaga atagtacaaa tgtagtagct   1500

attgctgcat cagtagctag cgtgtttgct gtgctagtta tcatggctat tgtgtttgtc   1560

gtcataagga aaaagcaaag aacaaatgaa gcttcaggac cccgatcatt tactactggc   1620

acggttaaga gtgatgcaag aagttcgtca tctagcatca taacaaaaga acgcaagttc   1680

acttattcgg aagtactaaa aatgactaaa aattttgaaa gagttcttgg caaaggcggg   1740

tttggaacag tgtatcatgg taatatggat gatactcaag tggctgtgaa aatgctttct   1800

cactcatcag ctcaaggtta taaagaattt aaagcagagg ttgaattact tctaagagtt   1860

caccaccgtc acttggtggg acttgtaggc tactgtgatg acggagacaa cttagcactg   1920

atctatgaat acatggagaa aggagatctg agggagaata tgtcagggaa gcacagtgtg   1980

aacgtactaa gctgggaaac aagaatgcaa atagcagtag aagctgccca aggtttggaa   2040

tatatgcaca acggctgtag gcctcctatg gtacatagag atgtgaaacc aaccaacatt   2100

ctcttaaatg agcggtctca ggcaaaactc gcagactttg ggctatctag atcttttcct   2160

gtagacgggg agtcccatgt tatgacagtc gttgcgggaa cacctggtta cttagatccg   2220

gaatattata gaacaaattg gctgagcgag aagagtgacg tgtatagctt tggcgttgtg   2280

cttttagaga tagtcaccaa ccaacctgtt atgaacaaga accgtgaaag acctcatatc   2340

aacgagtggg tcatgttcat gcttacgaat ggggatataa aaagcatcgt cgacccgaaa   2400

ctgaatgaag attacgacac aaacggtgtg tggaaggttg tggagttggc tcttgcttgt   2460

gtaaacccgt cctcaagccg tagaccaaca atgccgcacg tggtgatgga gctaaacgaa   2520

tgtctagcat tggagataga gaggaaacaa ggaagtcaag cgacgtacat aaaagaatct   2580

gtagagtttt ctcctagttc ggccagcgat ttttcccctt tggctaggta a            2631
```

<210> SEQ ID NO 10
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 6" /mol_type="unassigned
DNA"

<400> SEQUENCE: 10

```
atgaggtttt tgtctttctt gatattcgtt tttgcagttc ttggaatggt tcaagctcaa     60

gaccaatcag gattcataag cttagattgc ggtttggtac ctacggagat tacatacgtg    120

gaaaagtcaa ctaatataac atacagatca gatgcaacct acattgacag tggagtgccc    180

ggcaagataa atgaggtcta ccgtacgcag tttcaacagc agatttgggc catgagaagc    240

ttccctgaag gtcaaagaaa ctgttataac tttagtctca ccgcaaaacg taagtatcta    300

atcagaggaa cctttatcta cgggaattat gacggtttga accaactccc gtcttttgat    360

ctttacatcg gtcccaacaa atggacctct gtttcgatcc ccggggtgag aaatggttcg    420
```

-continued

```
gtctcagaga tgatccatgt cttaagacag gaccacctgc agatttgtct ggtgaaaaca    480
ggagagacta caccattcat ttcatcattg gaattacgtc caatgaataa taatacatac    540
gttacaaaga gtggatcgct tatagtggtc gcaagacttt acttctcacc cactccgccc    600
tttttgcgct atgatgagga cgtccacgac cgaatctgga tcccattctt agataacaaa    660
aattccttgc ttagcacaga actctctgtt gacacaagta acttctataa tgtacctcag    720
actgtagcga aaaccgctgc tgtcccttta aatgcgactc agcccctgaa aataaattgg    780
agtctcgacg acattacttc acagtcatat atctacatgc atttcgctga aatcgagaat    840
cttgaagcta acgaaaccag agaattcaat attacttaca atggtggtga aaattggttc    900
tcctattttc ggcctccaaa gtttaggata actactgtct acaatccagc ggctgtgtct    960
agtcttgatg ggaatttcaa cttcactttc tcgatgaccg gtaattctac tcacccacct   1020
cttatcaatg gcctagagat ttatcaagtc ctagagcttc cacagctaga tacttaccaa   1080
gacgaggttt ccgcaatgat gaacatcaag acaatttacg gattgagcaa aaggtctagc   1140
tggcaaggag atccatgcgc tcctgagtta tatagatggg aaggattaaa ctgtagttat   1200
ccaaactttg cgccaccaca gatcatctcc ttgaatttga gtggaagcaa tatgagtggt   1260
accataacgt ctgatatatc caaactaaca cacttgagag agctagactt atcaaacaat   1320
gacttatcag gagacattcc atttgttttt tctgatatga agaatttgac actcataaac   1380
atgagtggaa acaagaatct aaatcgctca gttccagaga ctctgcagaa aaggatagat   1440
aacaaatctt taacactaat tagagatgaa acaggaaaaa atagtacgaa tgtagtggct   1500
atcgcagcaa gcgtggctag cgtgttcgct gtgctagtca tcttggccat cgtttttgtc   1560
gtcataagaa agaagcagag aactaatgaa gcttcaggac cccgatcatt tactactggg   1620
acggttaaga gtgatgcaag aagttcttcg tcatcaatca taacaaagga acgcaagttt   1680
acatattcgg aagtactcaa aatgactaaa aactttgaaa gagttcttgg taaaggaggg   1740
ttcggaacag tctaccatgg gaatatggac gacactcaag tagctgtgaa aatgctttct   1800
cattcatcag cacaaggtta taaagagttc aaagcagaag tggaacttct tctgcgcgtt   1860
catcaccggc atttggtggg gcttgttggg tactgcgatg atggagacaa cctcgcaatg   1920
atatatgaat acatggaaaa aggagatctg agggagaata tgtcaggaaa acacagtgtc   1980
aatgtcctaa gctgggaaac aagaatgcaa atagctgtag aggctgcaca aggattggag   2040
tatttgcaca acgggtgtag gcctcctatg gtacatagag atgtgaaacc taccaatata   2100
ttattaaatg agcggtctca ggcaaagcta gccgattttg ggctaagcag atcttttcct   2160
gtcgatggtg agtctcatgt catgacagtc gtggcaggga cacctggtta tttagatcct   2220
gaatattaca ggacaaactg gctgagcgag aagagtgacg tgtacagctt tggtgtggtg   2280
ctgttagaga tagtgacaaa ccagcctgtg atgaataaaa accgagaaag accgcatatc   2340
aatgagtggg ttatgttcat gctcaccaat ggggacatta aatcgattgt cgacccgaag   2400
ctgaatgaag attatgacac aaacggtgtt tggaaagttg tagagatggc gttggcgtgt   2460
gtgaacccgt cttcaagccg aaggccgaca atgccacacg tggtcatgga actaaacgaa   2520
tgccttgcgt tggagataga aaggaaacaa ggtagtcaag cgacgtacat taaagaatcc   2580
gtcgagttca gtccatcgtc tgcctctgat ttctcacctt tagctagata a            2631
```

<210> SEQ ID NO 11
<211> LENGTH: 2631
<212> TYPE: DNA

<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 7" /mol_type="unassigned DNA"

<400> SEQUENCE: 11

```
atgaggttca tgtctttctt gatcttcgtg ttcgcagtat taggattggt tcaagctcaa     60

gaccaatcag gatttataag cttagattgt ggtttggtgc ctacggaaat tacttatgtg    120

gaaaagtcga ctaacataac atacagatca gatgcaactt acatcgacag tggagttccc    180

gggaagatca atgaagtcta cagaactcag tttcagcagc agatttgggc cttgagaagc    240

ttcccagagg gtcaaaggaa ttgctacaac ttcagtctca ccgcaaaacg taagtatcta    300

atcagaggca ccttcatcta tgggaattat gacggtttga atcagctgcc gagttttgat    360

ctttacatcg gtccgaacaa atggacctct gtgtcgatcc ctggagtgag aaatggttca    420

gtctctgaaa tgatccacgt gttaagacag gaccatcttc aaatttgtct tgtgaagaca    480

ggagaaacta ctccgtttat ttcttcaatg gaacttcgtc ctttgaacaa taatacgtac    540

gtcacaaaaa gtggaagcct tattgttgtc gcaagacttt acttttcacc cactccacca    600

tttttaaggt atgatgagga cgtccatgac cgaatttgga ttccgttctt agataacaaa    660

aatagcttgc ttagcacgga actctctgtt gatacaagta acttctacaa tgtgcctcaa    720

actgtagcga aaactgcggc tgtaccttta aacgctactc agccactgaa aataaattgg    780

agtctcgacg acatcacttc acagtcatat atatacatgc atttcgccga aattgaaaac    840

cttgaagcaa atgagactag ggaatttaat atcacttaca atggtggcga aaattggttc    900

tcctatttta gacctccaaa gtttcgtata accactgtat acaatcccgc agctgtgagt    960

tctctagatg ggaatttcaa cttcactttc tcgatgaccg gtaactctac tcatcctcct   1020

cttatcaacg gccttgagat ttatcaagtt ctagagcttc cacagcttga tacatatcag   1080

gatgaagtga gtgctatgat gaatatcaag actatatatg gattgagcaa aaggtcaagc   1140

tggcagggag atccatgtgc tcctgagtta tatagatggg aaggcttaaa ctgtagttat   1200

ccaaactttg cgccaccgca gatcatatcc ttgaacatga gcggaagcaa tatgagtggt   1260

accataacct ctgacatatc caaactaaca cacttgagag aattagatct ctcaaacaat   1320

gacttatcag gagatattcc atttgttttt tctgatatga agaatttgac gctcataaac   1380

atgagtggaa acaaaaatct aaatcgctca gtgcctgaaa ctcttcagaa gaggatagat   1440

aacaaatctt taacactaat tagagacgag accggaaaaa atagtacaaa tgtagttgct   1500

atcgcagcat cagtggctag cgtgtttgct gtgctagtta ttttggctat cgtttttgtc   1560

gtcataagga aaaaacagag aactaatgaa gctagtggac cccgatcatt cactactggc   1620

acggttaagt cggatgccag atcgagcagt tcatcaatca taacaaagga acgcaagttt   1680

acttactcgg aggtactaaa gatgactaaa aactttgagc gagttcttgg taaagggggg   1740

ttcggaacag tatatcatgg gaacttggat gatactcaag tagctgttaa aatgctcagc   1800

cattcatcgg ctcaaggtta caaagagttc aaggcagagg tggagcttct tttaagagtt   1860

catcacagac atttggtggg acttgtaggt tactgcgatg atggagacaa cttggctctg   1920

atctatgaat acatggaaaa aggagacctg cgggaaaata tgtcaggaaa acacagtgtc   1980

aatgtcctaa gctgggaaac aagaatgcaa atagctgtag aggcagcaca agggttggag   2040
```

```
tatttgcata acggatgcag gcctcctatg gtacatagag atgttaagcc aaccaacatt   2100

ttattaaatg agcggtcaca ggcaaaacta gccgacttcg ggctatcgcg atcttttcct   2160

gttgatggtg aatctcacgt catgaccgtc gttgcaggaa cacccggtta cttagatcct   2220

gagtattaca gaactaactg gcttagcgag aaaagtgatg tgtatagctt tggtgtagtg   2280

cttttagaga tagtcacaaa ccagcctgtg atgaataaaa accgagagag acctcatatc   2340

aacgagtggg ttatgttcat gcttaccaat ggggatatca agtcgattgt cgacccgaaa   2400

ctgaatgaag actacgatac aaacggtgtg tggaaggtgg tagagatggc tttagcttgt   2460

gtaaacccgt cttcaagccg tagaccgaca atgccacacg tggtgatgga gctaaacgaa   2520

tgtctcgctt tggaaataga aaggaagcaa ggtagtcaag cgacgtacat aaaggaatct   2580

gttgagttta gcccatcttc tgcttctgat ttttcacctt tagctaggta g            2631
```

<210> SEQ ID NO 12
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 8" /mol_type="unassigned DNA"

<400> SEQUENCE: 12

```
atgaggtttt tgtctttctt gatcttcgtt ttcgcagttc taggattggt tcaagctcaa     60

gaccaatcag gattcataag cttagattgt ggtttggtgc ctaccgaaat tacttacgtg    120

gaaaagtcga cgaatataac atacagatca gacgcaactt acatcgacag tggagttccc    180

gggaagatca atgaggtgta cagaacacag tttcagcaac aaatttgggc cttgagaagc    240

ttccctgagg gtcaaagaaa ttgttacaac ttcagtctca ccgcaaagcg taagtatcta    300

atcagaggaa cctttatcta tgggaattat gacggtatga atcaactccc gagctttgat    360

ctttacatcg gtccaaacaa gtggacctct gtttcgatcc ccggagtgag aaacggttca    420

gtctccgaaa tgatccatgt cttaagacaa gaccatctgc aaatttgtct tgtgaaaaca    480

ggagaaacga caccgtttat ttcttcattg gaacttcgtc ctttgaacaa taatacatac    540

gtcacaaaaa gtggatcgct tatcgtggtc gcaagacttt acttttcacc cactccgcca    600

tttctcaggt atgatgagga cgtccatgac cgaatttgga ttccattctt agataacaaa    660

aacagcttgt taagcacgga actttctgtt gatacaagta acttctacaa tgtgcctcaa    720

accgtagcga aaactgctgc cgtcccgtta aatgctacac agcctctgaa aataaattgg    780

tcattagacg acatcacttc acagtcatat atatacatgc atttcgctga aatcgagaat    840

cttgaagcta atgagaccag agagtttaat atcacttaca atggtggcga aaactggttc    900

tcctatttta gacctccaaa gtttcgtata acaactgtat acaatccagc agctgtaagt    960

tctctagatg ggaatttcaa tttcactttt tcgatgaccg gtaattctac tcatcctcct   1020

cttatcaacg gccttgagat ttatcaagtt ctagagcttc cacagcttga tacataccaa   1080

gatgaagttt ccgctatgat gaatatcaag acaatatatg gattgtccaa aagatctagc   1140

tggcagggag atccttgtgc acctgagtta tatagatggg aaggattaaa ctgtagttat   1200

ccaaactttg cgccaccgca gatcatatcc ttgaacttga gtggaagcaa tttgagtggt   1260
```

-continued accataacat cagatatatc caaactaaca catttgagag aactagattt atcaaacaat 1320
gacttatcag gagatattcc atttgtcttt tctgatatga agaatatgac actcataaat 1380
ttgagtggaa acaagaatct aaatcgctca gtcccagaga cgcttcagaa gaggatagat 1440
aacaaatctc taacactaat tagagatgaa accggaaaaa atagtacaaa cgtagttgct 1500
atcgcagcaa gcgtggcaag cgtgtttgct gtgctagtta tcttggctat cgtttttgtc 1560
gtcataagga aaaaacagcg cactaatgaa gcttcaggac cccgatcatt cactactggc 1620
acggttaaga gtgatgcaag atcatcgagt tcatcaatca taacaaagga acgcaagttc 1680
acatattcgg aggtgctaaa gatgactaaa aactttgaga gagttcttgg taaaggaggg 1740
tttggaacag tgtatcatgg taacttggat gatactcaag tagctgtgaa aatgctatct 1800
cactcatcag cacaaggtta taaagagttc aaagcagagg ttgaacttct tttaagagtt 1860
catcacagac atttggtggg acttgttggt tactgtgatg atggagacaa tttagctctg 1920
atctatgaat acatggagaa aggagacctg agggaaaata tgtcagggaa acacagtgtc 1980
aatgtactaa gctgggaaac acggatgcaa atagctgtag aggcagcaca gggattggag 2040
tatttgcata acggatgtag gcctcctatg gtacacagag atgtgaaacc aaccaacata 2100
ttattaaacg agcggtctca agcaaaactg gccgactttg ggctatccag atcttttccc 2160
gttgatggtg aatctcatgt catgacagtg gttgctggaa cacctgggta cttagatcct 2220
gagtattaca gaacaaactg gctaagcgag aagagtgatg tgtactcatt tggtgtagtg 2280
cttttagaga tagtcacaaa ccagcctgtg atgaataaaa accgagagcg ccctcatatc 2340
aatgaatggg tcatgttcat gcttaccaat ggggatatca agagtattgt cgacccgaaa 2400
atgaacgaag actatgatac aaacggtgtg tggaaggttg tagaattggc tttagcttgt 2460
gtaaacccgt cttcaagccg tagaccgaca atgccacacg tggtgatgga gctaaacgaa 2520
tgtcttgctt tggaaatcga aaggaaacaa ggtagtcaag cgacgtacat aaaagaatct 2580
gttgagttta gtccatcttc tgcttctgat ttttcccctc tagctaggta a 2631

<210> SEQ ID NO 13
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 9" /mol_type="unassigned
DNA"

<400> SEQUENCE: 13
atgcggtttc tatccttttt gatttttgta tttgcggttc tcggtttagt tcaggcacag 60
gaccaaagcg ggttcatctc cttagattgt ggcttggttc ccacggagat cacttatgtg 120
gaaaaaagca caaacataac ctaccgaagt gatgcgacgt acatagactc gggagtaccg 180
gggaagatca atgaggtgta cagaacgcaa ttccaacaac aaatatgggc actaagaagt 240
tttcccgaag gacaacgtaa ttgttacaat ttctccctaa cggccaaaag gaaatatctg 300
atccgcggca cgttcattta cggaaattat gatgggctga accaattgcc ctcttttgat 360
ctctatatag gtcccaataa atggacttca gtaagcatac cgggcgtcag gaatggttcc 420
gtctctgaaa tgatccatgt gcttcggcaa gaccacctgc agatatgtct tgtgaaaacg 480
ggcgaaacaa cgccattcat aagttcactt gaattacgtc cactaaataa taatacatat 540

```
gtcacaaaaa gcggaagcct tatagttgta gcccgacttt atttctcacc aacgccgccc    600
tttctaagat atgatgagga cgtacatgac cgaatatgga ttccctttct ggacaataaa    660
aatagtttgc tgtcaactga attatctgtt gatacgtcca atttttacaa tgtaccccaa    720
acggtcgcaa aaacggccgc cgtccctcta aatgccactc aaccgctaaa aatcaactgg    780
agcttagatg atataacgtc ccaatcttac atatacatgc attttgctga aatcgaaaat    840
ttggaagcca atgaaacccg agaattcaac ataacgtaca acggtgggga aaattggttc    900
tcatatttcc ggccgccgaa attccgtata accacagttt acaatcccgc ggctgtgtcc    960
tcgcttgacg ggaatttcaa ttttacattc agcatgactg ggaattccac acatccaccg   1020
ctcataaatg ggttggaaat ttaccaagtc cttgaattgc cgcaacttga tacgtaccaa   1080
gatgaggtaa gtgccatgat gaacataaaa acgatttatg ggttgtcaaa acgctcctca   1140
tggcagggcg acccatgtgc cccggagctg taccgttggg aagggttgaa ttgctcgtat   1200
cccaattttg ctccaccgca gataatttcc ctcaatctct cggggtccaa tttaagcggg   1260
acgataacct cagacatatc taaacttacc cacctccgtg agcttgatct atccaataat   1320
gatttaagcg gagacatacc atttgtattc tcagacatga aaaatcttac gatgattaat   1380
ctcagcggga ataaaaatct gaaccggagt gtccctgaaa ccctccaaaa acgtattgac   1440
aataaaagtc tgacgcttat tcgtgatgaa acaggcaaaa attcgacgaa tgtcgttgcg   1500
attgctgcgt cagtagcatc ggtctttgcg gtacttgtaa ttctcgccat tgtctttgta   1560
gtaatcagaa aaaaacaacg aacaaatgag gcgagtggtc cgagatcctt tacaactggg   1620
acagtgaagt cggatgctcg tagctctagc tcgagtataa ttacgaaaga gcgaaaattt   1680
acttactctg aggtacttaa aatgacaaaa aattttgaac gtgtacttgg caaaggtggg   1740
tttgggacag tgtaccatgg caatcttgat gatacccaag tagcagtcaa aatgctatcg   1800
cattcctcgg cccaagggta caaagaattc aaagctgaag tagaattgtt attaagagta   1860
catcatcgac atctcgttgg gctggtggga tactgtgatg atggtgacaa tctggcactt   1920
atttatgaat acatggagaa aggtgattta cgtgaaaaca tgtctggtaa acattctgta   1980
aatgtattat cttgggaaac gagaatgcaa attgcggtgg aagcggcaca agggctagaa   2040
tatctacata atgggtgcag gcctccaatg gtccatcgtg atgtgaaacc cactaacatt   2100
ctactgaacg aaagatccca agcgaaactg gcagattttg ggctgtcgcg ttcgtttcct   2160
gttgatgggg aaagtcatgt gatgacagtc gtggcgggga cacccgggta tctcgatcct   2220
gaatattacc ggaccaattg gctatccgaa aaaagcgatg tgtatagctt tggggtcgtc   2280
ttgttggaaa tcgtaaccaa ccaaccggta atgaataaaa accgagaacg cccccatatc   2340
aatgaatggg tcatgttcat gctcaccaac ggggacatca aatcaatcgt ggatcctaaa   2400
ttaaatgaag attatgatac aaatggggtt tggaaagtcg tggagctagc cctggcttgt   2460
gtcaatccga gttcgtctcg ccgcccgacc atgccacatg ttgtaatgga gctcaatgaa   2520
tgtctggcat tagaaattga acggaaacag ggttcacagg cgacgtacat aaaagagagt   2580
gttgaattct ctccaagttc tgcctccgat ttcagccccc tggctcgctg a            2631
```

```
<210> SEQ ID NO 14
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
```

-continued

<221> NAME/KEY: source
<222> LOCATION: (1)..(2631)
<223> OTHER INFORMATION: /organism="Artificial Sequence"
/note="Nucleotide sequence RLK2, variant 10" /mol_type="unassigned DNA"

<400> SEQUENCE: 14
atgcgctttc tttcttttct tatatttgta tttgctgtgc ttggactagt gcaagcccag 60
gatcagagcg gtttcattag cctcgactgt ggattggtgc ccacggaaat tacttacgtg 120
gaaaaatcga ccaacattac ttaccgttca gatgcgactt atatagacag cggggtcccg 180
ggtaaaatta atgaagttta ccgtacgcaa tttcagcagc aaatatgggc tcttcgctcc 240
tttccagagg gccaacgtaa ttgctacaat ttctccctta cagccaagag gaaatatcta 300
atacgcggta ccttcattta tggtaattat gatggtttga accaactccc atccttcgat 360
ctctacattg ggcccaacaa atggacttcc gtctctatac ccggagttcg caatggctcc 420
gtgagcgaaa tgattcatgt cttacgtcaa gaccatctcc aaatctgcct ggtaaaaacg 480
ggcgaaacaa cccctttcat tagttcccta gagttgcgcc cgctaaataa taatacgtat 540
gtcacaaaaa gtggatcact gatcgttgtt gcgcgtctgt acttctcacc cacacctcca 600
tttttacgat atgatgagga cgttcatgac cggatttgga tacctttttt agacaataaa 660
aattccctac tgagtaccga attatcagtg gatacctcca atttctacaa tgttcctcaa 720
acagttgcca aaacagcagc ggtacccttg aacgcaaccc aacctttgaa gatcaattgg 780
tccctcgatg acatcacatc ccaatcctac atatacatgc attttgcaga gatagaaaat 840
ttagaagcga atgaaactcg cgaatttaat ataacttata acggaggcga aaattggttc 900
tcctacttcc ggccgccgaa gttcaggatt acgacagtct acaatcctgc agccgtgagt 960
agcttagatg gaaacttcaa ttttacattc tcaatgacag gtaattcaac tcacccgcct 1020
ttaataaatg ggctggaaat ataccaagtg ctggaacttc cgcagcttga tacatatcaa 1080
gatgaagtct cagccatgat gaatataaag acgatatatg ggttatcaaa gaggtcctca 1140
tggcaagggg acccttgtgc tcccgagtta taccgttggg agggtcttaa ttgctcatat 1200
cctaatttcg cgccgcccca aatcatatca ttaaacctct ctggatctaa tcttagtggc 1260
accatcacca gcgacatcag taaattaacg catctaaggg aattagatct ctccaataat 1320
gatttgagtg gtgacattcc gttcgtgttc tccgatatga aaatctcac gatgataaat 1380
ctgtcgggga ataaaaacct aaaccgatcg gttcctgaga ctctgcaaaa aagaatcgac 1440
aataaaagtt tgactttgat cagggatgag acgggtaaaa attccacaaa tgtagttgcg 1500
atcgctgcta gcgtagcaag cgttttcgcc gtacttgtaa tcctagcgat cgtgttcgta 1560
gtcataagga aaaaacaacg cactaacgag gcttccggcc cgagatcttt tacgacgggc 1620
acagtgaaaa gcgatgcgag atccagcagt agctcaatca tcacaaaaga gagaaagttt 1680
acttactcgg aggtgctgaa gatgaccaaa aattttgaac gtgtgcttgg gaaagggga 1740
tttgggacgg tataccatgg aaatttggat gatacgcaag ttgcggtgaa aatgctgagc 1800
cattcgtccg cacaaggata taaagaattc aaagcggaag tggaactatt gctgagggtg 1860
catcaccgac atctggtagg cctagttggc tactgtgatg atggcgataa tctagcgtta 1920
atatatgagt acatggaaaa aggggatctg cgcgaaaata tgtctggtaa acattccgta 1980
aatgtcctat cttgggaaac taggatgcaa attgccgtag aggccgcgca aggcttagag 2040
tatctgcata atggctgccg gccaccaatg gtgcatcggg acgtgaaacc gacaaacatt 2100
ttactaaacg aaagatctca agctaaactt gccgattttg ggctatccag gtcttttcct 2160
gtagatggtg aaagtcacgt gatgaccgta gtcgcaggca cgccagggta ccttgatccg 2220
gaatactaca ggacaaattg gttatccgaa aaatccgatg tctattcatt cggggtagtt 2280
ctcttggaaa tagtcactaa ccaacccgtc atgaataaaa atagagaaag accacatatt 2340
aatgaatggg taatgttcat gcttaccaat ggcgacatca aaagtatcgt cgatcctaaa 2400
cttaatgaag attatgatac caatggagtc tggaaagttg ttgagctggc tctcgcgtgc 2460
gtcaatccta gttccagcag acgacctaca atgccccacg tcgtaatgga gcttaatgaa 2520
tgtctagctc tcgaaattga gcgaaaacag gggagtcagg caacctatat aaaggagagt 2580
gttgaatttt cacctagctc agcatcggac ttctcaccgt tggcaagata g 2631

<210> SEQ ID NO 15
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 11" /mol_type="unassigned DNA"

<400> SEQUENCE: 15
atgcgatttc ttagcttttct catctttgta tttgcagtgc taggccttgt gcaagcccag 60
gaccaatcgg gatttattag cttggactgt ggccttgttc ctacagaaat tacctatgtg 120
gaaaaatcta caaacatcac ataccggtca gatgctacgt acatcgattc aggtgtacct 180
ggtaaaatta atgaagttta tagaactcag ttccagcaac aaatttgggc acttaggtcc 240
ttcccagaag gtcaaagaaa ctgctacaat ttttcgttaa ccgcgaaacg taagtatttg 300
ataaggggta cgtttatcta tggcaattat gacggtctta atcaactgcc tagcttcgat 360
ttgtacatcg gacctaacaa gtggacttcc gtcagtattc cgggagttcg gaacggctca 420
gtgagcgaaa tgattcacgt actccggcaa gaccatcttc agatatgttt ggtaaaaacg 480
ggtgagacta cccctttat ttcttctttg gagcttagac ccctgaataa caacacctac 540
gtgaccaaga gcgggtccct aatcgttgtg gcccgcctat atttcagccc tacaccacct 600
tttctcagat atgacgaaga cgtccatgac aggatttgga tcccgtttct tgataataaa 660
aatagtttgc ttagcactga gctgtctgtg gacacgagta acttctacaa cgtcccacaa 720
accgtggcca aaactgcagc tgtcccctg aacgctactc agcccctgaa gattaactgg 780
tcactcgatg acataactag ccaatcctac atctatatgc attttgccga aatagagaat 840
ctcgaggcta atgagactcg cgaatttaat atcacttaca atggaggtga gaattggttt 900
agctatttcc gcccccctaa atttagaatc acaaccgttt acaatccagc tgctgtgtcc 960
agtctagacg ggaattttaa tttcacattc tctatgaccg gtaattctac tcatccccg 1020 cttataaacg gtctcgaaat ataccaagtt cttgaactcc ctcaactcga tacttaccag 1080
gatgaggttt cggccatgat gaacataaaa accatatatg gactctcgaa acggagtagc 1140
tggcagggcg atccgtgtgc tccggagctg taccgctggg aaggacttaa ctgtagctat 1200
ccaaacttcg cccctcctca aattatatct cttaatcttt ccggatcgaa cttgtctggt 1260
acaatcacca gtgacattag taagctgact catcttaggg aactagatct tagcaataac 1320
gacctttcgg gcgacattcc attcgtattc tctgatatga agaacctaac aatgataaat 1380

```
ctaagcggca ataaaaattt aaacagatcc gttccagaaa ctctacaaaa gaggatagat   1440

aataaaagcc taaccttgat tcgggatgaa actggtaaga atagcactaa cgtcgtggcc   1500

attgccgctt cagtcgcgtc agtatttgct gtactagtca tactagcgat cgttttcgtt   1560

gttattagga agaagcaacg gacgaatgaa gcaagcgggc cgagatcatt tacgacaggg   1620

accgttaagt cagacgcgcg ctctagctcc agttctataa ttacaaaaga acgtaaattt   1680

acttactcag aagtccttaa aatgaccaaa aattttgaac gagtattagg taagggggc   1740

tttggtacag tctaccatgg caatttagat gatactcagg tggcagttaa aatgttgtcg   1800

catagttctg cccaggggta taaagaattc aaggcagaag tggagcttct cctacgggtc   1860

catcataggc atctagtggg attagtgggg tattgtgacg atggagataa cctcgcccta   1920

atttatgaat atatggagaa aggcgatcta cgcgagaaca tgagtggtaa acattccgtt   1980

aatgtgctct cgtgggaaac tcgcatgcaa attgccgtcg aagccgcgca gggactagaa   2040

tacttgcata atggctgccg gccgcctatg gtacatcgcg atgtgaaacc caccaatatt   2100

ctacttaacg aacgtagtca ggctaaactc gctgattttg gactttctag aagttttccc   2160

gtcgacggag aatcacacgt aatgacagta gtggctggca ctccagggta cttggatccg   2220

gaatactatc gaacgaactg gttatcagaa aaaagtgacg tgtacagctt tggtgtcgtt   2280

ctgcttgaga tagtgactaa tcagccagtg atgaataaga atagagagag accgcacatt   2340

aacgaatggg tgatgttcat gctaactaat ggggacatta aaagcatcgt ggacccgaaa   2400

cttaatgagg attacgacac gaatggagtg tggaaggtgg tggagctagc gctagcgtgt   2460

gtcaatccga gctctagtag gcgccctacg atgcctcatg tggtaatgga gttgaatgaa   2520

tgtctggctc tggaaatcga acgaaagcag ggcagtcagg cgacatacat caaggagagc   2580

gtcgaattct cgcctagcag tgctagcgat ttctctccct tagctaggtg a            2631
```

```
<210> SEQ ID NO 16
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
      /note="Nucleotide sequence RLK2, variant 12" /mol_type="unassigned
      DNA"

<400> SEQUENCE: 16
```

```
atgagatttc ttagtttctt gatttttgtg tttgcagtgt taggccttgt tcaggctcaa     60

gaccaatcag gtttcatttc actagattgc ggtctagtac ctactgaaat tacctatgtc    120

gagaaatcta ccaatatcac ctatcgatca gacgctacgt atatcgactc cggtgtgccg    180

ggtaagatta acgaagtcta taggacccag ttccagcagc aaatctgggc ccttagatct    240

tttcctgaag gccaaaggaa ctgctacaat ttctcgctaa ctgctaaacg aaagtatctc    300

ataaggggaa cgttcattta tggtaattat gatggcctta atcagttacc ttcatttgat    360

ctttacatcg gcccaaataa atggactagt gtcagtattc caggcgtaag aaatgggtca    420

gtgtcagaga tgattcacgt actacgacaa gatcaccttc aaatctgtct agttaagacc    480

ggtgaaacta ccccccttcat ttcgtcccta gaacttaggc cccttaacaa taatacctat    540

gtgactaaat caggctcact aatagtcgtg gctcgtctct atttctcgcc taccccaccg    600

tttcttaggt atgacgagga tgttcacgat aggatctgga ttcccttctt agacaacaaa    660
```

-continued

```
aacagcctat tgagcaccga gctcagtgta gacacttcta acttctataa tgtaccacag    720

acggtggcca agactgcggc tgttccactt aatgctaccc agcccttaaa gataaattgg    780

tcactggatg atatcactag tcaaagttac atttatatgc attttgctga aatagagaat    840

ctagaggcta acgaaactag ggagttcaat attacttaca acggcggcga aaactggttc    900

agctacttcc gaccacctaa gtttagaatc accaccgtgt ataaccctgc cgccgtatcg    960

tcattggatg gcaatttcaa ctttacattt agcatgactg ggaattccac tcatccccca   1020

ttaattaacg gactagagat ttaccaggtg ctagagctgc cccagttgga cacctatcaa   1080

gatgaggtaa gcgccatgat gaatattaaa actatctatg ggctttcaaa acgctctagc   1140

tggcaaggtg acccttgcgc ccctgaactc tataggtggg aaggactgaa ttgtagctac   1200

cccaacttcg cccctcctca aattatttca ctgaacttaa gcggaagcaa ccttagtggc   1260

actattacta gcgatataag taagctcacg catctcaggg agttagacct ttccaataac   1320

gatttgtctg gagacatccc gtttgtgttt agcgatatga aaaaccttac catgattaat   1380

ctaagcggca acaaaaatct gaatagatcc gtgcccgaga cgctacagaa gagaatcgat   1440

aacaaaagtc tgaccttaat aagggatgag actggtaaga actctactaa tgttgtagcg   1500

atagcggcca gtgtggctag tgttttcgct gtattggtga ttctagcgat cgtgtttgtc   1560

gtaattcgta agaaacagag aactaacgaa gcatcagggc cacgttcttt cactaccggc   1620

accgtcaaga gcgacgcacg cagttcttct tcttctatta tcaccaaaga aagaaagttc   1680

acctattcgg aggtactgaa gatgactaag aatttcgagc gagtgctggg aaaaggaggc   1740

ttcggcactg tttatcatgg taatctagat gacacccagg tggccgttaa gatgctgtca   1800

cattccagcg ctcaaggcta taaggaattc aaggcagagg tggaactgct tctacgagtg   1860

caccatcgac acctcgtcgg actagttgga tattgtgacg atggcgacaa cctcgcccta   1920

atttacgagt atatggagaa gggcgacctt agggaaaata tgagtggtaa gcattcagtt   1980

aatgtgcttt cctgggaaac tcgcatgcag atagcggttg aggcggcgca gggtctggag   2040

tacctgcata atggttgcag accacctatg gtacacaggg acgttaaacc tacaaatatt   2100

ctacttaatg aacggagtca agccaaacta gctgatttcg gcctatcccg gtcatttccg   2160

gtcgacggag aatcccacgt tatgaccgtc gttgctggaa ctccgggtta cctggaccct   2220

gagtactaca ggacgaactg gctcagcgaa aagtctgacg tctactcttt tggggtggtg   2280

ctactggaga tcgtgacaaa ccaacccgtg atgaataaaa acagagaaag acctcacatt   2340

aacgagtggg tgatgttcat gctaacaaac ggcgacatta agtccatagt agaccctaag   2400

cttaatgagg attatgatac caatggagtt tggaaagtag tggagctagc tctagcctgt   2460

gttaatcctt cttcgagccg tcgtcctact atgccccacg tcgtgatgga actgaacgaa   2520

tgcttggccc tagagattga gcgtaagcag ggtagtcaag ctacctatat taaggaaagc   2580

gtcgagttca gcccgtcatc tgctagcgat ttcagtcctc tagctagatg a            2631
```

```
<210> SEQ ID NO 17
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
      /note="Nucleotide sequence RLK2, variant 13" /mol_type="unassigned
```

DNA"

<400> SEQUENCE: 17
atgcgatttc ttagtttctt aatcttcgtg ttcgcggtgc taggcctagt acaagctcaa 60
gatcagtccg gtttcattag cttagattgc ggactagtgc ctaccgaaat tacctacgtc 120
gagaaatcta cgaatattac atataggtca gacgcgacct atatcgatag cggcgtgcca 180
ggtaagatta atgaagtcta taggacgcaa tttcaacagc agatctgggc cttacgttct 240
ttccccgagg gtcagaggaa ttgttataac ttttctctaa ccgctaagcg taagtaccta 300
atcaggggca catttatcta cggaaactat gacggcctga accagctacc tagcttcgac 360
ctctatatcg gccctaacaa gtggacaagc gttagtatac caggcgttcg aaacggctca 420
gtcagcgaga tgattcatgt cctaaggcag gatcacctcc aaatttgcct agttaagacg 480
ggggagacta cccccttcat tagctctcta gagcttaggc cccttaataa taacacatac 540
gtgactaagt caggctcact aatagtggtc gctaggctct attttagccc taccccccct 600
ttccttcggt atgacgaaga tgtgcatgat aggatctgga tcccgttcct agataacaag 660
aactcacttc ttagcacaga gcttagcgtc gatacctcca atttctataa cgtgcctcaa 720
accgtggcga agaccgctgc tgttcctctc aacgctacgc agccccttaa gatcaactgg 780
tcactagacg acataactag tcagagctac atctatatgc acttcgccga gattgagaac 840
ctagaagcta atgagactag agagtttaac ataacctaca acggtggcga gaactggttt 900
agctacttcc gcccacctaa attccgtatc actaccgtct acaacccagc ggccgtaagt 960
agcttggatg gtaactttaa ctttaccttc agtatgaccg gtaactcaac ccaccccccc 1020
cttatcaacg gtctagaaat atatcaagtt ctagagctcc ctcaactaga cacctaccag 1080
gacgaagttt ccgctatgat gaatattaag actatatacg gccttagtaa aagatcaagc 1140
tggcagggtg acccatgcgc tccagaactc tacagatggg aaggtcttaa ctgtagctac 1200
cctaacttcg cgcctcctca gataatatcc cttaacctta gcgggagcaa tctttcgggc 1260
actattacca gcgatattag taagctgacg catcttaggg agctagactt aagtaataat 1320
gaccttagcg gcgatatccc gttcgtgttt tctgacatga agaatctgac catgattaac 1380
ctaagcggta ataaaaatct taatagatca gtgcccgaga ctcttcagaa gaggatagat 1440
aataaatcac taacacttat tcgggatgag actggtaaaa attctactaa cgtggtggcc 1500
atagctgcta gtgtcgccag cgttttcgct gtgttagtga tcctagcaat cgtgtttgtg 1560
gtgattagaa agaaacagcg cactaacgag gcgagcggac caagatcttt cactactggg 1620
actgttaaat cagacgctag gtcaagctct agctcgatca taactaaaga aaggaagttc 1680
acctatagcg aagtattaaa gatgacgaaa aacttcgagc gcgtgctagg taagggcgga 1740
ttcggaactg tttatcacgg taacctcgac gatacccagg tggccgtcaa aatgctcagt 1800
catagctcag ctcagggcta caaagagttt aaagccgagg ttgagctact actgagggtt 1860
caccaccggc atctagtggg actagtaggt tactgcgacg atggtgacaa cctagcccta 1920
atctatgagt atatggaaaa gggcgacctt agggagaaca tgtcggggaa acattcagtc 1980
aacgtgctaa gctgggaaac tcggatgcaa atagctgttg aagctgctca aggactagaa 2040
tatctccaca acggttgtag accacctatg gtgcatcgtg atgttaagcc tactaatatc 2100
ctacttaacg agcgttccca ggcaaaacta gctgacttcg gcttatcccg gtcatttcca 2160
gttgatggag aatctcacgt tatgaccgtt gttgctggaa ccccgggtta tctagatcca 2220
gagtactata ggactaattg gctgagcgag aaatcagacg tatatagttt cggagtagta 2280
ctactggaaa tcgtgactaa tcagcccgtg atgaacaaga atagagaacg ccctcacatt 2340
aacgagtggg tgatgttcat gcttactaac ggcgatatca agtcgatagt ggacccgaag 2400
cttaacgaag actatgatac taacggcgtt tggaaggttg tggagctagc tctagcctgc 2460
gttaacccta gtagcagcag aaggcctacc atgccgcacg tggtcatgga gcttaatgag 2520
tgcttagctc tagaaataga gcgtaagcaa ggtagtcaag ctacctacat aaaggagtcc 2580
gtcgagttta gccctagctc agctagcgac tttagtcctc tagctagata g 2631

<210> SEQ ID NO 18
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 14" /mol_type="unassigned DNA"

<400> SEQUENCE: 18
atgagattcc ttagcttcct catctttgtg ttcgccgtgc taggactagt tcaagctcaa 60
gatcaatcag gctttattag cctagattgc ggactagtgc ctaccgagat cacctatgtc 120
gagaagtcga ccaatatcac ctataggtca gacgctacat atatcgacag cggcgtgccc 180
ggaaagatta acgaagtcta ccgtacacag tttcagcagc aaatttgggc gcttcgatct 240
tttcccgaag gtcaaaggaa ttgctataac tttagcctaa ccgctaaacg taagtaccta 300
atccgcggca ccttcattta tgggaactac gacggcctta accagctacc tagctttgac 360
ctctatatcg gtcctaataa gtggactagc gtaagtattc caggcgttag gaacggctca 420
gttagcgaga tgatacatgt gctaagacaa gatcaccttc agatctgcct agttaaaacc 480
ggtgagacta ccccatttat tagcagcctg gagcttcgac cccttaataa caacacctat 540
gtaactaagt ctggttcact aatagtggtg gctaggctct acttctcacc taccccacct 600
ttccttcgat acgatgaaga cgttcatgat aggatttgga tccccttcct agacaacaag 660
aattcactac ttagcaccga gcttagcgtg gacactagta acttttataa cgtgccccag 720
actgtcgcta agacggctgc tgtcccactt aacgctactc agcccttaaa gattaactgg 780
tcattagacg atatcacttc acaatcctat atctatatgc acttcgccga gatagagaac 840
ctagaagcta acgagactag agagtttaat atcacttaca acggcggcga gaactggttt 900
agctacttcc gaccacctaa gtttagaatc actaccgtct ataacccagc ggccgttagt 960
agcctggatg gtaattttaa ctttaccttt agtatgaccg ggaactctac tcacccccct 1020
cttattaacg gcctagagat ttatcaagtc ctagagctac ctcaactaga tacctatcaa 1080
gatgaagtta gcgctatgat gaatattaaa actatctatg gcctgagtaa gaggtctagc 1140
tggcaaggtg atccttgtgc tccagaactc tataggtggg aggggcttaa ctgtagctac 1200
cctaatttcg cccctcccca aattatctca ttaaacttaa gcggctctaa ccttagtgga 1260
accatcacta gcgatataag taagctaact catcttaggg aattggacct ctcgaacaat 1320
gaccttagcg gtgacatccc cttcgtgttt agcgacatga agaatctaac actgatcaac 1380
ctaagcggta acaaaaatct taacagatcg gtgccggaaa ctcttcagaa aaggatagat 1440
aacaaatcac taacgttaat aagggacgag actggtaaga actctactaa cgtggtggct 1500

-continued

```
atagctgcca gtgtcgctag cgtcttcgct gtgctagtga tcctcgctat cgtgtttgtg   1560

gtcattagga agaagcaacg aactaacgag gcaagcggac ctagatcttt tactaccggc   1620

actgtgaagt cagacgccag gtctagctca agctctatca tcaccaagga acgtaaattc   1680

acctatagcg aagtgcttaa gatgaccaag aacttcgaga gagtgctagg taagggcgga   1740

ttcggaaccg tttatcatgg taacctagac gacactcagg tggccgttaa gatgcttagt   1800

cattcttcag cacagggcta taaggaattc aaagccgagg ttgaactact actccgcgtt   1860

caccataggc acctcgtagg acttgttggt tattgcgatg acggtgataa cctcgcccta   1920

atctacgagt atatggaaaa gggcgatctt agggagaata tgtcgggtaa gcactcagta   1980

aacgtgctat catgggaaac tcgtatgcaa atagccgttg aagctgctca gggactagag   2040

taccttcata acggttgtag gccacctatg gtgcataggg acgttaagcc aacaaatatt   2100

ctacttaacg agcgtagtca ggctaagcta gctgactttg gcttaagtag atcatttccg   2160

gttgacggtg agtctcatgt gatgaccgtt gttgcgggaa ccccaggtta cctagaccca   2220

gagtactatc gtacgaactg gctttcagag aagtcagatg tctactcttt cggggttgtg   2280

ctcctagaga tagtgacaaa tcaacccgtt atgaacaaga atagagagcg ccctcacatt   2340

aatgaatggg tgatgtttat gctaactaac ggcgacatta agtctatagt ggaccctaag   2400

cttaacgagg actacgacac taacggcgtt tggaaggttg tggaactagc tctcgcctgc   2460

gttaatccta gctctagtcg taggccgact atgccacatg tggtgatgga attaaacgag   2520

tgcctagctc tagagataga gcgaaagcaa ggtagtcagg ctacctatat caaggaatca   2580

gtcgagtttt cacctagctc agctagcgac ttctcgccac tagctaggtg a            2631
```

```
<210> SEQ ID NO 19
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
      /note="Nucleotide sequence RLK2, variant 15" /mol_type="unassigned
      DNA"

<400> SEQUENCE: 19

atgagattcc ttagtttctt aatcttcgtg ttcgccgtgc taggcctagt tcaagcacaa     60

gatcagtcgg gctttattag cctagattgc ggactagtgc ctaccgaaat tacctacgtc    120

gagaaatcga ctaatatcac ctataggtca gacgctacct atatcgatag cggcgtgccc    180

ggtaagatta acgaagtcta taggactcag tttcagcaac aaatctgggc gctgagatct    240

ttcccagagg gtcaaaggaa ttgctataat tttagcctaa ccgcaaagcg taagtacctc    300

attaggggca cctttattta cggtaactac gacggcctta atcagctacc tagcttcgac    360

ctctatatcg gccccaacaa gtggacttct gttagtattc ctggtgtaag gaacggttca    420

gtttcggaga tgattcatgt gctaaggcag gatcaccttc agatctgcct agttaagacc    480

ggagagacca ccccctttat aagctcacta gagcttaggc cctaaacaa caatacctac    540

gtgactaaat cagggtcact aatagtggtg gctaggctct actttagccc taccccaccg    600

tttcttaggt acgacgaaga tgttcatgat aggatctgga tcccctttct agataacaag    660

aactcactac ttagcaccga gcttagcgtg gacactagta atttctataa cgtgccgcag    720

accgtggcaa agactgctgc tgttccgctt aacgctactc agcctcttaa gattaactgg    780
```

```
tcgctcgacg atatcactag tcagtcctat atctatatgc acttcgccga gattgagaac    840

ctagaggcta acgagactag agagttcaac atcacttata acggcggcga gaattggttt    900

agctacttca ggccaccgaa gtttaggatc actaccgtct ataacccagc cgccgtaagt    960

tcacttgacg gtaacttcaa cttcactttt agtatgaccg gtaactcgac tcacccccca   1020

cttattaacg gcctagagat ctatcaggtg ctagaactac ctcaactaga cacgtaccag   1080

gacgaagtta gcgctatgat gaacattaag accatctacg gccttagtaa gcgctcttct   1140

tggcaaggtg atccttgcgc tccagagctc tatcggtggg aaggccttaa ctgtagctac   1200

cctaacttcg cccctcctca gattatctct cttaacctta gcggctctaa ccttagtggc   1260

actattacta gcgatattag taagctaact caccttaggg aactagacct tagtaacaac   1320

gaccttagcg ggatatacc  tttcgtcttc agcgatatga agaacctaac cctgattaac   1380

ctaagcggca acaagaacct taatagatca gtgcccgaga ctttacagaa acgaatagat   1440

aacaagagcc taaccctcat aagggacgag actggtaaaa actctactaa tgtcgtggct   1500

attgctgcta gtgtcgctag cgttttcgca gtgctagtca tcctagcgat agtgttcgta   1560

gtgattagga agaagcaacg cactaacgaa gctagcggac caagatcttt caccaccggc   1620

actgttaagt cagatgctag gtctagttct tcgtctatta taactaagga acgcaagttt   1680

acctatagcg aggttcttaa gatgactaag aacttcgaac gcgtgctagg taagggcgga   1740

ttcggaaccg tatatcacgg taacctagat gacacgcagg tggccgttaa gatgcttagt   1800

cactccagcg ctcagggcta taaggagttt aaggccgagg ttgagctact gcttagggtt   1860

caccaccgtc acttagtggg actagttggt tattgcgacg acggtgataa cctagccctg   1920

atctacgagt atatggaaaa gggcgacctt agggaaaata tgtctggtaa gcactcagtt   1980

aacgtgctaa gctgggagac taggatgcag atagctgttg aagctgctca gggactagag   2040

taccttcaca acggttgtag gccacctatg gttcacaggg acgttaagcc tactaatatc   2100

ctacttaacg agcgtagtca ggctaagcta gctgacttcg gcctttctag atcattccca   2160

gtggatggtg agtctcacgt tatgaccgtt gttgctggaa ccccagggta cctagatcca   2220

gagtactata ggactaactg gcttagcgag aagtcagacg tctactcttt cggagtggtg   2280

ctacttgaaa tagtgactaa tcagccggtg atgaacaaaa atagagagcg ccctcacatt   2340

aatgagtggg tgatgtttat gctaactaac ggcgatatta agagcatagt ggatccaaag   2400

cttaacgagg actacgacac taacggcgtt tggaaggttg tggaactagc tctagcctgc   2460

gttaaccctt cttctagtcg aagacctacg atgcctcacg tggtgatgga acttaacgag   2520

tgcctagctc tagaaatcga gcgtaagcaa ggaagtcaag ctacctatat taaggagtct   2580

gtcgaattta gcccttcctc agcaagcgat tttagtccac tagctaggtg a            2631
```

<210> SEQ ID NO 20
<211> LENGTH: 2631
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2631)
<223> OTHER INFORMATION: /organism="Artificial Sequence"
/note="Nucleotide sequence RLK2, variant 16" /mol_type="unassigned DNA"

<400> SEQUENCE: 20

-continued atgagattcc ttagtttctt aatcttcgtt ttcgccgtgc taggcctagt tcaagctcaa 60
gatcagtcag gcttcattag cctagattgc ggtctagtgc ctactgagat tacctacgtc 120
gagaagtcta caaatatcac ctataggtca gacgctacct atatcgatag cggcgtgccc 180
ggtaagatta atgaagtcta taggactcag tttcagcaac agatctgggc acttagatct 240
tttccagagg gtcagaggaa ctgctataat tttagcctaa ccgctaagcg taagtaccta 300
attaggggca cctttatcta cggtaactac gacggcctta atcagcttcc tagcttcgat 360
ctctatatcg ggcctaataa gtggactagc gttagtattc caggagttag gaacggttca 420
gttagcgaga tgattcacgt actgaggcag gatcaccttc aaatctgcct agttaagacc 480
ggagagacca cccctttat tagctcacta gagcttaggc cccttaacaa caacacctac 540
gtgactaagt caggctcact aatagttgtg gctaggctct actttagccc taccccacct 600
ttccttcgtt acgacgaaga tgtccacgat aggatctgga tacccttcct agataacaag 660
aactctctac ttagcaccga gcttagcgtg gacactagta acttctataa cgtcccacag 720
actgtggcta agactgctgc tgttccactt aacgccactc agccccttaa gattaactgg 780
tcacttgacg atatcactag tcagtcctat atctatatgc atttcgccga gatagagaac 840
ctagaggcta acgagactag agagttcaat atcacatata acggcggcga gaactggttt 900
agctacttta ggccacctaa gtttaggatc actaccgtct acaaccctgc cgccgtcagt 960
tcactagacg gtaactttaa tttcaccttt agtatgaccg gtaactctac tcacccccc 1020
ttgataaacg gcctagagat ctatcaggtg ctagagctac ctcagctaga cacctatcag 1080
gacgaagtta gcgctatgat gaacattaag actatctacg gccttagtaa gcgctctagc 1140
tggcaaggtg atccttgcgc tccagaactc tataggtggg aaggccttaa ctgtagctac 1200
cctaacttcg cccctcctca gattatctca cttaacctta gcggctctaa ccttagtggc 1260
actattacga gcgatattag taagctaact caccttaggg aactagacct aagtaacaac 1320
gaccttagcg gcgatatccc cttcgtgttc agcgatatga agaacctaac cctgattaac 1380
ctaagcggta acaagaacct taacagatca gtgcccgaga ctcttcagaa gaggatagat 1440
aacaagtcac taacccttat tagggacgag actggtaaaa actctactaa cgtggtggct 1500
atagctgcta gtgtcgctag cgttttcgct gtgctagtga tcttggctat agtgtttgtg 1560
gtgattagga agaagcagcg cactaacgaa gctagcggac ctagatcatt cactaccggc 1620
acggttaagt cagacgctcg ttctagctct agctctatta tcactaagga acgtaagttc 1680
acctatagcg aagtgcttaa gatgactaag aacttcgagc gcgttctagg taagggcgga 1740
ttcggaactg tttatcacgg taacctagac gacactcagg tggccgttaa gatgcttagt 1800
cactctagcg ctcagggcta taaggagttt aaggccgagg ttgagctgct acttagggtt 1860
caccatcgtc acctagtggg actagttggt tattgcgatg acggtgataa cctagcccta 1920
atctacgagt atatggaaaa gggcgacctt agggagaata tgagcggtaa gcattcagtt 1980
aatgtgctaa gctgggagac taggatgcag atagctgttg aagctgctca gggactagag 2040
taccttcaca acggttgtag gccaccgatg gtacacaggg acgttaagcc tactaatatc 2100
ctacttaacg agcgtagtca ggccaagcta gctgacttcg gccttagtag atcattccca 2160
gttgacggtg agtctcacgt tatgaccgtt gttgctggaa cgccaggtta cctagaccca 2220
gagtattata ggacaaattg gcttagcgaa aagtcagacg tttactcttt tggagtggtg 2280
ctactagaga tagtgactaa tcagcccgtg atgaacaaga atcgtgagcg ccctcacatc 2340
aacgagtggg tgatgtttat gctaactaac ggcgacatta agtcgatagt ggaccctaag 2400
cttaacgagg actacgacac aaacggcgtt tggaaggttg tggaactcgc tctagcctgc 2460
gttaacccga gctctagtag aaggcctact atgcctcacg tggtgatgga acttaacgag 2520
tgcctagctc tagagataga gcgtaaacaa ggcagtcaag cgacctatat taaggaatca 2580
gtcgagttta gccctagctc agctagcgac ttttctccac ttgctaggtg a 2631

<210> SEQ ID NO 21
<211> LENGTH: 2628
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2628)
<223> OTHER INFORMATION: /organism="Artificial Sequence"
/note="Nucleotide sequence RLK2, variant 17" /mol_type="unassigned
DNA"

<400> SEQUENCE: 21
atgaagtggg gcagcttcgt gatctacatg ttcgccgtgc tgggcggcat gaacgcccag 60
gagcagagcg gcttcatcag catcgagtgc ggcgtggtgc ccagcgacgc cacctacgtg 120
gacaagacca gcaacggcag ctacagaagc gacgcctgct acgccgacag cggcgtgccc 180
ggccacgcca acgaggtgtt cagaagccag tacaacaaca acggctggat ggccagaacc 240
taccccgaga tgaacagaaa ctgctacaac tactgcctgt gcgccaagag acactacctg 300
ggccacggca ccttcatctt cggcaactac gaggtggccc agcagggccc ctgctacgac 360
gtgtacgcca tccccaacag atacagctgc gtgtgcatcc ccatgctgag aaacggcagc 420
gtgagcgacg tgatccacat cgccaagaac gagcacctgc agggctgcct gggcaagacc 480
ggcgagagca ccccccttcat ctgcagcctg gacatcaagc ccctgaacaa ccagtgctgg 540
atcaccaagt gcggcagcct gatcgtggtg ctgaagctgt ggttctgccc ctgcccccc 600 ttcatgaagt acgacgagga gctgcacgag agagtgtggc tgccctacat ggacaacaag 660
aacagcgtgc tgtgcagcga cctgtgcatc gagagcacca acttcttcca ggtgcccaac 720
accgtggtga gaaccgtggc cggccccgcc aacgccaccc agcccatcca cgtgcagtgg 780
agcctggagg aggtgaccac caacagcttc atcttcctgc acttcgccga cgtggaccag 840
ctggacgcca acgagagcag agagttcaac atgtgcttcc agggcatcga ccagttcttc 900
acctacttca agcccccaa gtggcacatc accaccgtgt acaaccccgc cgccgtgacc 960
accgtggacg gcaactacaa ctactgctgg accatgaccg tgcagagcac ccacccccc 1020 ctgatgaacg tgctggacat cttcaacctg ctggagctgc ccaacatcga cacctacaac 1080
gacgaggtga ccgccatgat gaacatcaag accatctacg gcgcctgcaa gaagaccacc 1140
tacaacggcg agccctgcgg ccccgagctg tacagatggg acctgctgaa caccagctac 1200
cccaacttcg cccccccca gatcatcagc ctgaacctga gcggcagcaa cctgagcggc 1260
accatcacca gcgacatcag caagctgacc cacctgagag agctggacct gagcaacaac 1320
gacctgagcg gcgacatccc cttcgtgttc agcgacatga agaacctgac cctgatcaac 1380
ctgagcggca acaagaacct gaacagaagc gtgcccgaga ccctgcagaa gagaatcgac 1440
aacaagagcc tgaccctgat cagagacgag accggcaaga acagcaccaa cgtggtggcc 1500
atcgccgcca gcgtggccag cgtgttcgcc gtgctggtga tcctggccat cgtgttcgtg 1560
gtgatcagaa agaagcagag aaccaacgag gccagcggcc ccagaagctt caccaccggc 1620

```
accgtgaaga gcgacgccag aagcagcagc agcagcatca tcaccaagga gagaaagttc   1680

acctacagcg aggtgctgaa gatgaccaag aacttcgaga gagtgctggg caagggcggc   1740

ttcggcaccg tgtaccacgg caacctggac gacacccagg tggccgtgaa gatgctgagc   1800

cacagcaccg cccagggctg gaaggagtgg agagccgagg tggacgtggg cctgaaggtg   1860

caccacagac acggcgtggg catgatcggc ttcaccgagg acctggagaa cctgggcctg   1920

atctacgagt acatggacaa gggcgacctg cacgacaaca tgagcggcaa gcacaccgtg   1980

caggccctga gctgggagac cagactgaac atcgccgccg aggccgccaa cggcgtggac   2040

tacctgagac agggctgcag accccccgcc gtgcacaagg aggtgaagcc caccaacctg   2100

ctgctgaacg agagaagcca ggtgagactg ctggagttca tcctgagcag aagctacccc   2160

gtggacggcg agagccacgc catgtgcatg gtgatcggca cccccgtgtt cgccgagccc   2220

gagtactaca gaacccagtt cgccagcgac cacagcgagg gctacagctg ggccgccgtg   2280

ctgctggaca tcctgtgcaa ccagcccgtg atcaacagaa accacgagca ccccagagtg   2340

caggagttcg tggccttcat gctgaccaac ggcgagggca agagcatcgt ggagcccaag   2400

ctgaacgagg actacgacac caacggcgtg tggaaggtgg tggagctggc cctggcctgc   2460

gtgaacccca gcagcagcag aagacccacc atgccccacg tggtgatgga gctgaacgag   2520

tgcctggccc tggagatcga gagaaagcag ggcagccagg ccacctacat caaggagagc   2580

gtggagttca gccccagcag cgccagcgac ttcacccccc tggcccac               2628
```

<210> SEQ ID NO 22
<211> LENGTH: 876
<212> TYPE: PRT
<213> ORGANISM: Artificial Sequence
<220> FEATURE:
<223> OTHER INFORMATION: Amino acid sequence RLK2, variant 17

<400> SEQUENCE: 22

```
Met Lys Trp Gly Ser Phe Val Ile Tyr Met Phe Ala Val Leu Gly Gly
1               5                   10                  15

Met Asn Ala Gln Glu Gln Ser Gly Phe Ile Ser Ile Glu Cys Gly Val
            20                  25                  30

Val Pro Ser Asp Ala Thr Tyr Val Asp Lys Thr Ser Asn Gly Ser Tyr
        35                  40                  45

Arg Ser Asp Ala Cys Tyr Ala Asp Ser Gly Val Pro Gly His Ala Asn
    50                  55                  60

Glu Val Phe Arg Ser Gln Tyr Asn Asn Asn Gly Trp Met Ala Arg Thr
65                  70                  75                  80

Tyr Pro Glu Met Asn Arg Asn Cys Tyr Asn Tyr Cys Leu Cys Ala Lys
                85                  90                  95

Arg His Tyr Leu Gly His Gly Thr Phe Ile Phe Gly Asn Tyr Glu Val
            100                 105                 110

Ala Gln Gln Gly Pro Cys Tyr Asp Val Tyr Ala Ile Pro Asn Arg Tyr
        115                 120                 125

Ser Cys Val Cys Ile Pro Met Leu Arg Asn Gly Ser Val Ser Asp Val
    130                 135                 140

Ile His Ile Ala Lys Asn Glu His Leu Gln Gly Cys Leu Gly Lys Thr
145                 150                 155                 160

Gly Glu Ser Thr Pro Phe Ile Cys Ser Leu Asp Ile Lys Pro Leu Asn
                165                 170                 175

Asn Gln Cys Trp Ile Thr Lys Cys Gly Ser Leu Ile Val Val Leu Lys
            180                 185                 190
```

```
Leu Trp Phe Cys Pro Cys Pro Pro Phe Met Lys Tyr Asp Glu Glu Leu
        195                 200                 205

His Glu Arg Val Trp Leu Pro Tyr Met Asp Asn Lys Asn Ser Val Leu
    210                 215                 220

Cys Ser Asp Leu Cys Ile Glu Ser Thr Asn Phe Phe Gln Val Pro Asn
225                 230                 235                 240

Thr Val Val Arg Thr Val Ala Gly Pro Ala Asn Ala Thr Gln Pro Ile
                245                 250                 255

His Val Gln Trp Ser Leu Glu Glu Val Thr Thr Asn Ser Phe Ile Phe
            260                 265                 270

Leu His Phe Ala Asp Val Asp Gln Leu Asp Ala Asn Glu Ser Arg Glu
        275                 280                 285

Phe Asn Met Cys Phe Gln Gly Ile Asp Gln Phe Phe Thr Tyr Phe Lys
    290                 295                 300

Pro Pro Lys Trp His Ile Thr Thr Val Tyr Asn Pro Ala Ala Val Thr
305                 310                 315                 320

Thr Val Asp Gly Asn Tyr Asn Tyr Cys Trp Thr Met Thr Val Gln Ser
                325                 330                 335

Thr His Pro Pro Leu Met Asn Val Leu Asp Ile Phe Asn Leu Leu Glu
            340                 345                 350

Leu Pro Asn Ile Asp Thr Tyr Asn Asp Glu Val Thr Ala Met Met Asn
        355                 360                 365

Ile Lys Thr Ile Tyr Gly Ala Cys Lys Lys Thr Thr Tyr Asn Gly Glu
    370                 375                 380

Pro Cys Gly Pro Glu Leu Tyr Arg Trp Asp Leu Leu Asn Thr Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560

Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
            580                 585                 590

Gln Val Ala Val Lys Met Leu Ser His Ser Thr Ala Gln Gly Trp Lys
        595                 600                 605
```

Glu Trp Arg Ala Glu Val Asp Val Gly Leu Lys Val His His Arg His
    610                 615                 620

Gly Val Gly Met Ile Gly Phe Thr Glu Asp Leu Glu Asn Leu Gly Leu
625                 630                 635                 640

Ile Tyr Glu Tyr Met Asp Lys Gly Asp Leu His Asp Asn Met Ser Gly
                645                 650                 655

Lys His Thr Val Gln Ala Leu Ser Trp Glu Thr Arg Leu Asn Ile Ala
            660                 665                 670

Ala Glu Ala Ala Asn Gly Val Asp Tyr Leu Arg Gln Gly Cys Arg Pro
        675                 680                 685

Pro Ala Val His Lys Glu Val Lys Pro Thr Asn Leu Leu Leu Asn Glu
    690                 695                 700

Arg Ser Gln Val Arg Leu Leu Glu Phe Ile Leu Ser Arg Ser Tyr Pro
705                 710                 715                 720

Val Asp Gly Glu Ser His Ala Met Cys Met Val Ile Gly Thr Pro Val
                725                 730                 735

Phe Ala Glu Pro Glu Tyr Tyr Arg Thr Gln Phe Ala Ser Asp His Ser
            740                 745                 750

Glu Gly Tyr Ser Trp Ala Ala Val Leu Leu Asp Ile Leu Cys Asn Gln
        755                 760                 765

Pro Val Ile Asn Arg Asn His Glu His Pro Arg Val Gln Glu Phe Val
    770                 775                 780

Ala Phe Met Leu Thr Asn Gly Glu Gly Lys Ser Ile Val Glu Pro Lys
785                 790                 795                 800

Leu Asn Glu Asp Tyr Asp Thr Asn Gly Val Trp Lys Val Val Glu Leu
                805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Thr Pro Leu Ala His
865                 870                 875

<210> SEQ ID NO 23
<211> LENGTH: 2628
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2628)
<223> OTHER INFORMATION: /organism="Artificial Sequence"
      /note="Nucleotide sequence RLK2, variant 18" /mol_type="unassigned
      DNA"

<400> SEQUENCE: 23
atgaagttcc tgagctacct gggcttcatg ttcgccgccg tgggcctggt gcaggcccag 60
gaccagtgcg gcttcgtgtg cctggactgc ggcgccggcc ccaccgagat gacctacatg 120
gacagaagca gccagatcac ctaccacacc gacgccacct acatcgagag cggcgtgccc 180
gccagaatca acgaggtgta cagaagccag ttccagcagc agatgttcgc cctgcactgc 240
ttccccgagg gcaacagaaa ctgctaccag ttcaccctga ccgccaagag aaagtacctg 300
atcaaggtga cctgggccta cggccagtgg gagggcctgc agcaggcccc cagcttcgac 360

-continued

```
atgtggatcc tgcccaacaa gtggtgcagc gtgagcggcc ccgtggtgca caacgccacc    420
gtgtgcgaga tgggcaaggt gctgagaaac gaccacctgc aggcctgcct ggtgaagacc    480
gtggacagca ccccttcat cagcagcctg gagctgagac ccgtgcagca gaactgctac     540
gtgaccaagt gcgccagcct gatcgccgtg gccagactgt ggttcagccc caccccccc     600
ttcctgagat gggacgagga catgcacgac agagtgtgga tcccctggct ggagcagaag    660
cagaccatcc tgagcaccga cctgagcgtg gagaccagca actggtacaa cgtgccccag    720
agcgccatgc acaccgccgc cctgcccatc aacgccacca accccatcaa gatccagtgg    780
agcgtggacg acatcaccag ccagagctac atctacatgc actacatcga gatcgagaac    840
gccgacgccc aggagagcaa ggagtggcag atcaccttca acggcggcga gaactggttc    900
tgctggtgga gacccccaa gtacagaggc accaccctgt acaacccgc catggtgtgc      960
accgtggacg gccagttcca gttcaccttc tgcatgaccg gcaacagcag ccacccccc    1020
atgatcaacg tgatggagat ctggcaggcc atcgacctgc cccagctgga ctgcttcaac   1080
gaggaggtgt gcggcgccat gcaggccaag tgcatctacg gcatgaccaa gagatgctgc   1140
ttccagctgg acccctgcgc ccccgagatc tggagatggg aggccctgca gagcagctac   1200
cccaacttcg ccccccccca gatcatcagc ctgaacctga gcggcagcaa cctgagcggc   1260
accatcacca gcgacatcag caagctgacc cacctgagag agctggacct gagcaacaac   1320
gacctgagcg gcgacatccc cttcgtgttc agcgacatga agaacctgac cctgatcaac   1380
ctgagcggca acaagaacct gaacagaagc gtgcccgaga ccctgcagaa gagaatcgac   1440
aacaagagcc tgaccctgat cagagacgag accggcaaga acagcaccaa cgtggtggcc   1500
atcgccgcca gcgtggccag cgtgttcgcc gtgctggtga tcctggccat cgtgttcgtg   1560
gtgatcagaa agaagcagag aaccaacgag gccagcggcc ccagaagctt caccaccggc   1620
accgtgaaga gcgacgccag aagcagcagc agcagcatca tcaccaagga gagaaagttc   1680
acctacagcg aggtgctgaa gatgaccaag aacttcgaga gagtgctggg caagggcggc   1740
ttcggcaccg tgtaccacgg caacctggac gacacccagg tggccgtgaa gatgctgagc   1800
cacagcaccc tgaacggcta caaggagttc aagatggacg tggagctgat cctgagagtg   1860
caccacagaa gactggtggg cctggtgggc tacagcgacg agggcgagaa cctggccatc   1920
gtgttcgact acatggagag agccgacatc agagagaaca tgagcatcag aagaaccgtg   1980
aacctgatca gctgggagac cagaatccag atcgccatgg aggccgtgca gggcatcgac   2040
tacctgagaa acgccagcag accccccatg gtgaagagag aggtgcaccc cagcaacatc   2100
ctgatcaacg agagaagcaa cgcccacctg gccgactggg gcctgagcag aagcttcccc   2160
gtggagggcg agagccacgt gatcaccgtg ggcgccggca cccccgcctt cctggagccc   2220
gagtactaca gaaccaactg gctgaccgag aagtgcgacc tgtggagctg gggcctggtg   2280
atcctggaca tcgtgaccaa ccagcccgtg ggccagaaga acaaggagaa gccccacatc   2340
aacgactgga tgatgtacat gctgacccag ggcgagggca agagcgccgt ggaccccaag   2400
ctgaacgagg actacgacac caacggcgtg tggaaggtgg tggagctggc cctggcctgc   2460
gtgaacccca gcagcagcag aagacccacc atgccccacg tggtgatgga gctgaacgag   2520
tgcctggccc tggagatcga gagaaagcag ggcagccagg ccacctacat caaggagagc   2580
gtggagttca gccccagcag cgccagcgac ttcacccccca tggtgaga               2628
```

<210> SEQ ID NO 24
<211> LENGTH: 876

<212> TYPE: PRT
<213> ORGANISM: Artificial Sequence
<220> FEATURE:
<223> OTHER INFORMATION: Amino acid sequence RLK2, variant 18

<400> SEQUENCE: 24

```
Met Lys Phe Leu Ser Tyr Leu Gly Phe Met Phe Ala Ala Val Gly Leu
1               5                   10                  15

Val Gln Ala Gln Asp Gln Cys Gly Phe Val Cys Leu Asp Cys Gly Ala
            20                  25                  30

Gly Pro Thr Glu Met Thr Tyr Met Asp Arg Ser Ser Gln Ile Thr Tyr
        35                  40                  45

His Thr Asp Ala Thr Tyr Ile Glu Ser Gly Val Pro Ala Arg Ile Asn
    50                  55                  60

Glu Val Tyr Arg Ser Gln Phe Gln Gln Gln Met Phe Ala Leu His Cys
65                  70                  75                  80

Phe Pro Glu Gly Asn Arg Asn Cys Tyr Gln Phe Thr Leu Thr Ala Lys
                85                  90                  95

Arg Lys Tyr Leu Ile Lys Val Thr Trp Ala Tyr Gly Gln Trp Glu Gly
            100                 105                 110

Leu Gln Gln Ala Pro Ser Phe Asp Met Trp Ile Leu Pro Asn Lys Trp
        115                 120                 125

Cys Ser Val Ser Gly Pro Val Val His Asn Ala Thr Val Cys Glu Met
    130                 135                 140

Gly Lys Val Leu Arg Asn Asp His Leu Gln Ala Cys Leu Val Lys Thr
145                 150                 155                 160

Val Asp Ser Thr Pro Phe Ile Ser Ser Leu Glu Leu Arg Pro Val Gln
                165                 170                 175

Gln Asn Cys Tyr Val Thr Lys Cys Ala Ser Leu Ile Ala Val Ala Arg
            180                 185                 190

Leu Trp Phe Ser Pro Thr Pro Pro Phe Leu Arg Trp Asp Glu Asp Met
        195                 200                 205

His Asp Arg Val Trp Ile Pro Trp Leu Glu Gln Lys Gln Thr Ile Leu
    210                 215                 220

Ser Thr Asp Leu Ser Val Glu Thr Ser Asn Trp Tyr Asn Val Pro Gln
225                 230                 235                 240

Ser Ala Met His Thr Ala Ala Leu Pro Ile Asn Ala Thr Asn Pro Ile
                245                 250                 255

Lys Ile Gln Trp Ser Val Asp Asp Ile Thr Ser Gln Ser Tyr Ile Tyr
            260                 265                 270

Met His Tyr Ile Glu Ile Glu Asn Ala Asp Ala Gln Glu Ser Lys Glu
        275                 280                 285

Trp Gln Ile Thr Phe Asn Gly Gly Glu Asn Trp Phe Cys Trp Trp Arg
    290                 295                 300

Pro Pro Lys Tyr Arg Gly Thr Thr Leu Tyr Asn Pro Ala Met Val Cys
305                 310                 315                 320

Thr Val Asp Gly Gln Phe Gln Phe Thr Phe Cys Met Thr Gly Asn Ser
                325                 330                 335

Ser His Pro Pro Met Ile Asn Val Met Glu Ile Trp Gln Ala Ile Asp
            340                 345                 350

Leu Pro Gln Leu Asp Cys Phe Asn Glu Glu Val Cys Gly Ala Met Gln
        355                 360                 365

Ala Lys Cys Ile Tyr Gly Met Thr Lys Arg Cys Cys Phe Gln Leu Asp
    370                 375                 380
```

```
Pro Cys Ala Pro Glu Ile Trp Arg Trp Glu Ala Leu Gln Ser Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560

Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
            580                 585                 590

Gln Val Ala Val Lys Met Leu Ser His Ser Thr Leu Asn Gly Tyr Lys
        595                 600                 605

Glu Phe Lys Met Asp Val Glu Leu Ile Leu Arg Val His His Arg Arg
    610                 615                 620

Leu Val Gly Leu Val Gly Tyr Ser Asp Glu Gly Glu Asn Leu Ala Ile
625                 630                 635                 640

Val Phe Asp Tyr Met Glu Arg Ala Asp Ile Arg Glu Asn Met Ser Ile
                645                 650                 655

Arg Arg Thr Val Asn Leu Ile Ser Trp Glu Thr Arg Ile Gln Ile Ala
            660                 665                 670

Met Glu Ala Val Gln Gly Ile Asp Tyr Leu Arg Asn Ala Ser Arg Pro
        675                 680                 685

Pro Met Val Lys Arg Glu Val His Pro Ser Asn Ile Leu Ile Asn Glu
    690                 695                 700

Arg Ser Asn Ala His Leu Ala Asp Trp Gly Leu Ser Arg Ser Phe Pro
705                 710                 715                 720

Val Glu Gly Glu Ser His Val Ile Thr Val Gly Ala Gly Thr Pro Ala
                725                 730                 735

Phe Leu Glu Pro Glu Tyr Tyr Arg Thr Asn Trp Leu Thr Glu Lys Cys
            740                 745                 750

Asp Leu Trp Ser Trp Gly Leu Val Ile Leu Asp Ile Val Thr Asn Gln
        755                 760                 765

Pro Val Gly Gln Lys Asn Lys Glu Lys Pro His Ile Asn Asp Trp Met
    770                 775                 780

Met Tyr Met Leu Thr Gln Gly Glu Gly Lys Ser Ala Val Asp Pro Lys
785                 790                 795                 800

Leu Asn Glu Asp Tyr Asp Thr Asn Gly Val Trp Lys Val Val Glu Leu
```

```
                805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Thr Pro Met Val Arg
865                 870                 875


<210> SEQ ID NO 25
<211> LENGTH: 2628
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2628)
<223> OTHER INFORMATION: /organism="Artificial Sequence"
      /note="Nucleotide sequence RLK2, variant 19" /mol_type="unassigned
      DNA"

<400> SEQUENCE: 25

atgcactacc tgagctggct gatgttcctg tacgccgtgc tgggcctggt gcaggcccag      60

gaccagagcg gcttcatcag cctggactgc ggcctgatcc ccaccgagat cacctacggc     120

gagaagagca cccagctgac ctacaagagc gacgtgacct acatcgacag cggcgtgccc     180

ggcagaatca acgacgtgta ccacacccag ttccagaaca acatctgggg catcagatgc     240

ttccccgacg gccagagaaa cacctggaac tggagcctgt gcgccaagag aaagtacctg     300

atcagaggca ccttcgccta cggccagtac gacgccggca acaacgcccc cagcttcgac     360

gtgtacatcg tgcccaacag atggtgcagc gtgagcgtgc ccggcggcag acagctgtgc     420

gtgtgcgaga tgatcagagt gctgagacag gaccacatgc agatcagcgt ggtgaagtgc     480

ggcgagacca ccccccttcat cagcagcctg gagctgagac ccatcaacca gaacaccttc     540

gtgaccagaa gcggcaccct gatcatgggc gccaagctgt ggttcagccc ctgcccccccc     600

ttcctgaagt acgaggacga gctgcacgac cacctgtggg tgcccttcct ggacaaccac     660

cagagcctgc tgtgcaccga cctgagcgtg gagaccagca acttctggca gctgccccag     720

accgtggcca agaccgccgt ggtgcccctg caggtgacca accccctgaa gatccagtac     780

tgcctggacg acatcaccag ccagtgctac atctggatga gattcgccga cgtggagaac     840

atggagatca acgacaccag agagttcaac atcaccttca acggcggcga gaactggttc     900

agctggtggc acccccccca ctggagaatc accaccggct acaaccccgc cgccgtgagc     960

agcatcgacg gcaacttcaa cttcaccttc tgcatgaccg gcaacagcac ccacccccccc    1020

ctggtgaacg gcgccgacct gtaccaggtg ctggagctgc cccagctgga ctgctggcag    1080

gacgaggtga ccgccatgat gaacgccaag tgcatcttcg gcctgagcaa gagaagcagc    1140

tggcagggcg acccctgcgc cccgacctg tggagattcg acatgggcca gtgcagctac     1200

cccaacttcg cccccccccca gatcatcagc ctgaacctga gcggcagcaa cctgagcggc    1260

accatcacca gcgacatcag caagctgacc cacctgagag agctggacct gagcaacaac    1320

gacctgagcg gcgacatccc cttcgtgttc agcgacatga agaacctgac cctgatcaac    1380

ctgagcggca acaagaacct gaacagaagc gtgcccgaga ccctgcagaa gagaatcgac    1440

aacaagagcc tgaccctgat cagagacgag accggcaaga acagcaccaa cgtggtggcc    1500
```

```
atcgccgcca gcgtggccag cgtgttcgcc gtgctggtga tcctggccat cgtgttcgtg   1560

gtgatcagaa agaagcagag aaccaacgag gccagcggcc ccagaagctt caccaccggc   1620

accgtgaaga gcgacgccag aagcagcagc agcagcatca tcaccaagga gagaaagttc   1680

acctacagcg aggtgctgaa gatgaccaag aacttcgaga gagtgctggg caagggcggc   1740

ttcggcaccg tgtaccacgg caacctggac gacacccagg tggccgtgaa gatgctgagc   1800

cacagcagcg cccagatgtg gaaggacttc aaggccgagg tggagctgct gctgagactg   1860

caccacagac acctggtggg cctggtgatc tactgcgagg acggcgacaa cctggccggc   1920

atctacgagt acgtggagaa ggtggacatc aaggagaaca tgagcggcaa gaagagcgtg   1980

aacctgctga gctacgagtg ccacgccaac atcgccgtgg aggccgccca gatgctggag   2040

ttcctgcaca acctgtgcag accccccatg gtgcaccacg aggtgcaccc caccaacatc   2100

gccctgcagg acaagtgcca gggcaagctg gccgacttca tgctgagcca ctgcttcccc   2160

gtggacggcg acagccacgt gatgagcgcc gtggccggca cccccggcta catggacccc   2220

gagtacttca gaaccaactg gctgagcgag cacagcgaga tctggagctt cggcgtgggc   2280

ctgggcgaca tcgtgaccaa ccagcccgcc atgcagaagc agcacgagag accccacatc   2340

aacgagttcg tgatgttcat gatcaccaac ggcgacatca gaagcggcgc cgaccccaag   2400

ctgaacgagg actacgacac caacggcgtg tggaaggtgg tggagctggc cctggcctgc   2460

gtgaacccca gcagcagcag aagacccacc atgccccacg tggtgatgga gctgaacgag   2520

tgcctggccc tggagatcga gagaaagcag ggcagccagg ccacctacat caaggagagc   2580

gtggagttca gccccagcag cgccagcgac ttcagccccc tggccaga                2628
```

<210> SEQ ID NO 26
<211> LENGTH: 876
<212> TYPE: PRT
<213> ORGANISM: Artificial Sequence
<220> FEATURE:
<223> OTHER INFORMATION: Amino acid sequence RLK2, variant 19

<400> SEQUENCE: 26

```
Met His Tyr Leu Ser Trp Leu Met Phe Leu Tyr Ala Val Leu Gly Leu
1               5                   10                  15

Val Gln Ala Gln Asp Gln Ser Gly Phe Ile Ser Leu Asp Cys Gly Leu
            20                  25                  30

Ile Pro Thr Glu Ile Thr Tyr Gly Glu Lys Ser Thr Gln Leu Thr Tyr
        35                  40                  45

Lys Ser Asp Val Thr Tyr Ile Asp Ser Gly Val Pro Gly Arg Ile Asn
    50                  55                  60

Asp Val Tyr His Thr Gln Phe Gln Asn Asn Ile Trp Gly Ile Arg Cys
65                  70                  75                  80

Phe Pro Asp Gly Gln Arg Asn Thr Trp Asn Trp Ser Leu Cys Ala Lys
                85                  90                  95

Arg Lys Tyr Leu Ile Arg Gly Thr Phe Ala Tyr Gly Gln Tyr Asp Ala
            100                 105                 110

Gly Asn Asn Ala Pro Ser Phe Asp Val Tyr Ile Val Pro Asn Arg Trp
        115                 120                 125

Cys Ser Val Ser Val Pro Gly Gly Arg Gln Leu Cys Val Cys Glu Met
    130                 135                 140

Ile Arg Val Leu Arg Gln Asp His Met Gln Ile Ser Val Val Lys Cys
145                 150                 155                 160
```

```
Gly Glu Thr Thr Pro Phe Ile Ser Ser Leu Glu Leu Arg Pro Ile Asn
                165                 170                 175

Gln Asn Thr Phe Val Thr Arg Ser Gly Thr Leu Ile Met Gly Ala Lys
            180                 185                 190

Leu Trp Phe Ser Pro Cys Pro Pro Phe Leu Lys Tyr Glu Asp Glu Leu
        195                 200                 205

His Asp His Leu Trp Val Pro Phe Leu Asp Asn His Gln Ser Leu Leu
    210                 215                 220

Cys Thr Asp Leu Ser Val Glu Thr Ser Asn Phe Trp Gln Leu Pro Gln
225                 230                 235                 240

Thr Val Ala Lys Thr Ala Val Val Pro Leu Gln Val Thr Asn Pro Leu
                245                 250                 255

Lys Ile Gln Tyr Cys Leu Asp Asp Ile Thr Ser Gln Cys Tyr Ile Trp
            260                 265                 270

Met Arg Phe Ala Asp Val Glu Asn Met Glu Ile Asn Asp Thr Arg Glu
        275                 280                 285

Phe Asn Ile Thr Phe Asn Gly Gly Glu Asn Trp Phe Ser Trp Trp His
    290                 295                 300

Pro Pro His Trp Arg Ile Thr Thr Gly Tyr Asn Pro Ala Ala Val Ser
305                 310                 315                 320

Ser Ile Asp Gly Asn Phe Asn Phe Thr Phe Cys Met Thr Gly Asn Ser
                325                 330                 335

Thr His Pro Pro Leu Val Asn Gly Ala Asp Leu Tyr Gln Val Leu Glu
            340                 345                 350

Leu Pro Gln Leu Asp Cys Trp Gln Asp Glu Val Thr Ala Met Met Asn
        355                 360                 365

Ala Lys Cys Ile Phe Gly Leu Ser Lys Arg Ser Ser Trp Gln Gly Asp
    370                 375                 380

Pro Cys Ala Pro Asp Leu Trp Arg Phe Asp Met Gly Gln Cys Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560

Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
```

```
            580                 585                 590

Gln Val Ala Val Lys Met Leu Ser His Ser Ser Ala Gln Met Trp Lys
        595                 600                 605

Asp Phe Lys Ala Glu Val Glu Leu Leu Leu Arg Leu His His Arg His
    610                 615                 620

Leu Val Gly Leu Val Ile Tyr Cys Glu Asp Gly Asp Asn Leu Ala Gly
625                 630                 635                 640

Ile Tyr Glu Tyr Val Glu Lys Val Asp Ile Lys Glu Asn Met Ser Gly
                645                 650                 655

Lys Lys Ser Val Asn Leu Leu Ser Tyr Glu Cys His Ala Asn Ile Ala
            660                 665                 670

Val Glu Ala Ala Gln Met Leu Glu Phe Leu His Asn Leu Cys Arg Pro
        675                 680                 685

Pro Met Val His His Glu Val His Pro Thr Asn Ile Ala Leu Gln Asp
    690                 695                 700

Lys Cys Gln Gly Lys Leu Ala Asp Phe Met Leu Ser His Cys Phe Pro
705                 710                 715                 720

Val Asp Gly Asp Ser His Val Met Ser Ala Val Ala Gly Thr Pro Gly
                725                 730                 735

Tyr Met Asp Pro Glu Tyr Phe Arg Thr Asn Trp Leu Ser Glu His Ser
            740                 745                 750

Glu Ile Trp Ser Phe Gly Val Gly Leu Gly Asp Ile Val Thr Asn Gln
        755                 760                 765

Pro Ala Met Gln Lys Gln His Glu Arg Pro His Ile Asn Glu Phe Val
    770                 775                 780

Met Phe Met Ile Thr Asn Gly Asp Ile Arg Ser Gly Ala Asp Pro Lys
785                 790                 795                 800

Leu Asn Glu Asp Tyr Asp Thr Asn Gly Val Trp Lys Val Val Glu Leu
                805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Ser Pro Leu Ala Arg
865                 870                 875
```

<210> SEQ ID NO 27
<211> LENGTH: 2628
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2628)
<223> OTHER INFORMATION: /organism="Artificial Sequence"
/note="Nucleotide sequence RLK2, variant 20" /mol_type="unassigned
DNA"

<400> SEQUENCE: 27

```
atgagattcg tgagctgggt gatcttcgtg ttcgccgtgc tgggcggcgt gcagggcaac     60

gaccagagcg gctggatgag catcgactgc atgggcgtgc ccaccgagat cacctacgtg    120

gagagaagca ccaacatcac ctacagaagc gacgccacct acatcgacag cggcgtgccc    180

ggccacctga acgacgtgtg gagaacccag ttccagaacc agatcttcgc cgccagaagc    240
```

```
ttccccgagg gccagagaaa ctgctacaac tggaccctga ccatcaagag acactacctg    300
atcagaggca ccttcatcta cggcaactgg gacggcctga accagatccc ctgcttcgac    360
ctgtacatcg gccccaacaa gtggaccagc ggctgcatcc ccggcgtgag acagatgagc    420
gtgaccgaca tgatccacgt gctgagacag gaccacctgc agatctgcgc cgtgaagtgc    480
ggcgagacca ccccccttcat cagcagcctg gagctgagac ccctgaacca gaacaccttc    540
gtgaccaaga gcggcagcct ggtggtggtg gccaagctgt acttcagccc cacccccccc    600
ttcctgaagt acgacgagga cgtgagagac agaatcttca tccccttcct ggacaacaag    660
aacagcgccc tgagcagcga gctgagcgtg gacacctgca acttctacca ggtgccccag    720
accgtggcca agaccgccat cgtgcccctg aacctgacca accccggcaa gctgcagtgg    780
agcatcgacg acatcaccag ccagtgctac atctacatgc acttcgccga gatggagcag    840
ctggaggccc aggagaccag agagttcaac atctgctaca acggcggcga gcagttcttc    900
agctacttca gacccccccaa gttccacatc accaccctgt acaaccccgc cgccatgtgc    960
agcatggagg gcaacttcaa cttcacctgg agcatgaccg ccaacagcac caagcccccc   1020
ctgatcaacg gcctggacat ctggcaggtg ctggacatcc ccaacctgga cacctaccag   1080
gacgaggtga gcgccctgat gcagatcaag accatctggg gcctgagcag aagaagcagc   1140
ttccagggcg accccagcct gcccgacgtg tacagatggg aggtgctgca gtgcagctac   1200
cccaacttcg cccccccccca gatcatcagc ctgaacctga gcggcagcaa cctgagcggc   1260
accatcacca gcgacatcag caagctgacc cacctgagag agctggacct gagcaacaac   1320
gacctgagcg gcgacatccc cttcgtgttc agcgacatga agaacctgac cctgatcaac   1380
ctgagcggca acaagaacct gaacagaagc gtgcccgaga ccctgcagaa gagaatcgac   1440
aacaagagcc tgaccctgat cagagacgag accggcaaga acagcaccaa cgtggtggcc   1500
atcgccgcca gcgtggccag cgtgttcgcc gtgctggtga tcctggccat cgtgttcgtg   1560
gtgatcagaa agaagcagag aaccaacgag gccagcggcc ccagaagctt caccaccggc   1620
accgtgaaga gcgacgccag aagcagcagc agcagcatca tcaccaagga gagaaagttc   1680
acctacagcg aggtgctgaa gatgaccaag aacttcgaga gagtgctggg caagggcggc   1740
ttcggcaccg tgtaccacgg caacctggac gacacccagg tggccgtgaa gatgctgagc   1800
cacagcagcg cccagggcta caaggagtgg aagggcgagg tggaggccct gctgagaatg   1860
caccacaaga agctggccgg cctggtgggc ttctgcgacg acggcgacaa cctggccctg   1920
atctacgagt ggatggacaa gatggagatg agagagaaca tgagcggcaa gcactgcgtg   1980
aacgtgctga gctgggagac cagaatgcag atcatggtgg acgccgccca gggcctggag   2040
tacctgagaa acggctgcag accccccatg gtgcacagag acgtgagacc cagcaacatc   2100
ctgctgaacg agagaagcca gggcaagctg ctggactacg gcctgagcaa gagcttcccc   2160
gtggacggcg agacccacgt gatgaccgtg gtggccggca cccccggcta cctggacccc   2220
gagtactaca gaaccaactt cctgagcgag aagtgcgagg tgtacagctt catggtggtg   2280
gtgctggaga tcgtgaccaa caaccccgtg ctgcagaagc agaaggacag accccacatc   2340
aacgagtggc tggtgtggat gctgaccaac gccgacatca agaccatcgt ggagcccaag   2400
ctgaacgagg actacgacac caacggcgtg tggaaggtgg tggagctggc cctggcctgc   2460
gtgaacccca gcagcagcag aagacccacc atgccccacg tggtgatgga gctgaacgag   2520
tgcctggccc tggagatcga gagaaagcag ggcagccagg ccacctacat caaggagagc   2580
```

-continued

```
gtggagttca gccccagcag cgccagcgac ttcagccccc tggccaga             2628


<210> SEQ ID NO 28
<211> LENGTH: 876
<212> TYPE: PRT
<213> ORGANISM: Artificial Sequence
<220> FEATURE:
<223> OTHER INFORMATION: Amino acid sequence RLK2, variant 20

<400> SEQUENCE: 28

Met Arg Phe Val Ser Trp Val Ile Phe Val Phe Ala Val Leu Gly Gly
1               5                   10                  15

Val Gln Gly Asn Asp Gln Ser Gly Trp Met Ser Ile Asp Cys Met Gly
            20                  25                  30

Val Pro Thr Glu Ile Thr Tyr Val Glu Arg Ser Thr Asn Ile Thr Tyr
        35                  40                  45

Arg Ser Asp Ala Thr Tyr Ile Asp Ser Gly Val Pro Gly His Leu Asn
    50                  55                  60

Asp Val Trp Arg Thr Gln Phe Gln Asn Gln Ile Phe Ala Ala Arg Ser
65                  70                  75                  80

Phe Pro Glu Gly Gln Arg Asn Cys Tyr Asn Trp Thr Leu Thr Ile Lys
                85                  90                  95

Arg His Tyr Leu Ile Arg Gly Thr Phe Ile Tyr Gly Asn Trp Asp Gly
            100                 105                 110

Leu Asn Gln Ile Pro Cys Phe Asp Leu Tyr Ile Gly Pro Asn Lys Trp
        115                 120                 125

Thr Ser Gly Cys Ile Pro Gly Val Arg Gln Met Ser Val Thr Asp Met
    130                 135                 140

Ile His Val Leu Arg Gln Asp His Leu Gln Ile Cys Ala Val Lys Cys
145                 150                 155                 160

Gly Glu Thr Thr Pro Phe Ile Ser Ser Leu Glu Leu Arg Pro Leu Asn
                165                 170                 175

Gln Asn Thr Phe Val Thr Lys Ser Gly Ser Leu Val Val Val Ala Lys
            180                 185                 190

Leu Tyr Phe Ser Pro Thr Pro Pro Phe Leu Lys Tyr Asp Glu Asp Val
        195                 200                 205

Arg Asp Arg Ile Phe Ile Pro Phe Leu Asp Asn Lys Asn Ser Ala Leu
    210                 215                 220

Ser Ser Glu Leu Ser Val Asp Thr Cys Asn Phe Tyr Gln Val Pro Gln
225                 230                 235                 240

Thr Val Ala Lys Thr Ala Ile Val Pro Leu Asn Leu Thr Asn Pro Gly
                245                 250                 255

Lys Leu Gln Trp Ser Ile Asp Asp Ile Thr Ser Gln Cys Tyr Ile Tyr
            260                 265                 270

Met His Phe Ala Glu Met Glu Gln Leu Glu Ala Gln Glu Thr Arg Glu
        275                 280                 285

Phe Asn Ile Cys Tyr Asn Gly Gly Glu Gln Phe Phe Ser Tyr Phe Arg
    290                 295                 300

Pro Pro Lys Phe His Ile Thr Thr Leu Tyr Asn Pro Ala Ala Met Cys
305                 310                 315                 320

Ser Met Glu Gly Asn Phe Asn Phe Thr Trp Ser Met Thr Ala Asn Ser
                325                 330                 335

Thr Lys Pro Pro Leu Ile Asn Gly Leu Asp Ile Trp Gln Val Leu Asp
            340                 345                 350

Ile Pro Asn Leu Asp Thr Tyr Gln Asp Glu Val Ser Ala Leu Met Gln
```

-continued

```
        355                 360                 365

Ile Lys Thr Ile Trp Gly Leu Ser Arg Arg Ser Ser Phe Gln Gly Asp
    370                 375                 380

Pro Ser Leu Pro Asp Val Tyr Arg Trp Glu Val Leu Gln Cys Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560

Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
            580                 585                 590

Gln Val Ala Val Lys Met Leu Ser His Ser Ser Ala Gln Gly Tyr Lys
        595                 600                 605

Glu Trp Lys Gly Glu Val Glu Ala Leu Leu Arg Met His His Lys Lys
    610                 615                 620

Leu Ala Gly Leu Val Gly Phe Cys Asp Asp Gly Asp Asn Leu Ala Leu
625                 630                 635                 640

Ile Tyr Glu Trp Met Asp Lys Met Glu Met Arg Glu Asn Met Ser Gly
                645                 650                 655

Lys His Cys Val Asn Val Leu Ser Trp Glu Thr Arg Met Gln Ile Met
            660                 665                 670

Val Asp Ala Ala Gln Gly Leu Glu Tyr Leu Arg Asn Gly Cys Arg Pro
        675                 680                 685

Pro Met Val His Arg Asp Val Arg Pro Ser Asn Ile Leu Leu Asn Glu
    690                 695                 700

Arg Ser Gln Gly Lys Leu Leu Asp Tyr Gly Leu Ser Lys Ser Phe Pro
705                 710                 715                 720

Val Asp Gly Glu Thr His Val Met Thr Val Val Ala Gly Thr Pro Gly
                725                 730                 735

Tyr Leu Asp Pro Glu Tyr Tyr Arg Thr Asn Phe Leu Ser Glu Lys Cys
            740                 745                 750

Glu Val Tyr Ser Phe Met Val Val Val Leu Glu Ile Val Thr Asn Asn
        755                 760                 765

Pro Val Leu Gln Lys Gln Lys Asp Arg Pro His Ile Asn Glu Trp Leu
    770                 775                 780
```

```
Val Trp Met Leu Thr Asn Ala Asp Ile Lys Thr Ile Val Glu Pro Lys
785                 790                 795                 800

Leu Asn Glu Asp Tyr Asp Thr Asn Gly Val Trp Lys Val Val Glu Leu
                805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Ser Pro Leu Ala Arg
865                 870                 875


<210> SEQ ID NO 29
<211> LENGTH: 2628
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2628)
<223> OTHER INFORMATION: /organism="Artificial Sequence"
      /note="Nucleotide sequence RLK2, variant 21" /mol_type="unassigned
      DNA"

<400> SEQUENCE: 29

atgcacttcc tgagcttcct gatcttcatg ttcgccgtgg gcggcctggt gaacgcccag      60

gaccagagcg gcttcatcag cctggactgc atcctggtgc ccaccgagat caccttcgcc     120

gagaagagca ccaacatcac ctaccacagc gacgccacct tcatcgacac cggcgtgccc     180

gccaagatca acgaggtgta cagaacccag ttccagcagc agatgtgggc cctgagaagc     240

ttccccgagg gccagagaaa ctgctacaac ttcagcctga ccgccaagag aaagtggctg     300

atcagaggca ccttcatcta cggcaactac gacatcctga acaacctgcc cagcttcgag     360

ctgtacatca tcccccagaa gtggaccagc atgtgcatcc ccggcgtgag aaacggcagc     420

gtgagcgaca tgatccacgt gctgagacag gaccacctgc agatctgcct ggtgagaacc     480

ggcgagacct gccccttcat caccagcctg gagctgagac ccctgcagaa caacacctac     540

gtgaccaaga gcatgagcct gatcgtggtg gccagactgt ggttcacccc caccccccc     600

tggctgagat acgaggacga cgtgcacgac agaatcttca tccccttcgc cgagaacaag     660

aacagcgccc tgagcaccga gctgagcgtg gacacctgca acttctacca gatcccccag     720

accgtggcca agagcgccct ggtgcccctg aacgccaccc agcccgtgca catcaactgg     780

agcctggacg acatcaccag ccagagctac atctacatgc acttcgccga gatcgagaac     840

ctggaggcca acgacaccag agagttcaac atcacctaca acggcggcga ccagtggttc     900

agctacttca gacccccca cttcagaatc accagcgtgt acaaccccgc cgccgtgagc     960

agcctggagg gcaacttcaa ctggaccttc agcatgtgcg gcaacagcac ccacccccc    1020

ctgggcaacg gcgccgagat ctaccaggtg ctggagctgc cccagctgga cacctaccag    1080

gacgaggtga ccgccatgat gaacatcaag accatctaca tgctgagcaa gagaagcagc    1140

ttccagggcg accccaccgc ccccgacctg tacagatggg agggcctgaa ctgcagctac    1200

cccaacttcg ccccccccca gatcatcagc ctgaacctga gcggcagcaa cctgagcggc    1260

accatcacca gcgacatcag caagctgacc cacctgagag agctggacct gagcaacaac    1320
```

```
gacctgagcg gcgacatccc cttcgtgttc agcgacatga agaacctgac cctgatcaac   1380

ctgagcggca acaagaacct gaacagaagc gtgcccgaga ccctgcagaa gagaatcgac   1440

aacaagagcc tgaccctgat cagagacgag accggcaaga acagcaccaa cgtggtggcc   1500

atcgccgcca gcgtggccag cgtgttcgcc gtgctggtga tcctggccat cgtgttcgtg   1560

gtgatcagaa agaagcagag aaccaacgag gccagcggcc ccagaagctt caccaccggc   1620

accgtgaaga gcgacgccag aagcagcagc agcagcatca tcaccaagga gagaaagttc   1680

acctacagcg aggtgctgaa gatgaccaag aacttcgaga gagtgctggg caagggcggc   1740

ttcggcaccg tgtaccacgg caacctggac gacacccagg tggccgtgaa gatgctgagc   1800

cacagcagcg cccagggcta caaggagttc agagccgacg tggagctgct gatcagagtg   1860

caccacagac acatggtggg catcatggcc tactgcgacg acatggacaa cctggccctg   1920

atctacgagt acatggagaa gggcgacctg agagagaaca tgtgcgccca ccacagcgtg   1980

aacgtgctga gctgggagac cagaatgcag atcgccctgg aggccgccca gggcctggag   2040

tacctgcacc agggctgcag accccccatg gtgcacagag acgtgaagcc caccaacatc   2100

ctgctgaacg agagaagcca gctgaagctg gccgactaca tgctgagcag aagcttcccc   2160

gtggacggcg agagccacgt gatgaccgtg gtggccggca cccccatcta cctggacccc   2220

gagtactaca gaacccagta cctgagcgag aagagcgacg tgtacagctt cggcgtgatg   2280

ctgctggaca tcgtgaccaa ccagcccgtg atgaacaaga acagagagag accccacatc   2340

aacgactggg tggccttcat gctgaccaac ggcgagatcc acagcatcgt ggaccccaag   2400

ctgaacgagg actacgacac caacggcgtg tggaaggtgg tggagctggc cctggcctgc   2460

gtgaacccca gcagcagcag aagacccacc atgccccacg tggtgatgga gctgaacgag   2520

tgcctggccc tggagatcga gagaaagcag ggcagccagg ccacctacat caaggagagc   2580

gtggagttca gccccagcag cgccagcgac ttctgccccc tggccaga                2628
```

```
<210> SEQ ID NO 30
<211> LENGTH: 876
<212> TYPE: PRT
<213> ORGANISM: Artificial Sequence
<220> FEATURE:
<223> OTHER INFORMATION: Amino acid sequence RLK2, variant 21

<400> SEQUENCE: 30

Met His Phe Leu Ser Phe Leu Ile Phe Met Phe Ala Val Gly Gly Leu
1               5                   10                  15

Val Asn Ala Gln Asp Gln Ser Gly Phe Ile Ser Leu Asp Cys Ile Leu
            20                  25                  30

Val Pro Thr Glu Ile Thr Phe Ala Glu Lys Ser Thr Asn Ile Thr Tyr
        35                  40                  45

His Ser Asp Ala Thr Phe Ile Asp Thr Gly Val Pro Ala Lys Ile Asn
    50                  55                  60

Glu Val Tyr Arg Thr Gln Phe Gln Gln Gln Met Trp Ala Leu Arg Ser
65                  70                  75                  80

Phe Pro Glu Gly Gln Arg Asn Cys Tyr Asn Phe Ser Leu Thr Ala Lys
                85                  90                  95

Arg Lys Trp Leu Ile Arg Gly Thr Phe Ile Tyr Gly Asn Tyr Asp Ile
            100                 105                 110

Leu Asn Asn Leu Pro Ser Phe Glu Leu Tyr Ile Ile Pro Gln Lys Trp
        115                 120                 125

Thr Ser Met Cys Ile Pro Gly Val Arg Asn Gly Ser Val Ser Asp Met
```

```
    130                 135                 140

Ile His Val Leu Arg Gln Asp His Leu Gln Ile Cys Leu Val Arg Thr
145                 150                 155                 160

Gly Glu Thr Cys Pro Phe Ile Thr Ser Leu Glu Leu Arg Pro Leu Gln
                165                 170                 175

Asn Asn Thr Tyr Val Thr Lys Ser Met Ser Leu Ile Val Val Ala Arg
            180                 185                 190

Leu Trp Phe Thr Pro Thr Pro Pro Trp Leu Arg Tyr Glu Asp Asp Val
        195                 200                 205

His Asp Arg Ile Phe Ile Pro Phe Ala Glu Asn Lys Asn Ser Ala Leu
    210                 215                 220

Ser Thr Glu Leu Ser Val Asp Thr Cys Asn Phe Tyr Gln Ile Pro Gln
225                 230                 235                 240

Thr Val Ala Lys Ser Ala Leu Val Pro Leu Asn Ala Thr Gln Pro Val
                245                 250                 255

His Ile Asn Trp Ser Leu Asp Asp Ile Thr Ser Gln Ser Tyr Ile Tyr
            260                 265                 270

Met His Phe Ala Glu Ile Glu Asn Leu Glu Ala Asn Asp Thr Arg Glu
        275                 280                 285

Phe Asn Ile Thr Tyr Asn Gly Gly Asp Gln Trp Phe Ser Tyr Phe Arg
    290                 295                 300

Pro Pro His Phe Arg Ile Thr Ser Val Tyr Asn Pro Ala Ala Val Ser
305                 310                 315                 320

Ser Leu Glu Gly Asn Phe Asn Trp Thr Phe Ser Met Cys Gly Asn Ser
                325                 330                 335

Thr His Pro Pro Leu Gly Asn Gly Ala Glu Ile Tyr Gln Val Leu Glu
            340                 345                 350

Leu Pro Gln Leu Asp Thr Tyr Gln Asp Glu Val Thr Ala Met Met Asn
        355                 360                 365

Ile Lys Thr Ile Tyr Met Leu Ser Lys Arg Ser Ser Phe Gln Gly Asp
    370                 375                 380

Pro Thr Ala Pro Asp Leu Tyr Arg Trp Glu Gly Leu Asn Cys Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560
```

```
Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
            580                 585                 590

Gln Val Ala Val Lys Met Leu Ser His Ser Ser Ala Gln Gly Tyr Lys
        595                 600                 605

Glu Phe Arg Ala Asp Val Glu Leu Leu Ile Arg Val His His Arg His
    610                 615                 620

Met Val Gly Ile Met Ala Tyr Cys Asp Asp Met Asp Asn Leu Ala Leu
625                 630                 635                 640

Ile Tyr Glu Tyr Met Glu Lys Gly Asp Leu Arg Glu Asn Met Cys Ala
                645                 650                 655

His His Ser Val Asn Val Leu Ser Trp Glu Thr Arg Met Gln Ile Ala
            660                 665                 670

Leu Glu Ala Ala Gln Gly Leu Glu Tyr Leu His Gln Gly Cys Arg Pro
        675                 680                 685

Pro Met Val His Arg Asp Val Lys Pro Thr Asn Ile Leu Leu Asn Glu
    690                 695                 700

Arg Ser Gln Leu Lys Leu Ala Asp Tyr Met Leu Ser Arg Ser Phe Pro
705                 710                 715                 720

Val Asp Gly Glu Ser His Val Met Thr Val Val Ala Gly Thr Pro Ile
                725                 730                 735

Tyr Leu Asp Pro Glu Tyr Tyr Arg Thr Gln Tyr Leu Ser Glu Lys Ser
            740                 745                 750

Asp Val Tyr Ser Phe Gly Val Met Leu Leu Asp Ile Val Thr Asn Gln
        755                 760                 765

Pro Val Met Asn Lys Asn Arg Glu Arg Pro His Ile Asn Asp Trp Val
    770                 775                 780

Ala Phe Met Leu Thr Asn Gly Glu Ile His Ser Ile Val Asp Pro Lys
785                 790                 795                 800

Leu Asn Glu Asp Tyr Asp Thr Asn Gly Val Trp Lys Val Val Glu Leu
                805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Cys Pro Leu Ala Arg
865                 870                 875


<210> SEQ ID NO 31
<211> LENGTH: 2628
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2628)
<223> OTHER INFORMATION: /organism="Artificial Sequence"
      /note="Nucleotide sequence RLK2, variant 22" /mol_type="unassigned
      DNA"

<400> SEQUENCE: 31

atgagattcc tgagcttcct gatctacgtg ttcgccgtgc tgggcctggt gaacgcccag     60
```

-continued

```
gaccagagcg gctacatcag cctggactgc ggcctggtgc ccaccgaggt gacctacgtg    120
gagaagagca cccagatcac ctacagaagc gacgccacct acgtggacag cggcggcccc    180
ggcaagatca acgaggtgta cagaagccag ttccagcagc agatctgggc cgtgagaagc    240
ttccccgagg gccagagaaa ctgctacaac ttcagcctga ccgccaagag acactacctg    300
atcagaggca ccttcatcta cggcaactac gacatcctgc agcagctgcc cagcttcgac    360
ctgtacatcg gccccaacaa gtggaccacc gtgagcatcc ccggcgtgag aaacggcacc    420
gtgagcgaga tgatccacgt gctgagaaac gaccacctgc agatctgcct ggcccacagc    480
ggcgagacct gccccttcat cagcagcctg gagctgagac ccctgaacaa caacacctac    540
gtgaccaaga gcggcagcct gatcgtgctg gccagactgt actggacccc caccccccc     600
tgggtgagat acgacgagga cgtgcacgac agaatctgga tcccctggct ggacaacaag    660
aacagcctgg tgagcaccga gctgagcgtg gacaccacca acttctacaa cgtgccccag    720
accgtggcca agaccgccgc cgtgcccctg aacgccaccc agcccctgaa gatcaactgg    780
accctggagg acatcaccac ccagagctac atctacatgc acttcgccga ggtggagaac    840
ctggacgcca acgacaccag agagttcaac atcacctaca acgccggcga gaactggtac    900
agctacttca gacccccaa gttcagaatc accaccgtgt acaaccccgc cctggtgacc    960
agcctggacg gcaacttcaa cttcaccttc agcggcaccg gcaactgctg caagcccccc   1020
ctgggcaacg gcctggagat ctaccaggtg ctggagctgc cccagctgga cacctacaac   1080
gacgaggtga gcgccgccat gaacatcaga accgtgtacg gcctgagcag acacagcagc   1140
tggcagggcg acccctgcat ccccgacctg ttcagattcg agggcctgaa ctgcagctac   1200
cccaacttcg ccccccccca gatcatcagc ctgaacctga gcggcagcaa cctgagcggc   1260
accatcacca gcgacatcag caagctgacc cacctgagag agctggacct gagcaacaac   1320
gacctgagcg gcgacatccc cttcgtgttc agcgacatga agaacctgac cctgatcaac   1380
ctgagcggca acaagaacct gaacagaagc gtgcccgaga ccctgcagaa gagaatcgac   1440
aacaagagcc tgaccctgat cagagacgag accggcaaga acagcaccaa cgtggtggcc   1500
atcgccgcca gcgtggccag cgtgttcgcc gtgctggtga tcctggccat cgtgttcgtg   1560
gtgatcagaa agaagcagag aaccaacgag gccagcggcc ccagaagctt caccaccggc   1620
accgtgaaga gcgacgccag aagcagcagc agcagcatca tcaccaagga gagaaagttc   1680
acctacagcg aggtgctgaa gatgaccaag aacttcgaga gagtgctggg caagggcggc   1740
ttcggcaccg tgtaccacgg caacctggac gacacccagg tggccgtgaa gatgctgagc   1800
cacacctgcg tgcagggcta caaggagttc aaggccgagg tggagctgct gctgagagtg   1860
cacagaagac acctggtggg cctggtgggc tactgcgacg agggcgacaa cctggccctg   1920
atctacgagt acatggagaa gggcgagctg agagagcaga tgagcggcaa gcacagcgtg   1980
aacgtgctga gctgggagac cagaatgcag atcgccgtgg acgccgccca gggcctggag   2040
tacctgcaca acggctgcag acccccatg gtgcacagag acgtgaagcc caccaacatc    2100
ctgctgaacg agagatgcca ggccaagctg gccgacttcg gcctgagcag aagcttcccc   2160
gtggacatgg agagccacgt gatgtgcgtg gtggccggca cccccggcta cctggacccc   2220
gagtactaca gaaccaactg gctgagcgag aagagcgacg tgtacagctt cggcgtggtg   2280
ctgctggaga tcgtgaccaa ccagcccgtg atgaacaaga acagagagag accccacatc   2340
aacgagtacg tgatgttcat gctgtgcaac ggcgacatca agagcatcgt ggagcccaag   2400
ctgaacgagg actacgacac caacggcgtg tggaaggtgg tggagctggc cctggcctgc   2460
```

```
gtgaacccca gcagcagcag aagacccacc atgccccacg tggtgatgga gctgaacgag   2520

tgcctggccc tggagatcga gagaaagcag ggcagccagg ccacctacat caaggagagc   2580

gtggagttca gccccagcag cgccagcgac ttcagccccc tggccaga                2628


<210> SEQ ID NO 32
<211> LENGTH: 876
<212> TYPE: PRT
<213> ORGANISM: Artificial Sequence
<220> FEATURE:
<223> OTHER INFORMATION: Amino acid sequence RLK2, variant 22

<400> SEQUENCE: 32

Met Arg Phe Leu Ser Phe Leu Ile Tyr Val Phe Ala Val Leu Gly Leu
1               5                   10                  15

Val Asn Ala Gln Asp Gln Ser Gly Tyr Ile Ser Leu Asp Cys Gly Leu
            20                  25                  30

Val Pro Thr Glu Val Thr Tyr Val Glu Lys Ser Thr Gln Ile Thr Tyr
        35                  40                  45

Arg Ser Asp Ala Thr Tyr Val Asp Ser Gly Gly Pro Gly Lys Ile Asn
    50                  55                  60

Glu Val Tyr Arg Ser Gln Phe Gln Gln Gln Ile Trp Ala Val Arg Ser
65                  70                  75                  80

Phe Pro Glu Gly Gln Arg Asn Cys Tyr Asn Phe Ser Leu Thr Ala Lys
                85                  90                  95

Arg His Tyr Leu Ile Arg Gly Thr Phe Ile Tyr Gly Asn Tyr Asp Ile
            100                 105                 110

Leu Gln Gln Leu Pro Ser Phe Asp Leu Tyr Ile Gly Pro Asn Lys Trp
        115                 120                 125

Thr Thr Val Ser Ile Pro Gly Val Arg Asn Gly Thr Val Ser Glu Met
    130                 135                 140

Ile His Val Leu Arg Asn Asp His Leu Gln Ile Cys Leu Ala His Ser
145                 150                 155                 160

Gly Glu Thr Cys Pro Phe Ile Ser Ser Leu Glu Leu Arg Pro Leu Asn
                165                 170                 175

Asn Asn Thr Tyr Val Thr Lys Ser Gly Ser Leu Ile Val Leu Ala Arg
            180                 185                 190

Leu Tyr Trp Thr Pro Thr Pro Pro Trp Val Arg Tyr Asp Glu Asp Val
        195                 200                 205

His Asp Arg Ile Trp Ile Pro Trp Leu Asp Asn Lys Asn Ser Leu Val
    210                 215                 220

Ser Thr Glu Leu Ser Val Asp Thr Thr Asn Phe Tyr Asn Val Pro Gln
225                 230                 235                 240

Thr Val Ala Lys Thr Ala Ala Val Pro Leu Asn Ala Thr Gln Pro Leu
                245                 250                 255

Lys Ile Asn Trp Thr Leu Glu Asp Ile Thr Thr Gln Ser Tyr Ile Tyr
            260                 265                 270

Met His Phe Ala Glu Val Glu Asn Leu Asp Ala Asn Asp Thr Arg Glu
        275                 280                 285

Phe Asn Ile Thr Tyr Asn Ala Gly Glu Asn Trp Tyr Ser Tyr Phe Arg
    290                 295                 300

Pro Pro Lys Phe Arg Ile Thr Thr Val Tyr Asn Pro Ala Leu Val Thr
305                 310                 315                 320

Ser Leu Asp Gly Asn Phe Asn Phe Thr Phe Ser Gly Thr Gly Asn Cys
                325                 330                 335
```

-continued

```
Cys Lys Pro Pro Leu Gly Asn Gly Leu Glu Ile Tyr Gln Val Leu Glu
            340                 345                 350

Leu Pro Gln Leu Asp Thr Tyr Asn Asp Glu Val Ser Ala Ala Met Asn
        355                 360                 365

Ile Arg Thr Val Tyr Gly Leu Ser Arg His Ser Ser Trp Gln Gly Asp
    370                 375                 380

Pro Cys Ile Pro Asp Leu Phe Arg Phe Glu Gly Leu Asn Cys Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560

Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
            580                 585                 590

Gln Val Ala Val Lys Met Leu Ser His Thr Cys Val Gln Gly Tyr Lys
        595                 600                 605

Glu Phe Lys Ala Glu Val Glu Leu Leu Leu Arg Val His Arg Arg His
    610                 615                 620

Leu Val Gly Leu Val Gly Tyr Cys Asp Glu Gly Asp Asn Leu Ala Leu
625                 630                 635                 640

Ile Tyr Glu Tyr Met Glu Lys Gly Glu Leu Arg Glu Gln Met Ser Gly
                645                 650                 655

Lys His Ser Val Asn Val Leu Ser Trp Glu Thr Arg Met Gln Ile Ala
            660                 665                 670

Val Asp Ala Ala Gln Gly Leu Glu Tyr Leu His Asn Gly Cys Arg Pro
        675                 680                 685

Pro Met Val His Arg Asp Val Lys Pro Thr Asn Ile Leu Leu Asn Glu
    690                 695                 700

Arg Cys Gln Ala Lys Leu Ala Asp Phe Gly Leu Ser Arg Ser Phe Pro
705                 710                 715                 720

Val Asp Met Glu Ser His Val Met Cys Val Val Ala Gly Thr Pro Gly
                725                 730                 735

Tyr Leu Asp Pro Glu Tyr Tyr Arg Thr Asn Trp Leu Ser Glu Lys Ser
            740                 745                 750
```

-continued

```
Asp Val Tyr Ser Phe Gly Val Val Leu Leu Glu Ile Val Thr Asn Gln
        755                 760                 765

Pro Val Met Asn Lys Asn Arg Glu Arg Pro His Ile Asn Glu Tyr Val
    770                 775                 780

Met Phe Met Leu Cys Asn Gly Asp Ile Lys Ser Ile Val Glu Pro Lys
785                 790                 795                 800

Leu Asn Glu Asp Tyr Asp Thr Asn Gly Val Trp Lys Val Val Glu Leu
                805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Ser Pro Leu Ala Arg
865                 870                 875
```

<210> SEQ ID NO 33
<211> LENGTH: 2628
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2628)
<223> OTHER INFORMATION: /organism="Artificial Sequence"
/note="Nucleotide sequence RLK2, variant 23" /mol_type="unassigned
DNA"

<400> SEQUENCE: 33

```
atgagattcc tgagcttcct gatctacgtg ttcgccgtgc tgggcctggt gaacgcccag     60

gaccagagcg gcttcatcag cctggactgc ggcctgctgc cctgcgagat ctgctacgtg    120

gagaagagca ccaacatcac ctacagaagc gacgccacct acatcgacag cggcgtgccc    180

ggcaaggtga acgagatcta cagaacccag ttccagcagc agatctggat cctgagaagc    240

ttccccgagg gccagagaaa ctgctacaac ttcagcctga ccgccaagag aaagtacctg    300

atcagaggca ccttcatcta cggcaactac gacggcctga accagctgcc cagcttcgac    360

ctgtacatgg gccccaacaa gtggaccagc gtgagcatcc ccggcgtgag aaacggctgc    420

gtgagcgagg ccatccacgt gctgagacag gaccacctgc agatctgcct ggtgaagacc    480

ggcgagacca ccccccttcat cagcagcctg gagctgagac ccctgaacaa caacacctac    540

gtgaccaaga gcctgagcct gatcgtggtg gccagactgt acttcagccc cacccccccc    600

ttcctgagat acgacgagga cgtgcacgac agaatctgga tccccttcct ggacaaccac    660

aacagcctgc tgagcaccga gctgagcgtg gacaccagca acttctacaa cgtgccccag    720

accgtggcca agaccgccgt ggtgcccctg aacgccaccc agcccctgag aatcaactgg    780

agcctggacg acatcagcag ccagagctgg atctacatgc acttcggcga gatcgagaac    840

ctggaggcca acgagaccag agagttcaac atcagctaca acggcggcga gcagtggttc    900

agctacttca gacccccccaa gttcagaatc agcaccgtgt acaaccccgc cgccgtgagc    960

agcctggacg gcaacttcaa cttcaccttc agcatgaccg gcaacagcac ccaccccccc   1020

ctgatcaacg gcctggagat ctaccaggcc ctggagctgc cccagctgga cacctaccag   1080

gaggaggtga gcgccatgat gaacatcaag accatctacg gcctgagcaa gagaagcagc   1140

tggcagggcg agcccagcgc ccccgagctg tacagatggg agatcctgaa ctgcagctac   1200
```

```
cccaacttcg ccccccccca gatcatcagc ctgaacctga gcggcagcaa cctgagcggc   1260
accatcacca gcgacatcag caagctgacc cacctgagag agctggacct gagcaacaac   1320
gacctgagcg gcgacatccc cttcgtgttc agcgacatga agaacctgac cctgatcaac   1380
ctgagcggca acaagaacct gaacagaagc gtgcccgaga ccctgcagaa gagaatcgac   1440
aacaagagcc tgaccctgat cagagacgag accggcaaga acagcaccaa cgtggtggcc   1500
atcgccgcca gcgtggccag cgtgttcgcc gtgctggtga tcctggccat cgtgttcgtg   1560
gtgatcagaa agaagcagag aaccaacgag gccagcggcc ccagaagctt caccaccggc   1620
accgtgaaga gcgacgccag aagcagcagc agcagcatca tcaccaagga gagaaagttc   1680
acctacagcg aggtgctgaa gatgaccaag aacttcgaga gagtgctggg caagggcggc   1740
ttcggcaccg tgtaccacgg caacctggac gacacccagg tggccgtgaa gatgctgagc   1800
cacagcagcg cccagggcta caaggagtgg aaggccgagg tggagctgct gctgagagtg   1860
cacaagagac acatcgtggg cctggtgggc tactgcgacg acggcgacaa cctggccctg   1920
atctacgagt acatggagaa gggcgacctg agagagaaca tgagcggcaa gcacagcgtg   1980
caggccctga cctgggagac cagaatgcag atcctggtgg aggccgccca gggcctggag   2040
tacgtgcacc agggctgcag accccccatg gtgcacagag acgtgaagcc caccaacatc   2100
ctgctgaacg agagaagcca ggccaagctg gccgacttcg gcctgagcag aagcttcccc   2160
gtggacggcg acagccacgt gatgaccgtg gtggtgggca cccccggcta cctggacccc   2220
gagtactaca gaaccaactg gctgagcgag aagaccgacg tgtacagctt cggcgtggtg   2280
ctgctggaga tcgtgaccaa ccagcccgtg atgaacaaga acagagagag accccacatc   2340
aacgagtggg ccatgttcat gctgaccaac gtggacatca agagcatcgt ggagcccaag   2400
ctgaacgagg actacgacac caacggcgtg tggaaggtgg tggagctggc cctggcctgc   2460
gtgaacccca gcagcagcag aagacccacc atgccccacg tggtgatgga gctgaacgag   2520
tgcctggccc tggagatcga gagaaagcag ggcagccagg ccacctacat caaggagagc   2580
gtggagttca gccccagcag cgccagcgac ttcagccccc tggccaga                 2628
```

<210> SEQ ID NO 34
<211> LENGTH: 876
<212> TYPE: PRT
<213> ORGANISM: Artificial Sequence
<220> FEATURE:
<223> OTHER INFORMATION: Amino acid sequence RLK2, variant 23

<400> SEQUENCE: 34

```
Met Arg Phe Leu Ser Phe Leu Ile Tyr Val Phe Ala Val Leu Gly Leu
1               5                   10                  15

Val Asn Ala Gln Asp Gln Ser Gly Phe Ile Ser Leu Asp Cys Gly Leu
            20                  25                  30

Leu Pro Cys Glu Ile Cys Tyr Val Glu Lys Ser Thr Asn Ile Thr Tyr
        35                  40                  45

Arg Ser Asp Ala Thr Tyr Ile Asp Ser Gly Val Pro Gly Lys Val Asn
    50                  55                  60

Glu Ile Tyr Arg Thr Gln Phe Gln Gln Gln Ile Trp Ile Leu Arg Ser
65                  70                  75                  80

Phe Pro Glu Gly Gln Arg Asn Cys Tyr Asn Phe Ser Leu Thr Ala Lys
                85                  90                  95

Arg Lys Tyr Leu Ile Arg Gly Thr Phe Ile Tyr Gly Asn Tyr Asp Gly
            100                 105                 110
```

-continued

```
Leu Asn Gln Leu Pro Ser Phe Asp Leu Tyr Met Gly Pro Asn Lys Trp
        115                 120                 125

Thr Ser Val Ser Ile Pro Gly Val Arg Asn Gly Cys Val Ser Glu Ala
    130                 135                 140

Ile His Val Leu Arg Gln Asp His Leu Gln Ile Cys Leu Val Lys Thr
145                 150                 155                 160

Gly Glu Thr Thr Pro Phe Ile Ser Ser Leu Glu Leu Arg Pro Leu Asn
                165                 170                 175

Asn Asn Thr Tyr Val Thr Lys Ser Leu Ser Leu Ile Val Val Ala Arg
            180                 185                 190

Leu Tyr Phe Ser Pro Thr Pro Pro Phe Leu Arg Tyr Asp Glu Asp Val
        195                 200                 205

His Asp Arg Ile Trp Ile Pro Phe Leu Asp Asn His Asn Ser Leu Leu
    210                 215                 220

Ser Thr Glu Leu Ser Val Asp Thr Ser Asn Phe Tyr Asn Val Pro Gln
225                 230                 235                 240

Thr Val Ala Lys Thr Ala Val Val Pro Leu Asn Ala Thr Gln Pro Leu
                245                 250                 255

Arg Ile Asn Trp Ser Leu Asp Asp Ile Ser Ser Gln Ser Trp Ile Tyr
            260                 265                 270

Met His Phe Gly Glu Ile Glu Asn Leu Glu Ala Asn Glu Thr Arg Glu
        275                 280                 285

Phe Asn Ile Ser Tyr Asn Gly Gly Glu Gln Trp Phe Ser Tyr Phe Arg
    290                 295                 300

Pro Pro Lys Phe Arg Ile Ser Thr Val Tyr Asn Pro Ala Ala Val Ser
305                 310                 315                 320

Ser Leu Asp Gly Asn Phe Asn Phe Thr Phe Ser Met Thr Gly Asn Ser
                325                 330                 335

Thr His Pro Pro Leu Ile Asn Gly Leu Glu Ile Tyr Gln Ala Leu Glu
            340                 345                 350

Leu Pro Gln Leu Asp Thr Tyr Gln Glu Glu Val Ser Ala Met Met Asn
        355                 360                 365

Ile Lys Thr Ile Tyr Gly Leu Ser Lys Arg Ser Ser Trp Gln Gly Glu
    370                 375                 380

Pro Ser Ala Pro Glu Leu Tyr Arg Trp Glu Ile Leu Asn Cys Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525
```

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560

Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
            580                 585                 590

Gln Val Ala Val Lys Met Leu Ser His Ser Ser Ala Gln Gly Tyr Lys
        595                 600                 605

Glu Trp Lys Ala Glu Val Glu Leu Leu Leu Arg Val His Lys Arg His
    610                 615                 620

Ile Val Gly Leu Val Gly Tyr Cys Asp Asp Gly Asp Asn Leu Ala Leu
625                 630                 635                 640

Ile Tyr Glu Tyr Met Glu Lys Gly Asp Leu Arg Glu Asn Met Ser Gly
                645                 650                 655

Lys His Ser Val Gln Ala Leu Thr Trp Glu Thr Arg Met Gln Ile Leu
            660                 665                 670

Val Glu Ala Ala Gln Gly Leu Glu Tyr Val His Gln Gly Cys Arg Pro
        675                 680                 685

Pro Met Val His Arg Asp Val Lys Pro Thr Asn Ile Leu Leu Asn Glu
    690                 695                 700

Arg Ser Gln Ala Lys Leu Ala Asp Phe Gly Leu Ser Arg Ser Phe Pro
705                 710                 715                 720

Val Asp Gly Asp Ser His Val Met Thr Val Val Val Gly Thr Pro Gly
                725                 730                 735

Tyr Leu Asp Pro Glu Tyr Tyr Arg Thr Asn Trp Leu Ser Glu Lys Thr
            740                 745                 750

Asp Val Tyr Ser Phe Gly Val Val Leu Leu Glu Ile Val Thr Asn Gln
        755                 760                 765

Pro Val Met Asn Lys Asn Arg Glu Arg Pro His Ile Asn Glu Trp Ala
    770                 775                 780

Met Phe Met Leu Thr Asn Val Asp Ile Lys Ser Ile Val Glu Pro Lys
785                 790                 795                 800

Leu Asn Glu Asp Tyr Asp Thr Asn Gly Val Trp Lys Val Val Glu Leu
                805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Ser Pro Leu Ala Arg
865                 870                 875

<210> SEQ ID NO 35
<211> LENGTH: 2628
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: source
<222> LOCATION: (1)..(2628)
<223> OTHER INFORMATION: /organism="Artificial Sequence"
/note="Nucleotide sequence RLK2, variant 24" /mol_type="unassigned
DNA"

<400> SEQUENCE: 35
atgagatacc tgagcttcct gatctacgtg ttcgccgtgc tgggcctggt gcaggcccag 60
gaccagagcg gcttcatcag cctggactgc ggcctgggcc ccaccgagat cacctacgtg 120
gagaagagca ccaacatcac ctacagaagc gacgccacct acatcgacag catggtgccc 180
ggcaagatca acgaggtgta cagaacccag ttccagcagc agatctgggc cctgagaagc 240
ttccccgagg gcaacagaaa ctgctacaac tggagcatga ccgccaagag aaagtacctg 300
atcagaggca ccttcatcta cggcaactac gacggcctga accagctgcc cagcttcgac 360
ctgtacatcg gccccaacaa gtggaccagc gtgagcatcc ccgccgtgag aaacggcagc 420
gtgagcgaga tgatccacgt gggcagacag gaccacctgc agatctgcct ggtgaagacc 480
ggcgagacca ccccccttcat cagcagcctg gagctgagac ccctgaacaa caacacctac 540
gtgaccaaga gcggcagcct gatcgtggtg gccagactgt acttcagccc cacccccccc 600
ttcctgagat acgacgagga cgtgcacgac agaatctgga tccccttcct ggacaacaag 660
aacaccctgc tgagcaccga gctgagcgtg gacaccacca acttctacaa cgtgccccag 720
accgtggcca agaccgccgc cgtgcccctg aacgccaccc agcccctgaa gatcaacttc 780
agcctggacg acatcaccag ccagagctac atctggatgc acttcctgga gatcgagaac 840
ctggaggcca acgagaccag agagttcaac atcacctacc agggcggcga gaactggttc 900
agctacttca gacccccccaa gttcagaatc accaccgtgt acaaccccgc cgccgtgagc 960
agcctggacg gcaacttcaa cttcaccttc agcatgaccg gcaacagcac ccaccccccc 1020
ctgatcaacg gcctggagat ctaccaggtg ctggagctgc cccagctgga cacctaccag 1080
gacgaggtga gcgccatgat gaacatcaag accatctacg gcctgagcaa gagaagctgc 1140
tggcagggcg accccctgcgc ccccgagctg tacagatggg agggcctgaa ctgcagctac 1200
cccaacttcg cccccccccca gatcatcagc ctgaacctga gcggcagcaa cctgagcggc 1260
accatcacca gcgacatcag caagctgacc cacctgagag agctggacct gagcaacaac 1320
gacctgagcg gcgacatccc cttcgtgttc agcgacatga agaacctgac cctgatcaac 1380
ctgagcggca acaagaacct gaacagaagc gtgcccgaga ccctgcagaa gagaatcgac 1440
aacaagagcc tgaccctgat cagagacgag accggcaaga acagcaccaa cgtggtggcc 1500
atcgccgcca gcgtggccag cgtgttcgcc gtgctggtga tcctggccat cgtgttcgtg 1560
gtgatcagaa agaagcagag aaccaacgag gccagcggcc ccagaagctt caccaccggc 1620
accgtgaaga gcgacgccag aagcagcagc agcagcatca tcaccaagga gagaaagttc 1680
acctacagcg aggtgctgaa gatgaccaag aacttcgaga gagtgctggg caagggcggc 1740
ttcggcaccg tgtaccacgg caacctggac gacacccagg tggccgtgaa gatgctgagc 1800
cacagcagcg cccagggcta caaggacttc aaggccgagg tggagctgct gctgagagtg 1860
caccacagac acctggtggg cggcgtgggc tactgcgacg acggcgacaa cctggccctg 1920
atctacgagt acatggagaa gggcgacctg agagagaaca tgagcggcaa gcacagcgtg 1980
aacgtgctga gctgggagac cagaatgcag atcgccgccg aggccgccca gggcctggag 2040
tacctgcaca acggctgcag accccccatg gtgcacagag acgtgaagcc cagcaacgcc 2100
ctgggcaacg agagaagcca ggccaagctg gccgacttcg gcctgagcag aagcttcccc 2160
gtggacggcg agagccacgt gatgaccgtg gtggccggca cccccggcta cctggacccc 2220
gagtactaca gaaccaactg ggtgagcgag aagagcgacg tgtacagctt cggcgtggtg 2280
ctgctggaga tcgtgaccaa ccagcccggc atgaacaaga acagagagag accccacatc 2340
aacgagtggg tgatgttcat gctgaccaac ggcgacatca agagcatcgt ggaccccaag 2400
ctgaacgagg actacgacac caacggcgtg tggaaggtgg tggagctggc cctggcctgc 2460
gtgaacccca gcagcagcag aagacccacc atgccccacg tggtgatgga gctgaacgag 2520
tgcctggccc tggagatcga gagaaagcag ggcagccagg ccacctacat caaggagagc 2580
gtggagttca gccccagcag cgccagcgac ttcagccccc tggccaga 2628

<210> SEQ ID NO 36
<211> LENGTH: 876
<212> TYPE: PRT
<213> ORGANISM: Artificial Sequence
<220> FEATURE:
<223> OTHER INFORMATION: Amino acid sequence RLK2, variant 24

<400> SEQUENCE: 36

Met Arg Tyr Leu Ser Phe Leu Ile Tyr Val Phe Ala Val Leu Gly Leu
1 5 10 15

Val Gln Ala Gln Asp Gln Ser Gly Phe Ile Ser Leu Asp Cys Gly Leu
20 25 30

Gly Pro Thr Glu Ile Thr Tyr Val Glu Lys Ser Thr Asn Ile Thr Tyr
35 40 45

Arg Ser Asp Ala Thr Tyr Ile Asp Ser Met Val Pro Gly Lys Ile Asn
50 55 60

Glu Val Tyr Arg Thr Gln Phe Gln Gln Gln Ile Trp Ala Leu Arg Ser
65 70 75 80

Phe Pro Glu Gly Asn Arg Asn Cys Tyr Asn Trp Ser Met Thr Ala Lys
85 90 95

Arg Lys Tyr Leu Ile Arg Gly Thr Phe Ile Tyr Gly Asn Tyr Asp Gly
100 105 110

Leu Asn Gln Leu Pro Ser Phe Asp Leu Tyr Ile Gly Pro Asn Lys Trp
115 120 125

Thr Ser Val Ser Ile Pro Ala Val Arg Asn Gly Ser Val Ser Glu Met
130 135 140

Ile His Val Gly Arg Gln Asp His Leu Gln Ile Cys Leu Val Lys Thr
145 150 155 160

Gly Glu Thr Thr Pro Phe Ile Ser Ser Leu Glu Leu Arg Pro Leu Asn
165 170 175

Asn Asn Thr Tyr Val Thr Lys Ser Gly Ser Leu Ile Val Val Ala Arg
180 185 190

Leu Tyr Phe Ser Pro Thr Pro Pro Phe Leu Arg Tyr Asp Glu Asp Val
195 200 205

His Asp Arg Ile Trp Ile Pro Phe Leu Asp Asn Lys Asn Thr Leu Leu
210 215 220

Ser Thr Glu Leu Ser Val Asp Thr Thr Asn Phe Tyr Asn Val Pro Gln
225 230 235 240

Thr Val Ala Lys Thr Ala Ala Val Pro Leu Asn Ala Thr Gln Pro Leu
245 250 255

Lys Ile Asn Phe Ser Leu Asp Asp Ile Thr Ser Gln Ser Tyr Ile Trp
260 265 270

Met His Phe Leu Glu Ile Glu Asn Leu Glu Ala Asn Glu Thr Arg Glu
275 280 285

Phe Asn Ile Thr Tyr Gln Gly Gly Glu Asn Trp Phe Ser Tyr Phe Arg
290 295 300

-continued

```
Pro Pro Lys Phe Arg Ile Thr Thr Val Tyr Asn Pro Ala Ala Val Ser
305                 310                 315                 320

Ser Leu Asp Gly Asn Phe Asn Phe Thr Phe Ser Met Thr Gly Asn Ser
                325                 330                 335

Thr His Pro Pro Leu Ile Asn Gly Leu Glu Ile Tyr Gln Val Leu Glu
            340                 345                 350

Leu Pro Gln Leu Asp Thr Tyr Gln Asp Glu Val Ser Ala Met Met Asn
        355                 360                 365

Ile Lys Thr Ile Tyr Gly Leu Ser Lys Arg Ser Cys Trp Gln Gly Asp
    370                 375                 380

Pro Cys Ala Pro Glu Leu Tyr Arg Trp Glu Gly Leu Asn Cys Ser Tyr
385                 390                 395                 400

Pro Asn Phe Ala Pro Pro Gln Ile Ile Ser Leu Asn Leu Ser Gly Ser
                405                 410                 415

Asn Leu Ser Gly Thr Ile Thr Ser Asp Ile Ser Lys Leu Thr His Leu
            420                 425                 430

Arg Glu Leu Asp Leu Ser Asn Asn Asp Leu Ser Gly Asp Ile Pro Phe
        435                 440                 445

Val Phe Ser Asp Met Lys Asn Leu Thr Leu Ile Asn Leu Ser Gly Asn
    450                 455                 460

Lys Asn Leu Asn Arg Ser Val Pro Glu Thr Leu Gln Lys Arg Ile Asp
465                 470                 475                 480

Asn Lys Ser Leu Thr Leu Ile Arg Asp Glu Thr Gly Lys Asn Ser Thr
                485                 490                 495

Asn Val Val Ala Ile Ala Ala Ser Val Ala Ser Val Phe Ala Val Leu
            500                 505                 510

Val Ile Leu Ala Ile Val Phe Val Val Ile Arg Lys Lys Gln Arg Thr
        515                 520                 525

Asn Glu Ala Ser Gly Pro Arg Ser Phe Thr Thr Gly Thr Val Lys Ser
    530                 535                 540

Asp Ala Arg Ser Ser Ser Ser Ser Ile Ile Thr Lys Glu Arg Lys Phe
545                 550                 555                 560

Thr Tyr Ser Glu Val Leu Lys Met Thr Lys Asn Phe Glu Arg Val Leu
                565                 570                 575

Gly Lys Gly Gly Phe Gly Thr Val Tyr His Gly Asn Leu Asp Asp Thr
            580                 585                 590

Gln Val Ala Val Lys Met Leu Ser His Ser Ser Ala Gln Gly Tyr Lys
        595                 600                 605

Asp Phe Lys Ala Glu Val Glu Leu Leu Leu Arg Val His His Arg His
    610                 615                 620

Leu Val Gly Gly Val Gly Tyr Cys Asp Asp Gly Asp Asn Leu Ala Leu
625                 630                 635                 640

Ile Tyr Glu Tyr Met Glu Lys Gly Asp Leu Arg Glu Asn Met Ser Gly
                645                 650                 655

Lys His Ser Val Asn Val Leu Ser Trp Glu Thr Arg Met Gln Ile Ala
            660                 665                 670

Ala Glu Ala Ala Gln Gly Leu Glu Tyr Leu His Asn Gly Cys Arg Pro
        675                 680                 685

Pro Met Val His Arg Asp Val Lys Pro Ser Asn Ala Leu Gly Asn Glu
    690                 695                 700

Arg Ser Gln Ala Lys Leu Ala Asp Phe Gly Leu Ser Arg Ser Phe Pro
705                 710                 715                 720

Val Asp Gly Glu Ser His Val Met Thr Val Val Ala Gly Thr Pro Gly
```

-continued

```
            725                 730                 735

Tyr Leu Asp Pro Glu Tyr Tyr Arg Thr Asn Trp Val Ser Glu Lys Ser
        740                 745                 750

Asp Val Tyr Ser Phe Gly Val Val Leu Leu Glu Ile Val Thr Asn Gln
        755                 760                 765

Pro Gly Met Asn Lys Asn Arg Glu Arg Pro His Ile Asn Glu Trp Val
    770                 775                 780

Met Phe Met Leu Thr Asn Gly Asp Ile Lys Ser Ile Val Asp Pro Lys
785                 790                 795                 800

Leu Asn Glu Asp Tyr Asp Thr Asn Gly Val Trp Lys Val Val Glu Leu
            805                 810                 815

Ala Leu Ala Cys Val Asn Pro Ser Ser Ser Arg Arg Pro Thr Met Pro
            820                 825                 830

His Val Val Met Glu Leu Asn Glu Cys Leu Ala Leu Glu Ile Glu Arg
        835                 840                 845

Lys Gln Gly Ser Gln Ala Thr Tyr Ile Lys Glu Ser Val Glu Phe Ser
    850                 855                 860

Pro Ser Ser Ala Ser Asp Phe Ser Pro Leu Ala Arg
865                 870                 875
```

FUNGAL RESISTANT PLANTS EXPRESSING RLK2

This application is a Continuation of U.S. application Ser. No. 14/419,330, which is the U.S. National Stage application of International Application No. PCT/IB2013/056315, filed Aug. 1, 2013, which claims the benefit of U.S. Provisional Application No. 61/681,165, filed Aug. 9, 2012, and which also claims priority under 35 U.S.C. § 119 to European Patent Application No. 12179878.9, filed Aug. 9, 2012; the entire contents of the aforementioned applications are hereby incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "73923-CON_Seqlisting.txt" created on Jul. 23, 2018, and is 170,409 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the order Pucciniales, for example soybean rust, in plants, plant parts, and/or plant cells. This is achieved by increasing the expression and/or activity of an RLK2 protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the order Pucciniales, for example soybean rust, and to recombinant expression vectors comprising a sequence that is identical or homologous to a sequence encoding an RLK2 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of transmembrane receptor like kinases recognizing conserved pathogen associated molecules (e.g. flagellin or chitin). Receptor-like kinases (RLKs) are signaling proteins that feature an extracellular domain connected via a transmembrane domain to a cytoplasmic kinase. This architecture indicates that RLKs perceive external signals, transducing them into the cell. In plants, RLKs were first implicated in the regulation of development, in pathogen responses, and in recognition events. (Santiago A Morillo and Frans E Tax (2006) Functional analysis of receptor-like kinases in monocots and dicots. Current Opinion in Plant Biology 9:460-469).

Only very few of the RLKs are described to be involved in the recognition of conserved structures of microbes (microbe associated molecular patterns, PAMPs, for review see Thorsten Nurnberger and Birgit Kemmerling (2006) Receptor protein kinases-pattern recognition receptors in plant immunity. TRENDS in Plant Science 11(11)519ff).

Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects).

Another more specific resistance mechanism is based on the presence of so called resistance genes (R-genes). Most R genes belong to the nucleotide-binding site-leucine-rich repeat (NBS-LRR) gene family and function in monitoring the presence of pathogen effector proteins (virulence factors). After recognizing the pathogen derived proteins a strong defense reaction (mostly accompanied by a programmed cell death) is elicited.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora*. The necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races. Therefore there is a strong need to discover R-genes that are derived from non-hosts plants (e.g. *Arabidopsis*) as they are thought to be more durable.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that fungal pathogens, in particular of the order Pucciniales, for example soybean rust, can be controlled by increasing the expression of a RLK2 protein.

The present invention therefore provides a method of increasing resistance against fungal pathogens, preferably against rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more RLK2 nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous RLK2 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust. Surprisingly, we found that resistance against fungal pathogens, in particular of the order Pucciniales, for example soybean rust, can be enhanced by increasing the expression of a RLK2 protein.

The present invention therefore provides a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more RLK2 nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous RLK2 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 3 shows the full-length cDNA sequence of the RLK2 gene from *Arabidopsis thaliana* having SEQ ID NO: 1.

FIG. 4 shows the sequence of a RLK2 protein (SEQ ID NO: 2).

FIG. 5 shows the sequence of the *Arabidopsis thaliana* genomic sequence (part of accession No NC_003070.9) around the region, which codes for RLK2, and having SEQ ID NO: 3.

FIG. 6 shows the alignment of the *Arabidopsis* genome sequence (part of accession No NC_003070.9, SEQ ID NO: 3) and the sequence of the cDNA of RLK2 (SEQ ID NO: 1).

FIG. 7 shows the result of the scoring of 50 transgenic soy plants (derived from 5 independent events) expressing the RLK2 overexpression vector construct. $T_1$ soybean plants expressing RLK2 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 50 soybean $T_1$ plants expressing RLK2 (expression checked by RT-PCR) were evaluated in parallel to non-transgenic control plants. The average of the diseased leaf area is shown in FIG. 7. Overexpression of RLK2 significantly (*: p=0.025) reduces the diseased leaf area in comparison to non-transgenic control plants by 26.0%.

FIG. 8 contains a brief description of the sequences of the sequence listing.

DETAILED DESCRIPTION OF THE INVENTION

Figure 1:
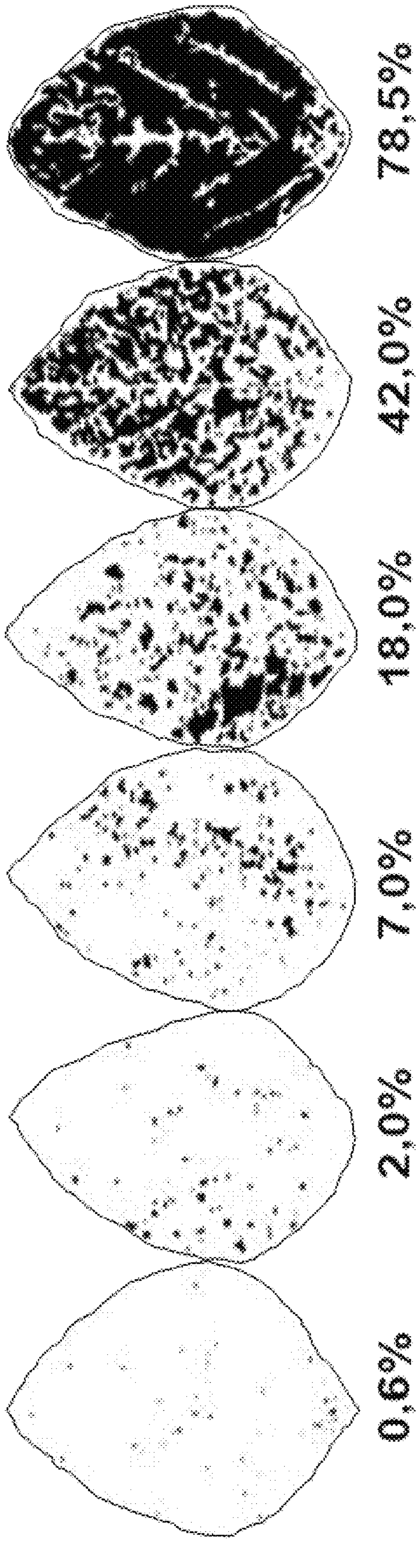
FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular, homologues of a nucleic acid may encompass substitutions on the basis of the degenerative amino acid code.

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below, or Taylor W. R. (1986) The classification of amino acid conservation J Theor Biol., 119:205-18).

TABLE 1

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by non-coding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phakopsoraceae, in particular *Phakopsora pachyrhizi* and *Phakopsora meibomiae*—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous RLK2 nucleic acid, functional fragments thereof and/or an exogenous nucleic acid capable of hybridizing with an RLK2 nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ssRNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole RLK2 nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

"Identity" or "homology" or "similarity" between two nucleic acids sequences or amino acid sequences refers in each case over the entire length of the RLK2 nucleic acid sequences or RLK2 amino acid sequences. The terms "identity", "homology" and "similarity" are used herein interchangeably.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 Apr. 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| FAST algorithm on | |
|---|---|
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index-.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid or protein useful according to the present invention and the RLK2 nucleic acids or RLK2 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous RLK2 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous RLK2 nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more RLK2 nucleic acids, all those constructions brought about by man by genetechnological methods in which either (a) the sequences of the RLK2 nucleic acids or a part thereof, or (b) genetic control sequence(s) which is operably linked with the RLK2 nucleic acid sequence according to the invention, for example a promoter, or (c) a) and b)

are not located in their natural genetic environment or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

A recombinant nucleic acid, expression cassette or vector construct preferably comprises a natural gene and a natural promoter, a natural gene and a non-natural promoter, a non-natural gene and a natural promoter, or a non-natural gene and a non-natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous RLK2 nucleic acid, recombinant construct, vector or expression cassette including one or more RLK2 nucleic acids is integrated into the genome by means of genetechnology.

Preferably, constructs or vectors or expression cassettes are not present in the genome of the original plant or are present in the genome of the transgenic plant not at their natural locus of the genome of the original plant.

A "wild type" plant, "wild type" plant part, or "wild type" plant cell means that said plant, plant part, or plant cell does not express exogenous RLK2 nucleic acid or exogenous RLK2 protein.

Natural locus means the location on a specific chromosome, preferably the location between certain genes, more preferably the same sequence background as in the original plant which is transformed.

Preferably, the transgenic plant, plant cell or tissue thereof expresses the RLK2 nucleic acids, RLK2 constructs or RLK2 expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the RLK2 nucleic acids has an identity as defined above over a length of at least 20%, at least 30%, at least 50%, at least 75%, at least 90% of the nucleotides of the respective RLK2 nucleic acid.

The term "splice variant" as used herein encompasses variants of a nucleic acid sequence in which selected introns and/or exons or parts thereof have been excised, replaced, displaced or added, or in which introns have been shortened or lengthened. Thus, a splice variant can have one or more or even all introns removed or added or partially removed or partially added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the RLK2 nucleotide sequence as defined by SEQ ID NO: 1 or the RLK2 protein sequence as defined by SEQ ID NO: 2.

The term "increased activity" or "enhanced activity" as used herein means any protein having increased activity and which provides an increased fungal resistance compared with the wildtype plant merely expressing the respective endogenous RLK2 nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

RLK2 Nucleic Acids

The RLK2 nucleic acid to be overexpressed in order to achieve increased resistance to fungal pathogens, e.g., of the family Phakopsoraceae, for example soybean rust, is preferably a nucleic acid coding for an RLK2 protein, and is preferably as defined by SEQ ID NO: 1, 3, 4, 5-20, 21, 23, 25, 27, 29, 31, 33, or 35, or a fragment, homolog, derivative, orthologue or paralogue thereof, or a splice variant thereof. Preferably, the nucleic acid coding for an RLK2 protein of the present invention has at least 60% identity, preferably at least 70% sequence identity, at least 80%, at least 90%, at least 95%, at least 98%, at least 99% sequence identity, or even 100% sequence identity with SEQ ID NO: 1, 3, 4, 5-20, 21, 23, 25, 27, 29, 31, 33, or 35, or is a functional fragment thereof, or a splice variant thereof. Most preferred is at least 90% identity, at least 95% identity, more preferred is at least 98% or at least 99% identity with SEQ ID NO: 1, 3, 4, 5-20, 21, 23, 25, 27, 29, 31, 33, or 35.

Preferably, the RLK2 nucleic acid to be overexpressed in order to achieve increased resistance to fungal pathogens, e.g., of the family Phakopsoraceae, for example soybean rust, is preferably a nucleic acid coding for a RLK2 protein, and is preferably as defined by SEQ ID NO: 3, or a fragment, homolog, derivative, orthologue or paralogue thereof, or a splice variant thereof. Preferably, the nucleic acid coding for a RLK2 protein of the present invention has at least 60% identity, preferably at least 70% sequence identity, at least 80%, at least 90%, at least 95%, at least 98%, at least 99% sequence identity, or even 100% sequence identity with SEQ ID NO: 3 or is a functional fragment thereof, or a splice variant thereof. Most preferred is at least 90% identity, at least 95% identity, more preferred is at least 98% or at least 99% identity with SEQ ID NO: 3.

More preferably, the RLK2 nucleic acid to be overexpressed in order to achieve increased resistance to fungal pathogens, e.g., of the family Phakopsoraceae, for example soybean rust, is preferably a nucleic acid coding for a RLK2 protein, and is preferably as defined by SEQ ID NO: 1, or a fragment, homolog, derivative, orthologue or paralogue thereof, or a splice variant thereof. Preferably, the nucleic acid coding for a RLK2 protein of the present invention has at least 60% identity, preferably at least 70% sequence identity, at least 80%, at least 90%, at least 95%, at least 98%, at least 99% sequence identity, or even 100% sequence identity with SEQ ID NO: 1 or is a functional fragment thereof, or a splice variant thereof. Most preferred is at least 95% identity, more preferred is at least 98% or at least 99% identity with SEQ ID NO: 1.

Preferably, the RLK2 nucleic acid to be overexpressed in order to achieve increased resistance to fungal pathogens, e.g., of the family Phakopsoraceae, for example soybean rust, is preferably a nucleic acid coding for a RLK2 protein, and is preferably as defined by SEQ ID NO: 4, or a fragment, homolog, derivative, orthologue or paralogue thereof, or a splice variant thereof. Preferably, the nucleic acid coding for a RLK2 protein of the present invention has at least 60% identity, preferably at least 70% sequence identity, at least 80%, at least 90%, at least 95%, at least 98%, at least 99% sequence identity, or even 100% sequence identity with SEQ ID NO: 4 or is a functional fragment thereof, or a splice variant thereof. Most preferred is at least 90% identity, at least 95% identity, more preferred is at least 98% or at least 99% identity with SEQ ID NO: 4.

Preferably the RLK2 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, 1, 3, 5-20, 21, 23, 25, 27, 29, 31, 33, or 35, or a functional fragment, derivative, orthologue, or paralogue thereof, or a splice variant thereof;

(ii) a nucleic acid encoding a RLK2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 22, 24, 26, 28, 30, 32, 34, or 36, or a functional fragment, derivative, orthologue, or paralogue thereof; preferably the RLK2 protein has essentially the same biological activity as a RLK2 protein encoded by SEQ ID NO: 4, 1, 3, 5-20, 21, 23, 25, 27, 29, 31, 33, or 35; preferably the RLK2 protein confers enhanced fungal resistance relative to control plants; preferably the RLK2 protein has receptor like kinase activity;

(iii) a nucleic acid molecule which hybridizes with a complementary sequence of any of the nucleic acid molecules of (i) or (ii) under high stringency hybridization conditions; preferably encoding a RLK2 protein; preferably wherein the nucleic acid molecule codes for a polypeptide which has essentially identical properties to the polypeptide described in SEQ ID NO: 2, 22, 24, 26, 28, 30, 32, 34, or 36; preferably the encoded protein confers enhanced fungal resistance relative to control plants; and (iv) a nucleic acid encoding the same RLK2 protein as the RLK2 nucleic acids of (i) to (iii) above, but differing from the RLK2 nucleic acids of (i) to (iii) above due to the degeneracy of the genetic code.

Preferably, the nucleic acid coding for a RLK2 protein of the present invention has at least 60% identity, preferably at least 70% sequence identity, at least 80%, at least 90%, at least 95%, at least 98%, at least 99% sequence identity, or even 100% sequence identity with SEQ ID NO: 1. Most preferred is at least 95% identity, more preferred is at least 98% or at least 99% identity with SEQ ID NO: 1.

Preferably, the nucleic acid coding for a RLK2 protein of the present invention has at least 60% identity, preferably at least 70% sequence identity, at least 80%, at least 90%, at least 95%, at least 98%, at least 99% sequence identity, or even 100% sequence identity with SEQ ID NO: 4. Most preferred is at least 95% identity, more preferred is at least 98% or at least 99% identity with SEQ ID NO: 4.

Preferably the RLK2 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof;

(ii) a nucleic acid encoding a RLK2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the RLK2 protein has essentially the same biological activity as a RLK2 protein encoded by SEQ ID NO: 1, preferably the RLK2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same RLK2 protein as the RLK2 nucleic acids of (i) to (iii) above, but differing from the RLK2 nucleic acids of (i) to (iii) above due to the degeneracy of the genetic code.

Preferably the RLK2 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, or a functional fragment, derivative, orthologue, or paralogue thereof, or a splice variant thereof;

(ii) a nucleic acid encoding a RLK2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the RLK2 protein has essentially the same biological activity as a RLK2 protein encoded by SEQ ID NO: 4, preferably the RLK2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same RLK2 protein as the RLK2 nucleic acids of (i) to (iii) above, but differing from the RLK2 nucleic acids of (i) to (iii) above due to the degeneracy of the genetic code.

Percentages of identity of a nucleic acid are indicated with reference to the entire nucleotide region given in a sequence specifically disclosed herein.

Preferably the portion of the RLK2 nucleic acid is about 1500-1600, about 1600-1700, about 1700-1800, about 1800-1900, about 1900-1995, about 1900-2000, about 2000-2200, about 2200-2400, about 2400-2600, about 2600-2800, about 2800-3000, about 3000-3200, about 3200-3400, about 3400-3600, about 3600-3800, or about 3800-3871 nucleotides, preferably consecutive nucleotides, preferably counted from the 5' or 3' end of the nucleic acid, in length, of the nucleic acid sequences given in SEQ ID NO: 4, 1, 3, 5-20, 21, 23, 25, 27, 29, 31, 33, or 35.

Preferably, the RLK2 nucleic acid comprises at least about 1500, at least about 1600, at least about 1700, at least about 1800, at least about 1900, at least about 2000, at least about 2200, at least about 2400, at least about 2600, at least about 2800, at least about 3000, at least about 3200, at least about 3400, at least about 3600, or at least about 3800 nucleotides, preferably continuous nucleotides, preferably counted from the 5' or 3' end of the nucleic acid or up to the full length of the nucleic acid sequence set out in SEQ ID NO: 4, 1, 3, 5-20, 21, 23, 25, 27, 29, 31, 33, or 35.

Preferably, the RLK2 nucleic acid comprises at least about 1000, at least about 1200, at least about 1400, at least about 1600, at least about 1800, at least about 2000, at least about 2100, at least about 2200, at least about 2300, at least about 2400, at least about 2500, or at least about 2600 nucleotides, preferably continuous nucleotides, preferably counted from the 5' or 3' end of the nucleic acid or up to the full length of the nucleic acid sequence set out in SEQ ID NO: 1.

Preferably the portion of the RLK2 nucleic acid is about 1000-1100, about 1100-1200, about 1200-1300, about 1300-1400, about 1400-1500, about 1500-1600, about 1600-1700, about 1700-1800, about 1800-1900, about 1900-2000, about 2000-2100, about 2100-2200, about 2200-2300, about 2300-2400, about 2400-2500, about 2500-2600, or about 2600-2631 nucleotides, preferably consecutive nucleotides, preferably counted from the 5' or 3' end of the nucleic acid, in length, of the nucleic acid sequences given in SEQ ID NO: 1.

Preferably, the RLK2 nucleic acid comprises at least about 1000, at least about 1200, at least about 1400, at least about 1600, at least about 1800, at least about 2000, at least about 2100, at least about 2200, at least about 2300, at least about 2400, at least about 2500, or at least about 2600 nucleotides, preferably continuous nucleotides, preferably counted from the 5' or 3' end of the nucleic acid or up to the full length of the nucleic acid sequence set out in SEQ ID NO: 4.

Preferably the portion of the RLK2 nucleic acid is about 1000-1100, about 1100-1200, about 1200-1300, about 1300-1400, about 1400-1500, about 1500-1600, about 1600-1700, about 1700-1800, about 1800-1900, about 1900-2000, about 2000-2100, about 2100-2200, about 2200-2300, about 2300-2400, about 2400-2500, about 2500-2600, or about 2600-2631 nucleotides, preferably consecutive nucleotides, preferably counted from the 5' or 3' end of the nucleic acid, in length, of the nucleic acid sequences given in SEQ ID NO: 4.

Preferably, the RLK2 nucleic acid is a RLK2 nucleic acid splice variant. Preferred splice variants are splice variants of a nucleic acid represented by SEQ ID NO: 3. Preferred RLK2 nucleic acids being a splice variant of SEQ ID NO: 3 are shown in FIG. 6.

Preferably, the RLK2 nucleic acid is an isolated nucleic acid molecule comprising a splice variant of SEQ ID NO: 3, wherein the splice variant is selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof;

(ii) a nucleic acid encoding a RLK2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the RLK2 protein has essentially the same biological activity as a RLK2 protein encoded by SEQ ID NO: 1 or 3; preferably the RLK2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same RLK2 protein as the RLK2 nucleic acids of (i) to (iii) above, but differing from the RLK2 nucleic acids of (i) to (iii) above due to the degeneracy of the genetic code.

Preferred splice variants of SEQ ID NO: 3 consist of or comprise the nucleotide sequence shown in SEQ ID NO: 1.

Preferably the RLK2 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3, or a splice variant thereof;

(ii) a nucleic acid molecule which hybridizes with a complementary sequence of any of the nucleic acid molecules of (i) or (ii) under high stringency hybridization conditions; preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants;

(iii) a nucleic acid encoding the same RLK2 protein as the RLK2 nucleic acids of (i) to (iii) above, but differing from the RLK2 nucleic acids of (i) to (iii) above due to the degeneracy of the genetic code;

wherein the splice variant is selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof;

(ii) a nucleic acid encoding a RLK2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the RLK2 protein has essentially the same biological activity as a RLK2 protein encoded by SEQ ID NO: 1 or 3; preferably the RLK2 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same RLK2 protein as the RLK2 nucleic acids of (i) to (iii) above, but differing from the RLK2 nucleic acids of (i) to (iii) above due to the degeneracy of the genetic code.

More preferably the RLK2 nucleic acid is an isolated nucleic acid molecule comprising a nucleic acid selected from the group consisting of:

a nucleic acid having in increasing order of preference least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3, or a splice variant thereof;

wherein the splice variant thereof has in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1.

The RLK2 nucleic acids described herein are useful in the constructs, methods, plants, harvestable parts and products of the invention.

RLK2 Proteins

The RLK2 protein is preferably defined by SEQ ID NO: 2, 22, 24, 26, 28, 30, 32, 34, or 36, or a fragment, homolog, derivative, orthologue or paralogue thereof. Preferably, the RLK2 protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 2, 22, 24, 26, 28, 30, 32, 34, or 36 or a functional fragment thereof. More preferably, the RLK2 protein of the present invention has at least 60%, preferably at least 70% sequence identity, at least 80%, at least 90%, at least 95%, at least 98%, at least 99% sequence identity, or even 100% sequence identity with SEQ ID NO: 2, 22, 24, 26, 28, 30, 32, 34, or 36, or is a functional fragment thereof, an orthologue or a paralogue thereof. Most preferred is at least 90% identity, least 95% identity, more preferred is at least 98% or at least 99% identity with SEQ ID NO: 2, 22, 24, 26, 28, 30, 32, 34, or 36.

Preferably, the RLK2 protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 22, 24, 26, 28, 30, 32, 34, or 36, or a functional fragment, derivative, orthologue, or paralogue thereof; preferably the RLK2 protein has essentially the same biological activity as a RLK2 protein encoded by SEQ ID NO: 1 or 3; preferably the RLK2 protein confers enhanced fungal resistance relative to control plants; preferably the RLK2 protein has receptor like kinase activity; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, 1, 3, 5-20, 21, 23, 25, 27, 29, 31, 33, or 35, or a functional fragment, derivative, orthologue, or paralogue thereof, or a splice variant thereof; preferably the RLK2 protein confers enhanced fungal resistance relative to control plants; preferably the RLK2 protein has receptor like kinase activity.

Preferably, the RLK2 protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the RLK2 protein has essentially the same biological activity as a RLK2 protein encoded by SEQ ID NO: 1 or 3; preferably the RLK2 protein confers enhanced fungal resistance relative to control plants; preferably the RLK2 protein has receptor like kinase activity; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, 1, 3, 5-20, 21, 23, 25, 27, 29, 31, 33, or 35, or a functional fragment, derivative, orthologue, or paralogue thereof, or a splice variant thereof; preferably the RLK2 protein confers enhanced fungal resistance relative to control plants; preferably the RLK2 protein has receptor like kinase activity.

Preferably, the RLK2 protein is a protein comprising an amino acid sequence selected from the group consisting of:

(i) an amino acid sequence having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, or a functional fragment, derivative, orthologue, or paralogue thereof; preferably the RLK2 protein has essentially the same biological activity as a RLK2 protein encoded by SEQ ID NO: 1 or 3; preferably the RLK2 protein confers enhanced fungal resistance relative to control plants; or (ii) an amino acid sequence encoded by a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof; preferably the RLK2 protein confers enhanced fungal resistance relative to control plants.

A preferred derivative of a RLK2 protein is a RLK2 protein consisting of or comprising an amino acid sequence selected from the group consisting of:

an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence represented by SEQ ID NO: 2, wherein the non-identical amino acid residues are conservative amino acid substitutions, preferably as shown in Table 1, of the corresponding amino acid residue of SEQ ID NO: 2; preferably the RLK2 protein has essentially the same biological activity as SEQ ID NO: 2 or as a RLK2 protein encoded by SEQ ID NO: 1 or 3; preferably the RLK2 protein confers enhanced fungal resistance relative to control plants.

Preferably, the RLK2 protein consists of or comprises an amino acid sequence represented by SEQ ID NO: 2 with one or more conservative amino acid substitutions, preferably as shown in Table 1, of the corresponding amino acid residues of SEQ ID NO: 2. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 1-10, 10-20, 20-30, 40-50, 50-60, 60-70, 70-80, 80-90, 90-100, 100-110, 110-120, or 120-130 amino acid residues of SEQ ID NO: 2 are conservative amino acid substitutions, preferably as shown in Table 1, of the corresponding amino acid residue of SEQ ID NO: 2.

More preferably, the RLK2 protein consists of or comprises an amino acid sequence having at least 80%, at least 85%, at least 90%, at least 95%, at least 98% or at least 99% sequence identity with an amino acid sequence as represented by SEQ ID NO: 2, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the non-identical amino acid residues, or wherein 1-10, 10-20, 20-30, 40-50, 50-60, 60-70, 70-80, 80-90 or 90-100 or even all of the non-identical amino acid residues are conservative amino acid substitutions, preferably as shown in Table 1, of the corresponding amino acid residue of SEQ ID NO: 2.

Percentages of identity of a polypeptide or protein are indicated with reference to the entire amino acid sequence specifically disclosed herein.

Preferably, the RLK2 protein comprises at least about 450, at least about 500, at least about 520, at least about 540, at least about 560, at least about 580, at least about 600, at least about 620, at least about 640, at least about 660, at least about 680, at least about 700, at least about 720, at least about 740, at least about 760, at least about 780, at least about 780, at least about 800, at least about 810, at least about 820, at least about 830, at least about 840, at least about 850, at least about 860, or at least about 870 amino acid residues, preferably continuous amino acid residues, preferably counted from the N-terminus or the C-terminus of the amino acid sequence, or up to the full length of the amino acid sequence set out in SEQ ID NO: 2, 22, 24, 26, 28, 30, 32, 34, or 36.

Preferably, the RLK2 polypeptide comprises about 300-400, about 400-500, about 500-520, about 520-540, about 540-560, about 560-580, about 580-600, about 600-620, about 620-640, about 640-660, about 660-680, about 680-700, about 700-720, about 740-760, about 760-780, about 780-800, about 810-820, about 820-830, about 830-840, about 840-850, about 850-860, about 860-870, or about 870-876 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 2, 22, 24, 26, 28, 30, 32, 34, or 36.

Preferably, the RLK2 protein comprises at least about 450, at least about 500, at least about 520, at least about 540, at least about 560, at least about 580, at least about 600, at least about 620, at least about 640, at least about 660, at least about 680, at least about 700, at least about 720, at least about 740, at least about 760, at least about 780, at least about 780, at least about 800, at least about 810, at least about 820, at least about 830, at least about 840, at least about 850, at least about 860, or at least about 870 amino acid residues, preferably continuous amino acid residues, preferably counted from the N-terminus or the C-terminus of the amino acid sequence, or up to the full length of the amino acid sequence set out in SEQ ID NO: 2.

Preferably, the RLK2 polypeptide comprises about 300-400, about 400-500, about 500-520, about 520-540, about 540-560, about 560-580, about 580-600, about 600-620, about 620-640, about 640-660, about 660-680, about 680-700, about 700-720, about 740-760, about 760-780, about 780-800, about 810-820, about 820-830, about 830-840, about 840-850, about 850-860, about 860-870, or about 870-876 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 2.

The RLK2 proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phakopsoraceae, for example soy bean rust, in a plant, plant part, or plant cell by increasing the expression of an RLK2 protein or a functional fragment, orthologue, paralogue or homologue thereof in comparison to wild-type plants, wild-type plant parts or wild-type plant cells.

The present invention also provides a method for increasing resistance to fungal pathogens, in particular a heminecrotrophic pathogen, in particular to rust pathogens (i.e., fungal pathogens of the order Pucciniales), preferably fungal pathogens of the family Phakopsoraceae, preferably against fungal pathogens of the genus *Phakopsora*, most preferably against *Phakopsora pachyrhizi* and *Phakopsora meibomiae*, also known as soy bean rust in plants or plant cells, wherein in comparison to wild type plants, wild type plant parts, or wild type plant cells an RLK2 protein is overexpressed.

The present invention further provides a method for increasing resistance to fungal pathogens of the genus *Phakopsora*, most preferably against *Phakopsora pachyrhizi* and *Phakopsora meibomiae*, also known as soy bean rust in plants or plant cells by overexpression of an RLK2 protein.

In preferred embodiments, the protein amount and/or function of the RLK2 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the RLK2 nucleic acid.

In one embodiment of the invention, the RLK2 protein is encoded by (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 4, 1, 3, 5-20, 21, 23, 25, 27, 29, 31, 33, or 35, a functional fragment thereof, or an orthologue or a paralogue thereof, or a splice variant thereof; or by (ii) an exogenous nucleic acid encoding a protein having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 2, 22, 24, 26, 28, 30, 32, 34, or 36, a functional fragment thereof, an orthologue or a paralogue thereof, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; or by (iv) an exogenous nucleic acid encoding the same RLK2 protein as any of the nucleic acids of (i) to (iii) above, but differing from the nucleic acids of (i) to (iii) above due to the degeneracy of the genetic code.

A method for increasing fungal resistance, preferably resistance to Phakopsoraceae, for example soy bean rust, in a plant, plant part, or plant cell, by increasing the expression of an RLK2 protein or a functional fragment, orthologue, paralogue or homologue thereof, or a splice variant thereof, wherein the RLK2 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 5-20, 21, 23, 25, 27, 29, 31, 33, or 35, or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, 22, 24, 26, 28, 30, 32, 34, or 36, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same RLK2 protein as any of the nucleic acids of (i) to (iii) above, but differing from the nucleic acids of (i) to (iii) above due to the degeneracy of the genetic code is a further embodiment of the invention.

A method for increasing fungal resistance, preferably resistance to Phakopsoraceae, for example soy bean rust, in a plant, plant part, or plant cell, by increasing the expression of a RLK2 protein or a functional fragment, orthologue, paralogue or homologue thereof, or a splice variant thereof, wherein the RLK2 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same RLK2 protein as any of the nucleic acids of (i) to (iii) above, but differing from the nucleic acids of (i) to (iii) above due to the degeneracy of the genetic code is a further embodiment of the invention.

A method for increasing fungal resistance, preferably resistance to Phakopsoracea, for example soy bean rust, in a plant, plant part, or plant cell, by increasing the expression of a RLK2 protein or a functional fragment, orthologue, paralogue or homologue thereof, or a splice variant thereof, wherein the RLK2 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same RLK2 protein as any of the nucleic acids of (i) to (iii) above, but differing from the nucleic acids of (i) to (iii) above due to the degeneracy of the genetic code is a further embodiment of the invention.

In a further method of the invention, the method comprises the steps of (a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 5-20, 21, 23, 25, 27, 29, 31, 33, or 35, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 22, 24, 26, 28, 30, 32, 34, or 36, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
  (iv) a nucleic acid encoding the same RLK2 polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for an RLK2 protein is expressed in an amount and for a period sufficient to generate or to increase soybean rust resistance in said plant.

Preferably, the method comprises the steps of (a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
  (iv) a nucleic acid encoding the same RLK2 polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for a RLK2 protein is expressed in an amount and for a period sufficient to generate or to increase soybean rust resistance in said plant.

Preferably, the method comprises the steps of (a) stably transforming a plant cell with a recombinant expression cassette comprising
  (i) a nucleic acid having at least 60% identity, preferably at least 70% sequence identity, at least 80%, at least 90%, at least 95%, at least 98%, at least 99% sequence identity, or even 100% sequence identity with SEQ ID NO: 4, or a functional fragment thereof, or an orthologue or a paralogue thereof, or a splice variant thereof;
  (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, a functional fragment thereof, an orthologue or a paralogue thereof; preferably the encoded protein confers enhanced fungal resistance relative to control plants;
  (iii) a nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or
  (iv) a nucleic acid encoding the same RLK2 polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for a RLK2 protein is expressed in an amount and for a period sufficient to generate or to increase soybean rust resistance in said plant.

Preferably, the method for increasing fungal resistance, preferably resistance to Phakopsoracea, for example soy bean rust, in a plant, plant part, or plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 5-20, 21, 23, 25, 27, 29, 31, 33, or 35, or a functional fragment thereof, or an orthologue or a paralogue thereof, or a splice variant thereof;

(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 22, 24, 26, 28, 30, 32, 34, or 36, a functional fragment thereof, an orthologue or a paralogue thereof; preferably the encoded protein confers enhanced fungal resistance relative to control plants;

(iii) an exogenous nucleic acid capable of hybridizing under stringent conditions a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) an exogenous nucleic acid encoding the same RLK2 polypeptide as any of the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of an RLK2 protein, wherein the RLK2 protein is encoded by (i) an exogenous nucleic acid having at least 80%, at least 90%, at least 95%, at least 98%, at least 99% sequence identity, or even 100% sequence identity with SEQ ID NO: 4, 1, 3, 5-20, 21, 23, 25, 27, 29, 31, 33, or 35;

(ii) an exogenous nucleic acid encoding a protein having at least 80%, at least 90%, at least 95%, at least 98%, at least 99% sequence identity, or even 100% sequence identity with SEQ ID NO: 2, 22, 24, 26, 28, 30, 32, 34, or 36; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same RLK2 protein as any of the nucleic acids of (i) to (iii) above, but differing from the nucleic acids of (i) to (iii) above due to the degeneracy of the genetic code, wherein increasing the expression of the RLK2 protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of an RLK2 protein, wherein the RLK2 protein is encoded by (i) an exogenous nucleic acid having at least 80%, at least 90%, at least 95%, at least 98%, at least 99% sequence identity, or even 100% sequence identity with SEQ ID NO: 4, 1, 3, 5-20, 21, 23, 25, 27, 29, 31, 33, or 35;

(ii) an exogenous nucleic acid encoding a protein having at least 80%, at least 90%, at least 95%, at least 98%, at least 99% sequence identity, or even 100% sequence identity with SEQ ID NO:2, 22, 24, 26, 28, 30, 32, 34, or 36; preferably the encoded protein confers enhanced fungal resistance relative to control plants; or (iii) an exogenous nucleic acid encoding the same RLK2 protein as any of the nucleic acids of (i) to (ii) above, but differing from the nucleic acids of (i) to (ii) above due to the degeneracy of the genetic code, wherein increasing the expression of the RLK2 protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi, P. meibomiae* |
| Rust (tropical corn) | *Physopella pallescens, P. zeae = Angiopsora zeae* |

TABLE 3

Diseases caused by necrotrophic and/or hemibiotrophic fungi and Oomycetes

| Disease | Pathogen |
|---|---|
| Plume blotch | *Septoria* (*Stagonospora*) *nodorum* |
| Leaf blotch | *Septoria tritici* |
| Ear fusarioses | *Fusarium* spp. |
| Late blight | *Phytophthora infestans* |
| Anthrocnose leaf blight | *Colletotrichum graminicola* |
| Anthracnose stalk rot | (teleomorph: *Glomerella graminicola Politis*); *Glomerella tucumanensis* (anamorph: *Glomerella falcatum Went*) |
| *Curvularia* leaf spot | *Curvularia clavata, C. eragrostidis, = C. maculans* (teleomorph: *Cochliobolus eragrostidis*), *Curvularia inaequalis, C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis, C. tuberculata* (teleomorph: *Cochliobolus tuberculatus*) |
| *Didymella* leaf spot | *Didymella exitalis* |
| *Diplodia* leaf spot or streak | *Stenocarpella macrospora = Diplodia* leaf *macrospora* |
| Brown stripe downy mildew | *Sclerophthora rayssiae* var. *zeae* |

TABLE 3-continued

| Diseases caused by necrotrophic and/or hemibiotrophic fungi and Oomycetes | |
|---|---|
| Disease | Pathogen |
| Crazy top downy mildew | *Sclerophthora macrospora = Sclerospora macrospora* |
| Green ear downy mildew (*graminicola* downy mildew) | *Sclerospora graminicola* |
| Leaf spots, minor | *Alternaria alternata*, *Ascochyta maydis*, *A. tritici*, *A. zeicola*, *Bipolaris victoriae = Helminthosporium victoriae* (teleomorph: *Cochliobolus victoriae*), *C. sativus* (anamorph: *Bipolaris sorokiniana = H. sorokinianum = H. sativum*), *Epicoccum nigrum*, *Exserohilum prolatum = Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum = Helminthosporium turcicum*) |
| Northern corn leaf spot *Helminthosporium* ear rot (race 1) | *Cochliobolus carbonum* (anamorph: *Bipolaris zeicola = Helminthosporium carbonum*) |
| *Phaeosphaeria* leaf spot | *Phaeosphaeria maydis = Sphaerulina maydis* |
| *Rostratum* leaf spot (*Helminthosporium* leaf disease, ear and stalk rot) | *Setosphaeria rostrata*, (anamorph: *xserohilum rostratum = Helminthosporium rostratum*) |
| Java downy mildew | *Peronosclerospora maydis = Sclerospora maydis* |
| Philippine downy mildew | *Peronosclerospora philippinensis = Sclerospora philippinensis* |
| *Sorghum* downy mildew | *Peronosclerospora sorghi = Sclerospora sorghi* |
| Spontaneum downy mildew | *Peronosclerospora spontanea = Sclerospora spontanea* |
| Sugarcane downy mildew | *Peronosclerospora sacchari = Sclerospora sacchari* |
| *Sclerotium* ear rot (southern blight) | *Sclerotium rolfsii Sacc.* (teleomorph: *Athelia rolfsii*) |
| Seed rot-seedling blight | *Bipolaris sorokiniana*, *B. zeicola = Helminthosporium carbonum*, *Diplodia maydis*, *Exserohilum pedicillatum*, *Exserohilum turcicum = Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

The following are especially preferred:

- Plasmodiophoromycota such as *Plasmodiophora brassicae* (clubroot of crucifers), *Spongospora subterranea, Polymyxa graminis,*
- Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.
- Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f. sp. *hordei*) and wheat (f. sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).
- Basidiomycetes such as *Typhula incarnata* (typhula blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (rhizoctonia root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).
- Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (verticillium wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales, preferably the group Uredinales (rusts), among which in particular the Melompsoraceae. Preferred are Phakopsoraceae, more preferably *Phakopsora*. Especially preferred are *Phakopsora pachyrhizi* and/or *Phakopsora meibomiae.*

Also preferred rust fungi are selected from the group of *Puccinia, Gymnosporangium, Juniperus, Cronartium, Hemileia*, and *Uromyces*; preferably *Puccinia sorghi, Gymnosporangium juniperi-virginianae, Juniperus virginiana, Cronartium ribicola, Hemileia vastatrix, Puccinia graminis,*

*Puccinia coronata, Uromyces phaseoli, Puccinia hemerocallidis, Puccinia persistens* subsp. *Triticina, Puccinia striiformis, Puccinia graminis* causes, and/or *Uromyces appendeculatus*.

RLK2 Expression Constructs and Vector Constructs

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 5-20, 21, 23, 25, 27, 29, 31, 33, or 35, or a functional fragment thereof, or an orthologue or a paralogue thereof, or a splice variant thereof;

(ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 22, 24, 26, 28, 30, 32, 34, or 36, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) a nucleic acid encoding the same RLK2 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 4, 1, 3, 5-20, 21, 23, 25, 27, 29, 31, 33, or 35;

(ii) a nucleic acid coding for a protein having at least 80%, at least 90%, at least 95%, at least 98%, at least 99% sequence identity, or even 100% sequence identity with SEQ ID NO: 2, 22, 24, 26, 28, 30, 32, 34, or 36; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) a nucleic acid encoding the same RLK2 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 1;

(ii) a nucleic acid coding for a protein having at least 80%, at least 90%, at least 95%, at least 98%, at least 99% sequence identity, or even 100% sequence identity with SEQ ID NO: 2; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) a nucleic acid encoding the same RLK2 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 4;

(ii) a nucleic acid coding for a protein having at least 80%, at least 90%, at least 95%, at least 98%, at least 99% sequence identity, or even 100% sequence identity with SEQ ID NO: 2; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) a nucleic acid encoding the same RLK2 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

Especially preferred is a promoter from parsley, preferably, the parsley ubiquitine promoter. A preferred terminator is the terminator of the cathepsin D inhibitor gene from *Solanum tuberosum.*

In preferred embodiments, the increase in the protein amount and/or activity of the RLK2 protein takes place in a constitutive or tissue-specific manner. In especially preferred embodiments, an essentially pathogen-induced increase in the protein amount and/or protein activity takes place, for example by recombinant expression of the RLK2 nucleic acid under the control of a fungal-inducable promoter. In particular, the expression of the RLK2 nucleic acid takes place on fungal infected sites, where, however, preferably the expression of the RLK2 nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:

WIR5 (=GstA1); acc. X56012; Dudler & Schweizer,

GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998), GLP2a, acc. AJ237942, Schweizer P., Christoffel A. and Dudler R., Plant J. 20, 541 (1999);

Prx7, acc. AJ003141, Kristensen B. K., Ammitzböll H., Rasmussen S. K. and Nielsen K. A., Molecular Plant Pathology, 2(6), 311 (2001);

GerA, acc. AF250933; Wu S., Druka A., Horvath H., Kleinhofs A., Kannangara G. and von Wettstein D., Plant Phys Biochem 38, 685 (2000);

OsROC1, acc. AP004656

RTBV, acc. AAV62708, AAV62707; Klöti A., Henrich C., Bieri S., He X., Chen G., Burkhardt P. K., Minn J., Lucca P., Hohn T., Potrykus I. and Fütterer J., PMB 40, 249 (1999);

Chitinase ChtC2-Promoter from potato (Ancillo et al., Planta. 217(4), 566, (2003));

AtProT3 Promoter (Grallath et al., Plant Physiology. 137(1), 117 (2005));

SHN-Promoters from *Arabidopsis* (AP2/EREBP transcription factors involved in cutin and wax production) (Aaron et al., Plant Cell. 16(9), 2463 (2004)); and/or GSTA1 from wheat (Dudler et al., WP2005306368 and Altpeter et al., Plant Molecular Biology. 57(2), 271 (2005)).

Mesophyll-specific promoters may be selected from the group consisting of:

PPCZm1 (=PEPC); Kausch A. P., Owen T. P., Zachwieja S. J., Flynn A. R. and Sheen J., Plant Mol. Biol. 45, 1 (2001);

OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);

OsPPDK, acc. AC099041;

TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1b, acc. X74940; Bryngelsson et al., Mol. Plant Microbe Interact. 7(2), 267 (1994);
HvB1,3gluc; acc. AF479647;
HvPrx8, acc. AJ276227; Kristensen et al., Molecular Plant Pathology, 2(6), 311 (2001); and/or
HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of

PcUbi promoter from parsley (WO 03/102198)
CaMV 35S promoter: Cauliflower Mosaic Virus 35S promoter (Benfey et al. 1989 EMBO J. 8(8): 2195-2202),
STPT promoter: *Arabidopsis thaliana* Short Triose phosphate translocator promoter (Accession NM_123979)
Act1 promoter: *Oryza sativa* actin 1 gene promoter (McElroy et al. 1990 PLANT CELL 2(2) 163-171 a) and/or
EF1A2 promoter: *Glycine max* translation elongation factor EF1 alpha (US 20090133159).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

In preferred embodiments, the increase in the protein quantity or function of the RLK2 protein takes place in a constitutive or tissue-specific manner. In especially preferred embodiments, an essentially pathogen-induced increase in the protein quantity or protein function takes place, for example by exogenous expression of the RLK2 nucleic acid under the control of a fungal-inducible promoter. In particular, the expression of the RLK2 nucleic acid takes place on fungal infected sites, where, however, preferably the expression of the RLK2 nucleic acid sequence remains essentially unchanged in tissues not infected by fungus. In preferred embodiments, the protein amount of an RLK2 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the RLK2 nucleic acid.

A preferred embodiment is the use of an expression construct or a vector as described herein for the transformation of a plant, plant part, or plant cell to provide a pathogen resistant plant, plant part, or plant cell. Thus, a preferred embodiment is the use of an expression construct or a vector as described herein for increasing pathogen resistance in a plant, plant part, or plant cell compared to a control plant, plant part, or plant cell.

Transgenic Organisms; Transgenic Plants, Plant Parts, and Plant Cells

A preferred embodiment is a transgenic plant, transgenic plant part, or transgenic plant cell overexpressing an exogenous RLK2 protein. Preferably, the RLK2 protein overexpressed in the plant, plant part or plant cell is encoded by (i) an exogenous nucleic acid having at least 60% identity with SEQ ID NO: 4, 1, 3, 5-20, 21, 23, 25, 27, 29, 31, 33, or 35, or a functional fragment, thereof, an orthologue or a paralogue thereof, or a splice variant thereof; or by
(ii) an exogenous nucleic acid encoding a protein having at least 60% identity with SEQ ID NO: 2, 22, 24, 26, 28, 30, 32, 34, or 36, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
(iv) an exogenous nucleic acid encoding the same RLK2 protein as any of the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 80%, at least 90%, at least 95%, at least 98%, at least 99% sequence identity, or even 100% sequence identity with SEQ ID NO: 2.

A preferred embodiment is a transgenic plant, transgenic plant part, or transgenic plant cell overexpressing an exogenous RLK2 protein. Preferably, the RLK2 protein overexpressed in the plant, plant part or plant cell is encoded by (i) an exogenous nucleic acid having at least 60% identity with SEQ ID NO: 1 or a functional fragment, thereof, an orthologue or a paralogue thereof, or a splice variant thereof; or by
(ii) an exogenous nucleic acid encoding a protein having at least 60% identity with SEQ ID NO: 2, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
(iv) an exogenous nucleic acid encoding the same RLK2 protein as any of the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous RLK2 protein. Preferably, the RLK2 protein overexpressed in the plant, plant part or plant cell is encoded by (i) an exogenous nucleic acid having at least 60% identity with SEQ ID NO: 4 or a functional fragment, thereof, an orthologue or a paralogue thereof, or a splice variant thereof; or by
(ii) an exogenous nucleic acid encoding a protein having at least 60% identity with SEQ ID NO: 2, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by
(iv) an exogenous nucleic acid encoding the same RLK2 protein as any of the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 2.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the RLK2 nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, arabidopsis, lentil, banana, canola, cotton, potatoe, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C.O. Lehm), sugar pea (*Pisum sativum* L. convar. *axiphium* Alef emend. C.O. Lehm), also called snow pea, edible-podded pea or mangetout, (*Pisum granda sneida* L. convar. *sneidulo* p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna* subterrane (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, dolichos bean, lablab bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phacosporaceae, for example soybean rust, wherein the recombinant nucleic acid used to generate a transgenic plant comprises a promoter that is functional in the plant cell, operably linked to an RLK2 nucleic acid, which is preferably SEQ ID NO: 4, 1 or 3, and a terminator regulatory sequence.

In one embodiment, the present invention refers to a method for the production of a transgenic plant, transgenic plant part, or transgenic plant cell having increased fungal resistance, comprising (a) introducing a recombinant vector construct according to the present invention into a plant, a plant part or a plant cell and (b) generating a transgenic plant from the plant, plant part or plant cell.

Preferably, the method for the production of the transgenic plant, transgenic plant part, or transgenic plant cell further comprises the step (c) expressing the RLK2 protein, preferably encoded by (i) an exogenous nucleic acid having at least 60% identity with SEQ ID NO: 4, 1, 3, 5-20, 21, 23, 25, 27, 29, 31, 33, or 35, a functional fragment thereof, an orthologue or a paralogue thereof, or a splice variant thereof;

(ii) an exogenous nucleic acid encoding a protein having at least 60% identity with SEQ ID NO: 2, 22, 24, 26, 28, 30, 32, 34, or 36, or a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same RLK2 protein as any of the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step (c) expressing the RLK2 protein, preferably encoded by (i) an exogenous nucleic acid having at least 60% identity with SEQ ID NO: 1, a functional fragment thereof, an orthologue or a paralogue thereof, or a splice variant thereof;

(ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same RLK2 protein as any of the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step (c) expressing the RLK2 protein, preferably encoded by (i) an exogenous nucleic acid having at least 60% identity with SEQ ID NO: 4, a functional fragment thereof, an orthologue or a paralogue thereof, or a splice variant thereof;

(ii) an exogenous nucleic acid encoding a protein having at least 60% identity with SEQ ID NO: 2, or a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii);

preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same RLK2 protein as any of the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 4, 1, 3, 5-20, 21, 23, 25, 27, 29, 31, 33, or 35, or a functional fragment thereof, or an orthologue or a paralogue thereof, or a splice variant thereof;

(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 22, 24, 26, 28, 30, 32, 34, or 36, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) an exogenous nucleic acid encoding the same RLK2 polypeptide as any of the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises (i) the exogenous nucleic acid having at least 60% identity with SEQ ID NO: 4, 1, 3, 5-20, 21, 23, 25, 27, 29, 31, 33, or 35, a functional fragment thereof, an orthologue or a paralogue thereof, or a splice variant thereof;

(ii) the exogenous nucleic acid encoding a protein having at least 60% identity with SEQ ID NO: 2, 22, 24, 26, 28, 30, 32, 34, or 36, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) the exogenous nucleic acid encoding the same RLK2 protein as any of the nucleic acids of (i) to (iii) above, but differing from the nucleic acids of (i) to (iii) above due to the degeneracy of the genetic code;

preferably, the step of harvesting the seeds of the transgenic plant and planting the seeds and growing the seeds to plants, wherein the grown plant(s) comprises (i) the exogenous nucleic acid having at least 60% identity with SEQ ID NO: 4, 1, 3, 5-20, 21, 23, 25, 27, 29, 31, 33, or 35, a functional fragment thereof, an orthologue or a paralogue thereof, or a splice variant thereof;

(ii) the exogenous nucleic acid encoding a protein having at least 60% identity with SEQ ID NO: 2, 22, 24, 26, 28, 30, 32, 34, or 36, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or (iv) the exogenous nucleic acid encoding the same RLK2 protein as any of the nucleic acids of (i) to (iii) above, but differing from the nucleic acids of (i) to (iii) above due to the degeneracy of the genetic code;

is repeated more than one time, preferably, 1, 2, 3, 4, 5, 6, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the RLK2 gene or by directly screening for the RLK2 nucleic acid).

Furthermore, the use of the exogenous RLK2 nucleic acid or the recombinant vector construct comprising the RLK2 nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the RLK2 nucleic acid or RLK2 protein. The harvestable parts may be seeds, roots, leaves and/or flowers comprising the RLK2 nucleic acid or RLK2 protein or parts thereof. Preferred parts of soy plants are soy beans comprising the RLK2 nucleic acid or RLK2 protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the RLK2 nucleic acid or RLK2 protein.

Preferably the harvestable parts of the transgenic plant according to the present invention or the products derived from a transgenic plant comprise an exogenous nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, 1, 3, 5-20, 21, 23, 25, 27, 29, 31, 33, or 35, or a functional fragment, derivative, orthologue, or paralogue thereof, or a splice variant thereof;

(ii) a nucleic acid encoding a RLK2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 22, 24, 26, 28, 30, 32, 34, or 36, or a functional fragment, derivative, orthologue, or paralogue thereof; preferably the RLK2 protein has essentially the same biological activity as a RLK2 protein encoded by SEQ ID NO: 1 or 3; preferably the RLK2 protein confers enhanced fungal resistance relative to control plants; preferably the RLK2 protein has receptor like kinase activity;

(iii) a nucleic acid molecule which hybridizes with a complementary sequence of any of the nucleic acid molecules of (i) or (ii) under high stringency hybridization conditions; preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same RLK2 protein as the RLK2 nucleic acids of (i) to (iii) above, but differing from the RLK2 nucleic acids of (i) to (iii) above due to the degeneracy of the genetic code;

or wherein the harvestable part of the transgenic plant or the product derived from the transgenic plant comprises a RLK2 protein encoded by any one of the RLK2 nucleic acids of (i) to (iv).

Methods for Manufacturing a Product

In one embodiment the method for the production of a product comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably the products obtained by said method comprises an exogenous nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, 1, 3, 5-20, 21, 23, 25, 27, 29, 31, 33, or 35, or a functional fragment, derivative, orthologue, or paralogue thereof, or a splice variant thereof;

(ii) a nucleic acid encoding a RLK2 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 22, 24, 26, 28, 30, 32, 34, or 36, or a functional fragment, derivative, orthologue, or paralogue thereof; preferably the RLK2 protein has essentially the same biological activity as a RLK2 protein encoded by SEQ ID NO: 1 or 3; preferably the RLK2 protein confers enhanced fungal resistance relative to control plants; preferably the RLK2 protein has receptor like kinase activity;

(iii) a nucleic acid molecule which hybridizes with a complementary sequence of any of the nucleic acid molecules of (i) or (ii) under high stringency hybridization conditions; preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same RLK2 protein as the RLK2 nucleic acids of (i) to (iii) above, but differing from the RLK2 nucleic acids of (i) to (iii) above due to the degeneracy of the genetic code;

or wherein the product obtained by said method comprises a RLK2 protein encoded by any one of the RLK2 nucleic acids of (i) to (iv).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/ Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the RLK2 nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of (a) crossing a transgenic plant described herein or a plant obtainable by a method described herein with a second plant;

(b) obtaining a seed or seeds resulting from the crossing step described in (a);

(c) planting said seed or seeds and growing the seed or seeds to plants; and (d) selecting from said plants the plants expressing an RLK2 protein, preferably encoded by (i) an exogenous nucleic acid having at least 60% identity with SEQ ID NO: 4, 1, 3, 5-20, 21, 23, 25, 27, 29, 31, 33, or 35, a functional fragment thereof, an orthologue or a paralogue thereof, or a splice variant thereof;

(ii) an exogenous nucleic acid encoding a protein having at least 60% identity with SEQ ID NO: 2, 22, 24, 26, 28, 30, 32, 34, or 36, or a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a RLK2 protein; preferably wherein the nucleic acid molecule codes for a polypeptide which has essentially identical properties to the polypeptide described in SEQ ID NO: 2; preferably the encoded protein confers enhanced fungal resistance relative to control plants; and/or by (iv) an exogenous nucleic acid encoding the same RLK2 protein as any of the nucleic acids of (i) to (iii) above, but differing from the nucleic acids of (i) to (iii) above due to the degeneracy of the genetic code.

Another preferred embodiment is a method for plant improvement comprising (a) obtaining a transgenic plant by any of the methods of the present invention;

(b) combining within one plant cell the genetic material of at least one plant cell of the plant of (a) with the genetic material of at least one cell differing in one or more gene from the plant cells of the plants of (a) or crossing the transgenic plant of (a) with a second plant;

(c) obtaining seed from at least one plant generated from the one plant cell of (b) or the plant of the cross of step (b);

(d) planting said seeds and growing the seeds to plants; and (e) selecting from said plants, plants expressing the nucleic acid encoding the RLK2 protein; and optionally (f) producing propagation material from the plants expressing the nucleic acid encoding the RLK2 protein.

The transgenic plants may be selected by known methods as described above (e.g., by screening for the presence of one or more markers which are encoded by plant-expressible genes co-transferred with the RLK2 gene or screening for the RLK2 nucleic acid itself).

According to the present invention, the introduced RLK2 nucleic acid may be maintained in the plant cell stably if it is incorporated into a non-chromosomal autonomous replicon or integrated into the plant chromosomes. Whether present in an extra-chromosomal non-replicating or replicating vector construct or a vector construct that is integrated into a chromosome, the exogenous RLK2 nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The RLK2 cDNA (as shown in SEQ ID NO:1) was synthesized in a way that an attB1 recombination site is located in front of the start-ATG and an attB2 recombination site downstream of the stop-codon. The synthesized fragment was cloned into a Gateway pENTRY-B vector (Invitrogen, Life Technologies, Carlsbad, Calif., USA) by using a conventional GATEWAY® BP-reaction according to the manual of the supplier (Invitrogen). The BP reaction was performed in a way that the full-length RLK2 fragment is located in sense direction between the attL1 and attL2 recombination sites.

Figure 2:
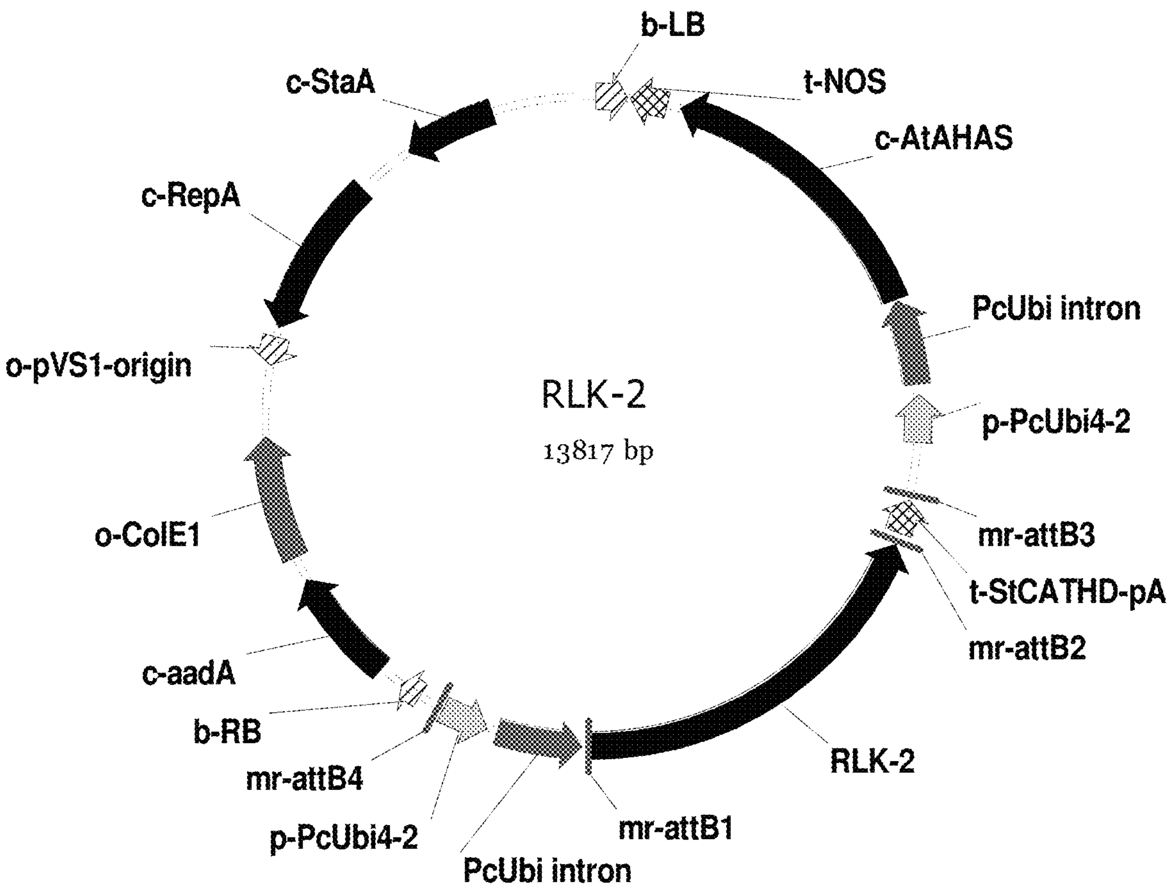
FIG. 2 shows the schematic illustration of the plant transformation vector harboring the RLK2 nucleic acid under control of the parsley ubiquitine promoter.

To obtain the binary plant transformation vector, a triple LR reaction (Gateway system, Invitrogen, Life Technologies, Carlsbad, Calif., USA) was performed according to manufacturer's protocol by using a pENTRY-A vector containing a parsley ubiquitine promoter, the RLK-2 gene in a pENTRY-B vector and a pENTRY-C vector containing the terminator of the cathepsin D inhibitor gene from *Solanum tuberosum*. As target a binary pDEST vector was used which is composed of: (1) a Spectinomycin/Streptomycin resistance cassette for bacterial selection, (2) a pVS1 origin for replication in Agrobacteria, (3) a colE-1 origin of replication for stable maintenance in *E. coli*, and (4) between the right and left border an AHAS selection under control of a pcUbi-promoter (FIG. 2). The recombination reaction was transformed into *E. coli* (DH5alpha), mini-prepped and screened by specific restriction digestions. A positive clone from each vector construct was sequenced and submitted for soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 μM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 $\mu Einstein/m^2s$) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S.

Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 μl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the Agrobacteria were pelleted by centrifugation for 10 min at 5,500×g at 20° C. The pellet was resuspended in liquid CCM to the desired density ($OD_{600}$ 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soybean plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol.—Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 $\mu E/m^2s$. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Growth of Plants

10 $T_1$ plants per event were potted and grown for 3-4 weeks in the phytochamber (16 h-day-und 8 h-night-Rhythm at a temperature of 16 and 22° C. and a humidity of 75%) till the first 2 trifoliate leaves were fully expanded.

4.2 Inoculation

The plants were inoculated with *P. pachyrhizi*.

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of 1-5×$10^5$ spores/ml. For the microscopy, a density of >5×$10^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 50 $T_1$ soybean plants (5 independent events, 10 plants each) expressing the RLK2 protein were inoculated with spores of *Phakopsora pachyrhizi*. The macroscopic disease symptoms caused by *P. pachyrhizi* on the inoculated soybean plants were scored 14 days after inoculation.

The average of the percentage of the leaf area showing fungal colonies or strong yellowing/browning on all leaves was considered as diseased leaf area. At all 50 soybean $T_1$ plants expressing RLK2 (expression checked by RT-PCR) were evaluated in parallel to non-transgenic control plants of the same variety. Non-transgenic soy plants grown in parallel to the transgenic plants were used as control. The average of the diseased leaf area is shown in FIG. 7 for plants exogenously expressing RLK2 compared with wild-type plants. Overexpression of RLK2 reduces the diseased leaf area in comparison to non-transgenic control plants by 26.0% in average over all events generated. This data clearly indicates that the in-planta expression of the RLK2 expression vector construct lead to a lower disease scoring of transgenic plants compared to non-transgenic controls. So, the expression of RLK2 (as shown in SEQ ID NO: 1) in soybean significantly (*: p=0.025) increases the resistance of soybean against soybean rust.

The invention claimed is:

1. A method for preventing, reducing, or delaying *Phakopsora* infection in a soybean plant, a soybean plant part, or a soybean plant cell, the method comprising:

providing a transgenic soybean plant, transgenic soybean plant part, or transgenic soybean plant cell comprising an exogenous nucleic acid encoding a receptor-like kinase 2 (RLK2) protein comprising an amino acid sequence having at least 96% identity with SEQ ID NO: 2, wherein the RLK2 protein confers increased resistance against *Phakopsora* thereto in comparison to a wild type soybean plant, wild type soybean plant part, or wild type soybean plant cell, wherein the exogenous nucleic acid encoding the RLK2 protein is operably linked to a heterologous promoter; and growing the transgenic soybean plant, transgenic soybean plant part, or transgenic soybean plant cell in the presence of a fungal pathogen of the genus *Phakopsora*, wherein *Phakopsora* infection is prevented, reduced, or delayed in the transgenic soybean plant, transgenic soybean plant part, or transgenic soybean plant cell as compared to a wild type soybean plant, wild type soybean plant part, or wild type soybean plant cell.

2. The method of claim 1, wherein the exogenous nucleic acid encodes an RLK2 protein comprising an amino acid sequence having at least 97% identity to SEQ ID NO: 2.

3. The method of claim 1, wherein the exogenous nucleic acid encodes an RLK2 protein comprising an amino acid sequence having at least 98% identity to SEQ ID NO: 2.

4. The method of claim 1, wherein the exogenous nucleic acid encodes an RLK2 protein comprising an amino acid sequence having at least 99% identity to SEQ ID NO: 2.

5. The method of claim 1, wherein the exogenous nucleic acid encodes an RLK2 protein comprising an amino acid sequence having 100% identity to SEQ ID NO: 2.

* * * * *